US012767659B2

(12) United States Patent
Chen et al.

(10) Patent No.: US 12,767,659 B2
(45) Date of Patent: Oct. 20, 2026

(54) TETRACYCLIC DERIVATIVE, METHOD FOR PREPARING SAME AND USE THEREOF IN MEDICINE

(71) Applicants: ZHEJIANG HISUN PHARMACEUTICAL CO., LTD., Taizhou (CN); SHANGHAI ARYL PHARMTECH CO., LTD., Shanghai (CN)

(72) Inventors: Youxi Chen, Shanghai (CN); Chaoying Cheng, Taizhou (CN); Liang Gong, Shanghai (CN); Wentao Mao, Shanghai (CN); Qing Xiang, Shanghai (CN); Weifeng Zhao, Shanghai (CN); Wenwen Zhao, Shanghai (CN); Yanling He, Taizhou (CN); Mingjiang Zhu, Taizhou (CN); Cheng Ye, Shanghai (CN); Taishan Hu, Shanghai (CN); Wenjian Qian, Taizhou (CN); Lei Chen, Taizhou (CN)

(73) Assignees: ZHEJIANG HISUN PHARMACEUTICAL CO., LTD., Taizhou (CN); SHANGHAI ARYL PHARMTECH CO., LTD., Shanghai (CN)

( * ) Notice: Subject to any disclaimer, the term of this patent is extended or adjusted under 35 U.S.C. 154(b) by 727 days.

(21) Appl. No.: 18/022,439

(22) PCT Filed: Aug. 19, 2021

(86) PCT No.: PCT/CN2021/113452

§ 371 (c)(1),
(2) Date: Feb. 21, 2023

(87) PCT Pub. No.: WO2022/037630

PCT Pub. Date: Feb. 24, 2022

(65) Prior Publication Data

US 2023/0295163 A1 Sep. 21, 2023

(30) Foreign Application Priority Data

| | | |
|---|---|---|
| Aug. 21, 2020 | (CN) | 202010847583.7 |
| Nov. 16, 2020 | (CN) | 202011277650.2 |
| Mar. 26, 2021 | (CN) | 202110323813.4 |
| May 19, 2021 | (CN) | 202110543513.7 |
| Jul. 20, 2021 | (CN) | 202110816014.0 |

(51) Int. Cl.
*C07D 471/22* (2006.01)
*A61P 35/00* (2006.01)

(52) U.S. Cl.
CPC ............ *C07D 471/22* (2013.01); *A61P 35/00* (2018.01)

(58) Field of Classification Search
CPC .. C07D 471/22; C07D 405/14; C07D 519/00; C07D 413/14; C07D 471/04; C07D 487/04; A61P 35/00; Y02P 20/55; A61K 31/4985
See application file for complete search history.

(56) References Cited

U.S. PATENT DOCUMENTS

| | | | | |
|---|---|---|---|---|
| 12,054,497 | B2 * | 8/2024 | Zhou | C07D 471/14 |
| 2018/0334454 | A1 | 11/2018 | Lanman et al. | |
| 2019/0177338 | A1 | 6/2019 | Kettle | |
| 2022/0064141 | A1 | 3/2022 | Fang | |
| 2022/0389029 | A1 | 12/2022 | Guo | |
| 2023/0084095 | A1 | 3/2023 | Zhou et al. | |

FOREIGN PATENT DOCUMENTS

| | | | | |
|---|---|---|---|---|
| CN | 106488910 | A | 3/2017 | |
| CN | 110997668 | A | 4/2020 | |
| CN | 111484477 | A | 8/2020 | |
| CN | 112300194 | A | 2/2021 | |
| EP | 4053118 | A1 | 9/2022 | |
| TW | 201938561 | A | 10/2019 | |
| WO | 2015054572 | A1 | 4/2015 | |
| WO | 2021052499 | A1 | 3/2021 | |
| WO | WO-2021083167 | A1 * | 5/2021 | C07D 498/22 |
| WO | 2022037630 | A1 | 2/2022 | |

OTHER PUBLICATIONS

International Search Report for PCT/CN2021/113452 mailed Nov. 9, 2021, ISA/CN.
The 1st Office Action regarding Chinese Patent Application No. CN202180057791.X, Mailing date: Apr. 10, 2024. English Translation.

* cited by examiner

*Primary Examiner* — Kamal A Saeed
*Assistant Examiner* — Meghan C Heasley
(74) *Attorney, Agent, or Firm* — Yue (Robert) Xu; Apex Attorneys at Law, LLP

(57) ABSTRACT

The present invention relates to a tetracyclic derivative, a method for preparing same and the use thereof in medicine. In particular, the present invention relates to a tetracyclic derivative represented by general formula (I), a method for preparing same and a pharmaceutically acceptable salt thereof, and the use thereof as a therapeutic agent, especially as a K-Ras GTPase inhibitor, with definitions of each substituent in general formula (I) being the same as of which are defined in the description.

9 Claims, 1 Drawing Sheet

TETRACYCLIC DERIVATIVE, METHOD FOR PREPARING SAME AND USE THEREOF IN MEDICINE

CROSS REFERENCE TO RELATED APPLICATIONS

This application is the national phase of International Application No. PCT/CN2021/113452, titled "TETRACYCLIC DERIVATIVE, METHOD FOR PREPARING SAME AND USE THEREOF IN MEDICINE", which claims the priority of:

1) Chinese Patent Application No. 202010847583.7, filed with the China National Intellectual Property Administration on Aug. 21, 2020, and titled with "TETRACYCLIC DERIVATIVE, METHOD FOR PREPARING SAME AND USE THEREOF IN MEDICINE";
2) Chinese Patent Application No. 202011277650.2, filed with the China National Intellectual Property Administration on Nov. 16, 2020, and titled with "TETRACYCLIC DERIVATIVE, METHOD FOR PREPARING SAME AND USE THEREOF IN MEDICINE";
3) Chinese Patent Application No. 202110323813.4, filed with the China National Intellectual Property Administration on Mar. 26, 2021, and titled with "TETRACYCLIC DERIVATIVE, METHOD FOR PREPARING SAME AND USE THEREOF IN MEDICINE";
4) Chinese Patent Application No. 202110543513.7, filed with the China National Intellectual Property Administration on May 19, 2021, and titled with "TETRACYCLIC DERIVATIVE, METHOD FOR PREPARING SAME AND USE THEREOF IN MEDICINE"; and
5) Chinese Patent Application No. 202110816014.0, filed with the China National Intellectual Property Administration on Jul. 20, 2021, and titled with "TETRACYCLIC DERIVATIVE, METHOD FOR PREPARING SAME AND USE THEREOF IN MEDICINE";

which are hereby incorporated by reference in their entirety.

FIELD

The present disclosure relates to a tetracyclic derivative, a method for preparing the same, a pharmaceutical composition comprising the derivative and use thereof as a therapeutic agent, especially as a K-Ras GTPase inhibitor.

BACKGROUND

RAS represents a group of closely related monomeric globular proteins (with a molecular weight of 21 kDa) of 189 amino acids. It is attached to the plasma membrane and binds to GDP or GTE Under normal developmental or physiological conditions, RAS is activated by receiving growth factor and various other extracellular signals, and is responsible for regulating functions such as cell growth, survival, migration and differentiation. RAS functions as a molecular switch, and the on/off state of RAS protein is determined by the bound nucleotide, where in the active signaling conformation, RAS is bound to GTP, and in the inactive conformation, RAS is bound to GDP. In the case that RAS is bound to GDP, it is dormant or in the resting or off state, thus being "inactive". When cells are exposed to and respond to certain growth-promoting stimuli, RAS is induced to exchange bound GDP for GTP. Upon binding to GTP, RAS is "on" and is able to interact with and activate other proteins (its "downstream targets"). RAS protein itself has a very weak intrinsic ability to hydrolyze GTP into GDP to thereby turn itself in the off state. To turn RAS in the off state requires an exogenous protein called GTPase-activating protein (GAP), which interacts with RAS and can greatly facilitate the exchange of GTP for GDP. Any mutation in RAS that affects its ability to interact with GAP or exchange GTP for GDP can result in prolonged activation of the protein and thus a prolonged signal informing cells to continue growing and dividing. Therefore, these signals lead to cell growth and division, and overactive RAS signaling may ultimately lead to cancer.

Structurally, RAS protein contains a G domain responsible for the enzymatic activity of RAS—binding and hydrolyzing guanine nucleotide (GTPase reaction). It further contains a C-terminal extension region known as CAAX box, which can be post-translationally modified and targets the protein to the membrane. The G domain is approximately 21-25 kDa in size and contains a phosphate binding loop (P-loop). The P-loop represents the pocket in the protein that binds nucleotides, and it is a rigid part of the domain with conserved amino acid residues that are necessary for binding and hydrolyzing nucleotides (glycine 12, threonine 26 and lysine 16). The G domain also contains the so-called Switch I region (residues 30-40) and Switch II region (residues 60-76), both of which are dynamic parts of the protein. This dynamic part is often referred to as a "spring loaded" mechanism due to its ability to transition between resting state and loading state. The main interaction is the hydrogen bonds formed by threonine-35 and glycine-60 with the γ-phosphate of GTP, which maintain the Switch I region and Switch II region in their active conformations, respectively. After hydrolysis of GTP and release of phosphate, the two regions convert into inactive GDP conformations.

Among members of the RAS family, oncogenic mutations are most commonly found in KRAS (85%), while less found in NRAS (12%) and HRAS (3%). KRAS mutation is prevalent in the three most deadly cancer types in the United States: pancreatic cancer (95%), colorectal cancer (45%), and lung cancer (25%), and it is also found in other cancer types including multiple myeloma, uterine cancer, cholangiocarcinoma, gastric cancer, bladder cancer, diffuse large B-cell lymphoma, rhabdomyosarcoma, squamous cell carcinoma, cervical cancer and testicular germ cell carcinoma, while rarely found in breast cancer, ovarian cancer and brain cancer (<2%). In non-small cell lung cancer (NSCLC), KRAS G12C is the most common mutation, accounting for nearly half of all KRAS mutations, followed by G12V and G12D. In non-small cell lung cancer, the increased mutation frequency of specific alleles is mostly attributed to the classic smoking-induced mutation (replacement of G:C to T:A), resulting in mutations of KRAS G12C (GGT to TGT) and G12V (GGT to GTT).

A large genomic study has shown that KRAS mutation in lung cancer including G12C, is mutually exclusive with other known driver oncogenic mutations in NSCLC including EGFR, ALK, ROS1, RET, and BRAF, suggesting the uniqueness of KRAS mutation in lung cancer. Moreover, KRAS mutation often co-occurs with certain co-mutations such as STK11, KEAP1, and TP53, which cooperate with mutated RAS to transform cells into highly malignant and invasive tumor cells.

Three RAS oncogenes constitute the most frequently mutated gene family in human cancers. Disappointingly, despite more than three decades of research and efforts, there are still no clinically effective anti-RAS therapies, and to target this gene with small molecules is challenging. Therefore, there is an urgent need in the art for small molecules for targeting RAS (for example, K-RAS, H-RAS and/or N-RAS) and use thereof in treating various diseases, such as cancer.

At present, there is intense competition for clinical development of KRAS inhibitors in China and abroad. Among them, the KRAS enzyme inhibitor MRTX-849 developed by Mirati Therapeutics Inc. has entered phase II of clinical trials for preventing and treating diseases such as advanced solid tumor, metastatic colorectal cancer and metastatic non-small cell lung cancer. There are also other KRAS inhibitors in development, including AMG-510 (Amgen Inc, phase 3). Early clinical studies have shown that KRAS inhibitors can control and alleviate disease progression in patients with non-small cell lung cancer, and can shrink tumor size in patients with advanced lung cancer and colorectal cancer. A series of patent applications of KRAS inhibitors have been disclosed, including WO2020047192, WO2019099524 and WO2018217651, which shows that some progress has been made in the research and application of KRAS inhibitors. However, the existing KRAS inhibitors are still not satisfactory in terms of effectiveness and safety, and there is still much room for improvement. Therefore, it is still necessary to continue research and development of new KRAS inhibitors.

SUMMARY

The present inventors unexpectedly found in the research that a tetracyclic derivative represented by the following general formula (I), or a stereoisomer, tautomer, or pharmaceutically acceptable salt thereof can be used as an effective KRAS inhibitor with good efficacy and safety.

Therefore, in a first aspect, the present disclosure provides a tetracyclic derivative represented by general formula (I), or a stereoisomer, tautomer, or pharmaceutically acceptable salt thereof:

(I)

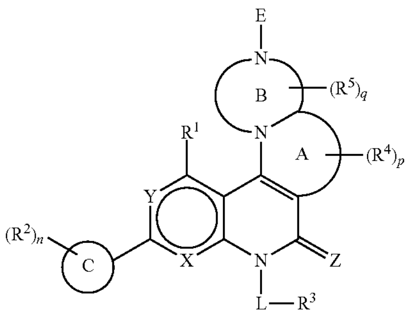

wherein:

E is selected from the group consisting of

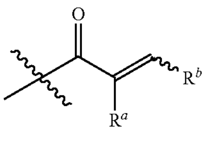

and

-continued

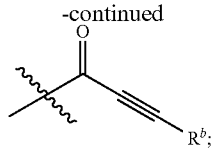

L is selected from the group consisting of a chemical bond and $C_1$-$C_6$ alkylene; wherein the alkylene is further optionally substituted by one or more substituents selected from the group consisting of alkyl, halogen and hydroxyl; preferably, L is selected from the group consisting of a chemical bond, —$CH_2$—, —$CH_2CH_2$— and —$CH(CH_3)$—; more preferably, L is a chemical bond;

X and Y are each independently selected from the group consisting of N and $CR^c$;

Z is selected from the group consisting of O and $NR^6$;

ring A is selected from the group consisting of a 5-8 membered monocyclic heterocyclic group and a 5-10 membered bridged heterocyclic group, wherein the monocyclic heterocyclic group or the bridged heterocyclic group contains one or more N, O or $S(O)_r$;

ring B is a 4-12 membered heterocycle containing 2 nitrogen atoms;

ring C is selected from the group consisting of aryl, heteroaryl and a fused ring;

$R^a$ is selected from the group consisting of a hydrogen atom and fluorine;

$R^b$ is selected from the group consisting of a hydrogen atom, —$CH_2F$, —$CHF_2$,

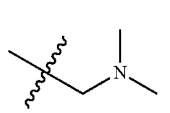

and

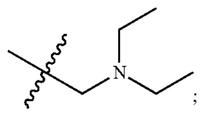

;

$R^b$ is selected from the group consisting of a hydrogen atom, halogen, alkyl and alkoxy; wherein the alkyl or alkoxy is further optionally substituted by one or more substituents selected from the group consisting of halogen, hydroxyl, cyano, alkyl and alkoxy; $R^c$ is preferably halogen, more preferably fluorine or chlorine;

$R^1$ is selected from the group consisting of a hydrogen atom, halogen, alkyl and alkoxy; wherein the alkyl or alkoxy is further optionally substituted by one or more substituents selected from the group consisting of halogen, hydroxyl, cyano, alkyl and alkoxy; $R^1$ is preferably a hydrogen atom;

$R^2$ is the same or different, each independently selected from the group consisting of a hydrogen atom, alkyl, halogen, nitro, cyano, cycloalkyl, heterocyclyl, aryl, heteroaryl, =O, —OR', —$C(O)R^7$, —$C(O)OR^7$, —$NHC(O)R^7$, —$NHC(O)OR^7$, —$NR^8R^9$, —$C(O)NR^8R^9$, —$CH_2NHC(O)OR^7$, —$CH_2NR^8R^9$, and —$S(O)_rR^7$; wherein the alkyl, cycloalkyl, heterocyclyl, aryl or heteroaryl is further optionally substituted by one or more substituents selected from the group consisting of alkyl, halogen, nitro, cyano, cycloalkyl, heterocyclyl, aryl, heteroaryl, oxo (=O), —OR', —$C(O)R^7$, —$C(O)OR^7$, —$NHC(O)R^7$, —$NHC(O)OR^7$, —$NR^8R^9$, —$C(O)NR^8R^9$, —$CH_2NHC(O)OR^7$, —$CH_2NR^8R^9$, and —$S(O)_rR^7$;

$R^3$ is selected from the group consisting of alkyl, aryl, and heteroaryl; wherein the alkyl, aryl or heteroaryl is further optionally substituted by one or more $R^A$; $R^3$ is preferably heteroaryl;

$R^A$ is the same or different, each independently selected from the group consisting of alkyl, halogen, nitro, cyano, cycloalkyl, heterocyclyl, aryl, heteroaryl, =O, —OR', —C(O)$R^7$, —C(O)O$R^7$, —NHC(O)$R^7$, —NHC(O)O$R^7$, —N$R^8R^9$, —C(O)N$R^8R^9$, —$CH_2$NHC(O)O$R^7$, —$CH_2$N$R^8R^9$, and —S(O)$_r$$R^7$; wherein the alkyl, cycloalkyl, heterocyclyl, aryl or heteroaryl is further optionally substituted by one or more substituents selected from the group consisting of alkyl, halogen, nitro, cyano, cycloalkyl, heterocyclyl, aryl, heteroaryl, =O, —C(O)$R^7$, —C(O)O$R^7$, —NHC(O)$R^7$, —NHC(O)O$R^7$, —N$R^8R^9$, —C(O)N$R^8R^9$, —$CH_2$NHC(O)O$R^7$, —$CH_2$N$R^8R^9$, and —S(O)$_r$$R^7$; wherein at least one $R^A$ is —S(O)$_r$$R^7$; preferably, $R^3$ is preferably heteroaryl; wherein the heteroaryl is further substituted by two $R^A$, with one $R^A$ being alkyl, and the other $R^A$ being —S(O)$_r$$R^7$;

$R^4$ is the same or different, each independently selected from the group consisting of a hydrogen atom, hydroxyl, halogen, nitro, cyano, alkyl, alkoxy, haloalkyl, haloalkoxy, deuterated alkyl, cycloalkyl, heterocyclyl, aryl, heteroaryl, =O, —C(O)$R^7$, —C(O)O$R^7$, —OC(O)$R^7$, —N$R^8R^9$, —C(O)N$R^8R^9$, —$SO_2$N$R^8R^9$, and —N$R^8$C(O)$R^9$; $R^4$ is preferably a hydrogen atom, methyl, deuterated methyl or =O;

$R^5$ is the same or different, each independently selected from the group consisting of a hydrogen atom, halogen, hydroxyl, alkyl and alkoxy, preferably a hydrogen atom or alkyl;

$R^6$ is selected from the group consisting of a hydrogen atom, alkyl, —C(O)$R^{13}$ and —S(O)$_2$$R^{13}$;

$R^7$ is selected from the group consisting of a hydrogen atom, alkyl, cycloalkyl, heterocyclyl, aryl and heteroaryl, wherein the alkyl, cycloalkyl, heterocyclyl, aryl or heteroaryl is further optionally substituted by one or more substituents selected from the group consisting of hydroxyl, halogen, nitro, cyano, alkyl, alkoxy, haloalkyl, haloalkoxy, cycloalkyl, heterocyclyl, aryl, heteroaryl, =O, —C(O)$R^{10}$, —C(O)O$R^{10}$, —OC(O)$R^{10}$, —N$R^{11}R^{12}$, —C(O)N$R^{11}R^{12}$, —$SO_2$N$R^{11}R^{12}$ and —N$R^{11}$C(O)$R^{12}$;

$R^8$ and $R^9$ are each independently selected from the group consisting of a hydrogen atom, hydroxyl, halogen, alkyl, alkoxy, cycloalkyl, heterocyclyl, aryl and heteroaryl, wherein the alkyl, alkoxy, cycloalkyl, heterocyclyl, aryl or heteroaryl is further optionally substituted by one or more substituents selected from the group consisting of hydroxyl, halogen, nitro, cyano, alkyl, alkoxy, cycloalkyl, heterocyclyl, aryl, heteroaryl, =O, —C(O)$R^{10}$, —C(O)O$R^{10}$, —OC(O)$R^{10}$, —N$R^{11}R^{12}$, —C(O)N$R^{12}$, —$SO_2$N$R^{11}R^{12}$, —$SO_2$N$R^{11}R^{12}$, alternatively, $R^8$ and $R^9$ form a 4-8 membered heterocyclic group together with the atom they are connected to, wherein the 4-8 membered heterocyclic group contains one or more N, O or S(O)$_r$, and the 4-8 membered heterocyclic group is further optionally substituted by one or more substituents selected from the group consisting of hydroxyl, halogen, nitro, cyano, alkyl, alkoxy, cycloalkyl, heterocyclyl, aryl, heteroaryl, =O, —C(O)$R^{10}$, —C(O)O$R^{10}$, —OC(O)$R^{10}$, —N$R^{11}R^{12}$, —C(O)N$R^{11}R^{12}$, —$SO_2$N$R^{11}R^{12}$, and —N$R^{11}$C(O)$R^{12}$;

$R^{10}$, $R^{11}$ and $R^{12}$ are each independently selected from the group consisting of a hydrogen atom, alkyl, amino, cycloalkyl, heterocyclyl, aryl and heteroaryl, wherein the alkyl, cycloalkyl, heterocyclyl, aryl or heteroaryl is further optionally substituted by one or more substituents selected from the group consisting of hydroxyl, halogen, nitro, amino, cyano, alkyl, alkoxy, cycloalkyl, heterocyclyl, aryl, heteroaryl, carboxyl and carboxylate;

$R^{13}$ is alkyl, preferably methyl;

n is selected from the group consisting of 0, 1, 2 and 3;

p is selected from the group consisting of 0, 1 and 2;

q is selected from the group consisting of 0, 1 and 2; and r is selected from the group consisting of 0, 1 and 2.

In a preferred embodiment of the present disclosure, the compound represented by general formula (I), or the stereoisomer, tautomer, or pharmaceutically acceptable salt thereof is a compound represented by general formula (II), or a stereoisomer, tautomer, or pharmaceutically acceptable salt thereof:

(II)

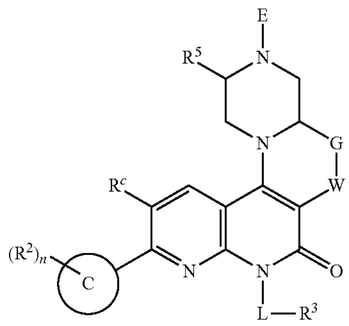

wherein:

G is selected from the group consisting of O, C=O and C$R^dR^e$;

W is selected from the group consisting of N$R^f$, O and C$R^dR^e$;

provided that: when G is O, W is C$R^dR^e$; or when W is N$R^f$, G is C=O;

$R^d$ and $R^e$ are the same or different, each independently selected from the group consisting of a hydrogen atom, halogen, alkyl and alkoxy, preferably a hydrogen atom;

$R^f$ is selected from the group consisting of a hydrogen atom, alkyl and deuterated alkyl, preferably alkyl or deuterated alkyl, more preferably methyl or deuterated methyl;

$R^5$ is selected from the group consisting of a hydrogen atom and alkyl, wherein the alkyl is preferably methyl; and ring C, $R^2$, $R^3$, $R^c$, E, L and n are as defined in general formula (I).

In a preferred embodiment of the present disclosure, the compound represented by general formula (II), or the stereoisomer, tautomer, or pharmaceutically acceptable salt thereof is a compound represented by general formula (III) or (IV), or a stereoisomer, tautomer, or pharmaceutically acceptable salt thereof:

(III)

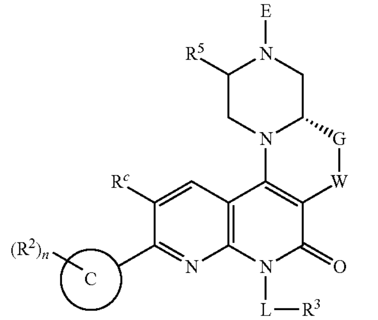

(IV)

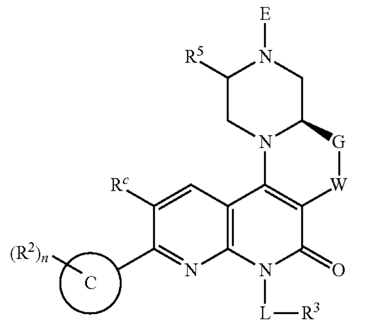

wherein: ring C, $R^2$, $R^3$, $R^5$, $R^c$, E, L, G, W and n are as defined in general formula (II).

In a preferred embodiment of the present disclosure, the compound represented by general formula (I) or (II), or the stereoisomer, tautomer, or pharmaceutically acceptable salt thereof is a compound represented by general formula (V) or (VI), or a stereoisomer, tautomer, or pharmaceutically acceptable salt thereof:

(V)

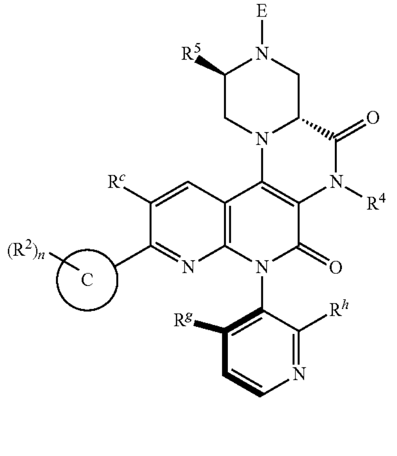

-continued (VI)

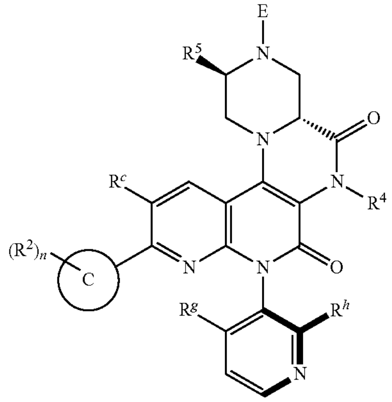

wherein:

$R^g$ is selected from the group consisting of a hydrogen atom, alkyl and —$SR^7$, preferably methyl or —S—$CH_3$;

$R^h$ is selected from the group consisting of a hydrogen atom and alkyl, preferably methyl or isopropyl;

$R^4$ is selected from the group consisting of alkyl and deuterated alkyl, preferably methyl or deuterated methyl;

$R^7$ is alkyl, preferably methyl; and ring C, $R^2$, $R^5$, $R^c$, E and n are as defined in general formula (II).

In a preferred embodiment of the present disclosure, for the compound represented by general formula (I), (II), (III), (IV), (V) or (VI), or the stereoisomer, tautomer, or pharmaceutically acceptable salt thereof, E is selected from the group consisting of

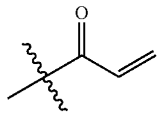
and
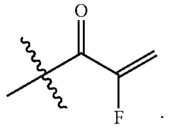
.

In a preferred embodiment of the present disclosure, for the compound represented by general formula (I), (II), (III), (IV), (V) or (VI), or the stereoisomer, tautomer, or pharmaceutically acceptable salt thereof,

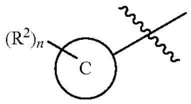

is selected from the group consisting of:

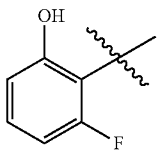
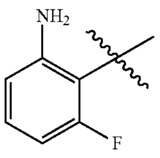
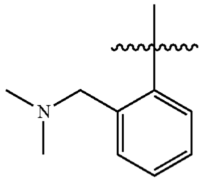

-continued

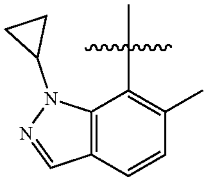

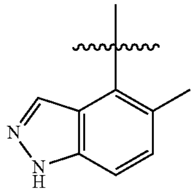

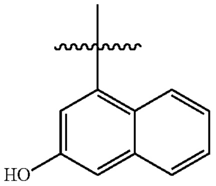

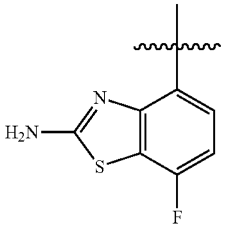

and

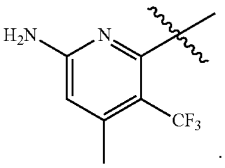

.

In a preferred embodiment of the present disclosure, for the compound represented by general formula (I), (II), (III), (IV), (V) or (VI), or the stereoisomer, tautomer, or pharmaceutically acceptable salt thereof, R is halogen, preferably fluorine or chlorine.

In a preferred embodiment of the present disclosure, for the compound represented by general formula (I), (II), (III), (IV), (V) or (VI), or the stereoisomer, tautomer, or pharmaceutically acceptable salt thereof:

$R^2$ is selected from the group consisting of a hydrogen atom, halogen, hydroxyl, alkyl, alkoxy, cycloalkyl and —$NR^8R^9$, wherein the alkyl, alkoxy or cycloalkyl is further optionally substituted by one or more substituents selected from the group consisting of halogen, hydroxyl, alkyl, alkoxy and —$NR^8R^9$; more preferably, $R^2$ is selected from group consisting of fluorine, chlorine, bromine, hydroxyl, amino, methyl, ethyl, trifluoromethyl, cyclopropyl and

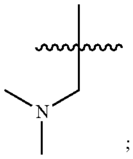

;

further more preferably, $R^2$ is hydroxyl or fluorine; and wherein $R^8$ and $R^9$ are as defined in general formula (I).

In a preferred embodiment of the present disclosure, for the compound represented by general formula (I), (II), (III), or (IV), or the stereoisomer, tautomer, or pharmaceutically acceptable salt thereof, $R^3$ is selected from the group consisting of

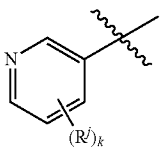

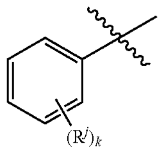

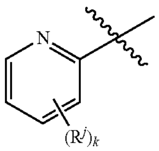

-continued

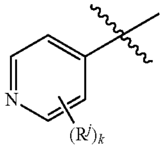

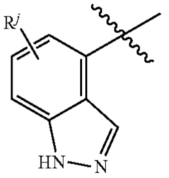

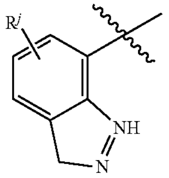

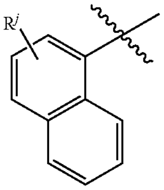

and

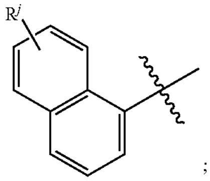

;

wherein:

$R^j$ is selected from the group consisting of a hydrogen atom, halogen, nitro, cyano, hydroxyl, amino, alkyl, alkoxy, —$SR^7$, haloalkyl and haloalkoxy, and at least one $R^j$ is —$SR^7$; $R^j$ is preferably alkyl or —$SR^7$, more preferably methyl, ethyl or isopropyl;

$R^7$ is alkyl, preferably methyl;

k is selected from the group consisting of 0, 1, 2, 3, 4 and 5.

In a preferred embodiment of the present disclosure, for the compound represented by general formula (I), (II), (III), or (IV), or a stereoisomer, tautomer, or pharmaceutically acceptable salt thereof, $R^3$ is selected from the group consisting of (

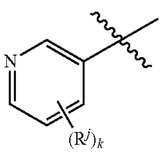

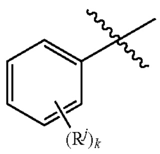

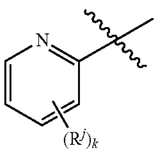

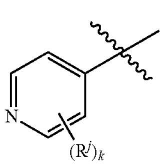

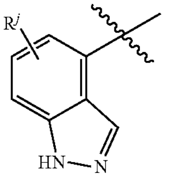

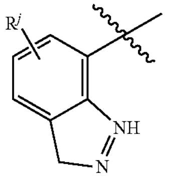

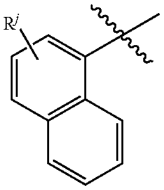

and

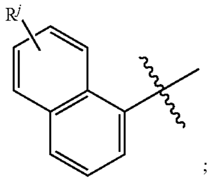

;

wherein:

$R^j$ is selected from the group consisting of a hydrogen atom, halogen, nitro, cyano, hydroxyl, amino, alkyl, alkoxy, —$SR^7$, haloalkyl and haloalkoxy, and at least one $R^j$ is —$SR^7$; $R^j$ is preferably alkyl or —$SR^7$, more preferably methyl, ethyl or isopropyl;

provided that:

one $R^j$ is —$SR^7$;

and the other $R^j$ is alkyl, wherein the alkyl is preferably methyl, ethyl or isopropyl; more preferably isopropyl;

$R^7$ is alkyl, preferably, $R^7$ is methyl; and k is 2.

In a preferred embodiment of the present disclosure, for the compound represented by general formula (I), (II), (III), or (IV), or the stereoisomer, tautomer, or pharmaceutically acceptable salt thereof, $R^3$ is selected from the group consisting of N and

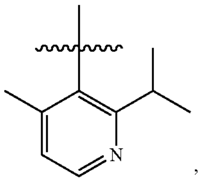
,
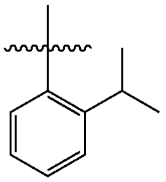
and

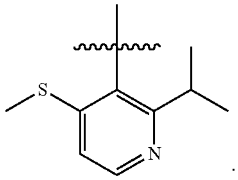
.

In a preferred embodiment of the present disclosure, for the compound represented by general formula (I), or the stereoisomer, tautomer, or pharmaceutically acceptable salt thereof, R is selected from the group consisting of alkyl and deuterated alkyl, preferably methyl or deuterated methyl.

In a preferred embodiment of the present disclosure, for the compound represented by general formula (II), (III) or (IV), or the stereoisomer, tautomer, or pharmaceutically acceptable salt thereof, G is O, and W is $CH_2$;

In a preferred embodiment of the present disclosure, for the compound represented by general formula (II), (III) or (IV), or the stereoisomer, tautomer, or pharmaceutically acceptable salt thereof, G is $CH_2$, and W is O;

In a preferred embodiment of the present disclosure, for the compound represented by general formula (II), (III) or (IV), or the stereoisomer, tautomer, or pharmaceutically acceptable salt thereof, G is C═O, and W is $NCH_3$.

In a preferred embodiment of the present disclosure, for the compound represented by general formula (I), (II), (III), (IV), (V) or (VI), or the stereoisomer, tautomer, or pharmaceutically acceptable salt thereof, $R^5$ is selected from the group consisting of a hydrogen atom and methyl.

In a preferred embodiment of the present disclosure, for the compound represented by general formula (I), (II), (III) or (IV), or the stereoisomer, tautomer, or pharmaceutically acceptable salt thereof, L is selected from the group consisting of a chemical bond, $—CH_2—$, $—CH_2CH_2—$ and $—CH(CH_3)—$; more preferably, L is a chemical bond.

In a preferred embodiment of the present disclosure, for the compound represented by general formula (I), (II), (III) or (IV), or the stereoisomer, tautomer, or pharmaceutically acceptable salt thereof, L is a chemical bond, and $R^3$ is heteroaryl;

more preferably, L is a chemical bond, and $R^3$ is heteroaryl substituted by methylthio ($—S—CH_3$);

further preferably, L is a chemical bond, and $R^3$ is pyridyl substituted by methylthio;

especially preferably, L is a chemical bond, and $R^3$ is

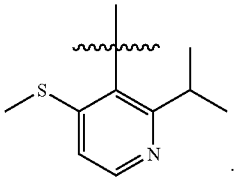 [SMILES: *c1c(SC)ccnc1C(C)C]
.

Alternatively, in a preferred embodiment of the present disclosure, for the compound represented by general formula (V) or (VI), or the stereoisomer, tautomer, or pharmaceutically acceptable salt thereof, $R^g$ is $—S—CH_3$.

In a preferred embodiment of the present disclosure, for the compound represented by general formula (I), (II), (III) or (IV), or the stereoisomer, tautomer, or pharmaceutically acceptable salt thereof, ring C is bicyclic heteroaryl or naphtyl, and the bicyclic heteroaryl or napthyl is optionally substituted by hydroxyl or amino;

more preferably,

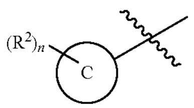
is
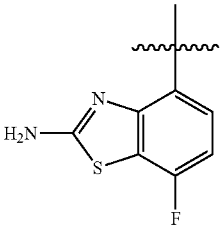
or

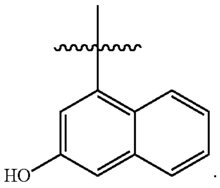
.

The typical compounds of the present disclosure include, but are not limited to:

| Compound number | Structure | Name |
|---|---|---|
| 7 | 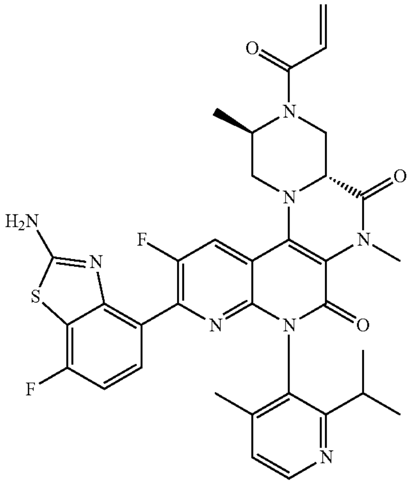 [SMILES: C=CC(=O)N1C[C@@H]2C(=O)N(C)c3c(c4cc(F)c(-c5ccc(F)c6sc(N)nc56)nc4n(-c4c(C)ccnc4C(C)C)c3=O)N2C[C@H]1C] | (2R,4aR)-3-acryloyl-10-(2-amino-7-fluorobenzo[d]thiazol-4-yl)-11-fluoro-8-(2-isopropyl-4-methylpyridin-3-yl)-2,6-dimethyl-2,3,4,4a,6,8-hexahydro-1H-pyrazino[1',2':4,5]pyrazino[2,3-c][1,8]naphthyridine-5,7-dione |
| 8 | 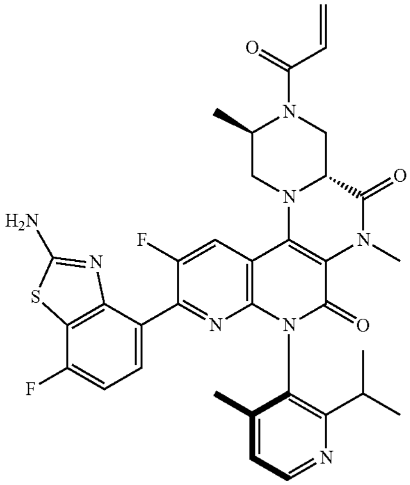 | (2R,4aR,8R)-3-acryloyl-10-(2-amino-7-fluorobenzo[d]thiazol-4-yl)-11-fluoro-8-(2-isopropyl-4-methylpyridin-3-yl)-2,6-dimethyl-2,3,4,4a,6,8-hexahydro-1H-pyrazino[1',2':4,5]pyrazino[2,3-c][1,8]naphthyridine-5,7-dione |
| 9 | 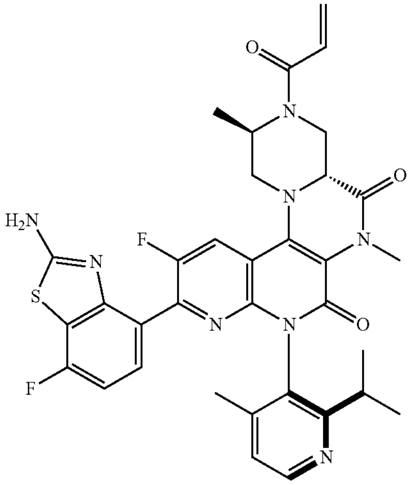 | (2R,4aR,8S)-3-acryloyl-10-(2-amino-7-fluorobenzo[d]thiazol-4-yl)-11-fluoro-8-(2-isopropyl-4-methylpyridin-3-yl)-2,6-dimethyl-2,3,4,4a,6,8-hexahydro-1H-pyrazino[1',2':4,5]pyrazino[2,3-c][1,8]naphthyridine-5,7-dione |

-continued

| Compound number | Structure | Name |
|---|---|---|
| 10 | 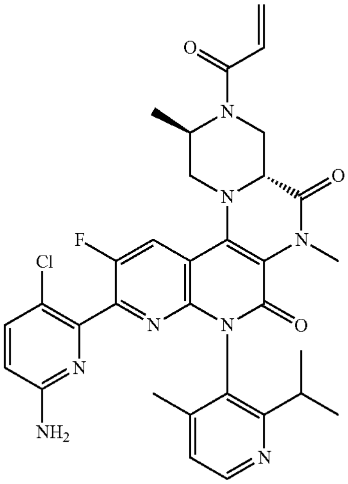 [SMILES: C=CC(=O)N1C[C@@H]2C(=O)N(C)c3c(c4cc(F)c(-c5nc(N)ccc5Cl)nc4n(-c4c(C)ccnc4C(C)C)c3=O)N2C[C@H]1C] | (2R,4aR)-3-acryloyl-10-(6-amino-3-chloropyridin-2-yl)-11-fluoro-8-(2-isopropyl-4-methylpyridin-3-yl)-2,6-dimethyl-2,3,4,4a,6,8-hexahydro-1H-pyrazino[1',2':4,5]pyrazino[2,3-c][1,8]naphthyridine-5,7-dione |
| 11 | 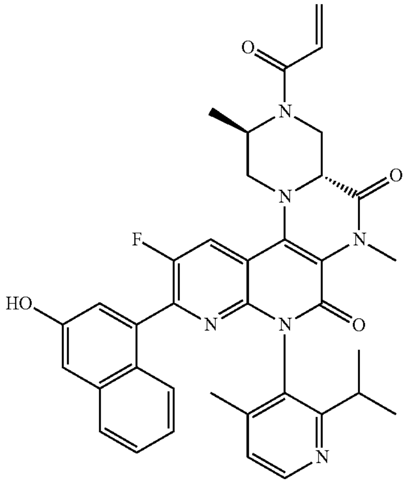 [SMILES: C=CC(=O)N1C[C@@H]2C(=O)N(C)c3c(c4cc(F)c(-c5cc(O)cc6ccccc56)nc4n(-c4c(C)ccnc4C(C)C)c3=O)N2C[C@H]1C] | (2R,4aR)-3-acryloyl-11-fluoro-10-(3-hydroxynaphthalen-1-yl)-8-(2-isopropyl-4-methylpyridin-3-yl)-2,6-dimethyl-2,3,4,4a,6,8-hexahydro-1H-pyrazino[1',2':4,5]pyrazino[2,3-c][1,8]naphthyridine-5,7-dione |
| 16 | 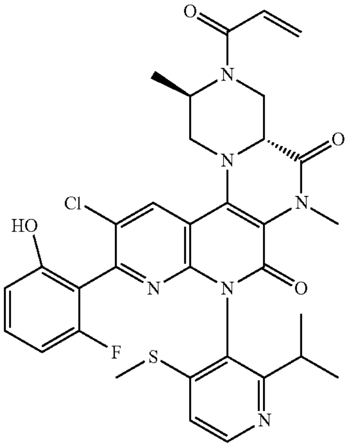 [SMILES: C=CC(=O)N1C[C@@H]2C(=O)N(C)c3c(c4cc(Cl)c(-c5c(O)cccc5F)nc4n(-c4c(SC)ccnc4C(C)C)c3=O)N2C[C@H]1C] | (2R,4aR)-3-acryloyl-11-chloro-10-(2-fluoro-6-hydroxyphenyl)-8-(2-isopropyl-4-(methylthio)pyridin-3-yl)-2,6-dimethyl-2,3,4,4a,6,8-hexahydro-1H-pyrazino[1',2':4,5]pyrazino[2,3-c][1,8]naphthyridine-5,7-dione |

-continued

| Compound number | Structure | Name |
|---|---|---|
| 17 | 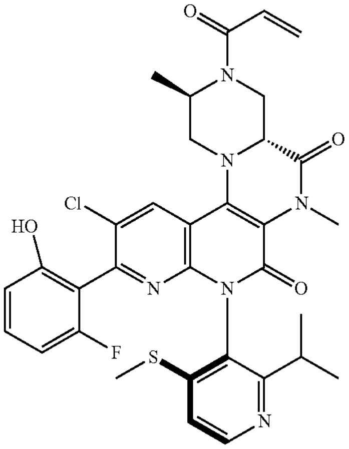 | |
| 18 | 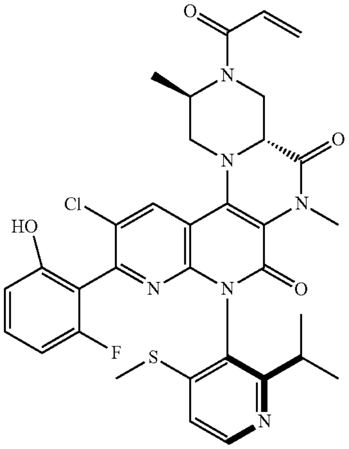 | |

or a stereoisomer, tautomer, or pharmaceutically acceptable salt thereof.

Note: If there is a discrepancy between a structure formula and a name provided for the structure formula, the structure formula shall prevail.

Further, the present disclosure provides a method for producing the compound represented by general formula (I), or the stereoisomer, tautomer, or pharmaceutically acceptable salt thereof, comprising:

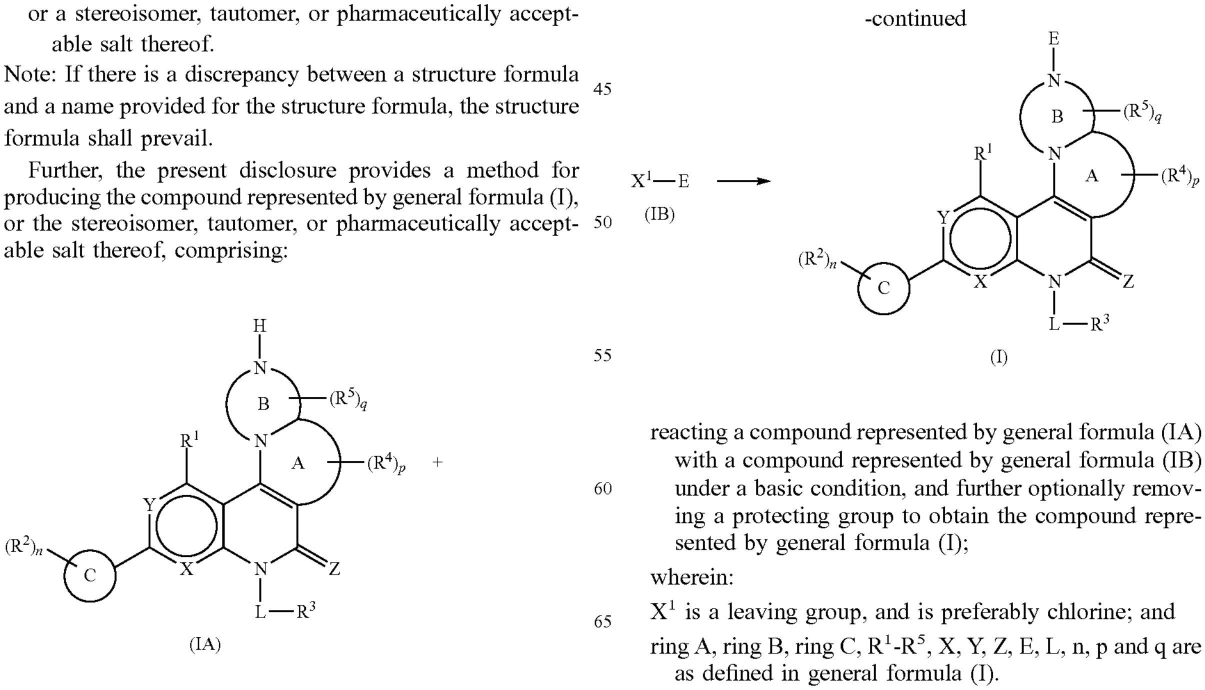

(IA)

-continued (IB)

(I)

reacting a compound represented by general formula (IA) with a compound represented by general formula (IB) under a basic condition, and further optionally removing a protecting group to obtain the compound represented by general formula (I);

wherein:

$X^1$ is a leaving group, and is preferably chlorine; and ring A, ring B, ring C, $R^1$-$R^5$, X, Y, Z, E, L, n, p and q are as defined in general formula (I).

Furthermore, the present disclosure provides a compound represented by general formula (IA), or a stereoisomer, tautomer, or pharmaceutically acceptable salt thereof, (IA)

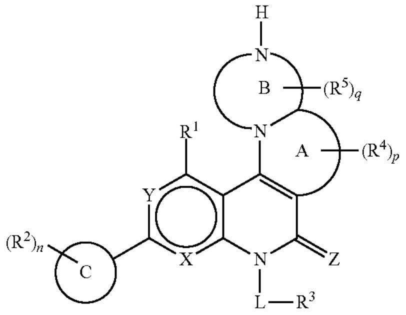

wherein: ring A, ring B, ring C, $R^1$-$R^5$, X, Y, Z, L, n, p and q are as defined in general formula (I).

Typical compounds represented by general formula (IA) include, but are not limited to:

| Compound number | Structure | Name |
|---|---|---|
| 7k | 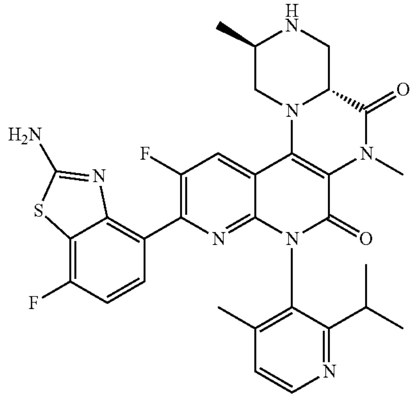 [SMILES: Cc1ccnc(C(C)C)c1-n1c(=O)c2c(c3cc(F)c(-c4ccc(F)c5sc(N)nc45)nc31)N1C[C@@H](C)NC[C@@H]1C(=O)N2C] | (2R,4aR)-10-(2-amino-7-fluorobenzo[d]thiazol-4-yl)-11-fluoro-8-(2-isopropyl-4-methylpyridin-3-yl)-2,6-dimethyl-2,3,4,4a,6,8-hexahydro-1H-pyrazino[1',2':4,5]pyrazino[2,3-c][1,8]naphthyridine-5,7-dione |
| 10d | 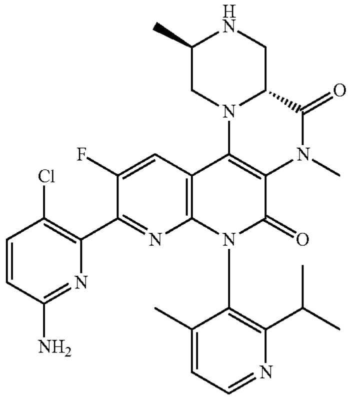 [SMILES: Cc1ccnc(C(C)C)c1-n1c(=O)c2c(c3cc(F)c(-c4nc(N)ccc4Cl)nc31)N1C[C@@H](C)NC[C@@H]1C(=O)N2C] | (2R,4aR)-10-(6-amino-3-chloropyridin-2-yl)-11-fluoro-8-(2-isopropyl-4-methylpyridin-3-yl)-2,6-dimethyl-2,3,4,4a,6,8-hexahydro-1H-pyrazino[1',2':4,5]pyrazino[2,3-c][1,8]naphthyridine-5,7-dione |

-continued

| Compound number | Structure | Name |
| --- | --- | --- |
| 11c | 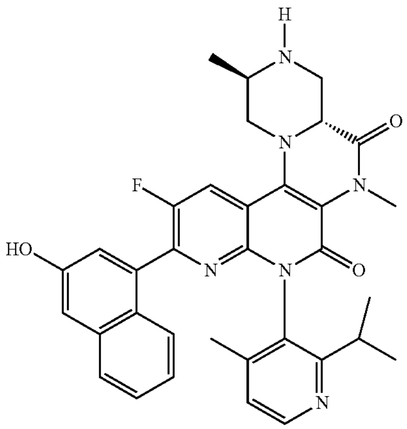 [SMILES: Cc1ccnc(C(C)C)c1-n1c(=O)c2c(c3cc(F)c(-c4cc(O)cc5ccccc45)nc31)N1C[C@@H](C)NC[C@@H]1C(=O)N2C] | (2R,4aR)-11-fluoro-10-(3-hydroxynaphthalen-1-yl)-8-(2-isopropyl-4-methylpyridin-3-yl)-2,6-dimethyl-2,3,4,4a,6,8-hexahydro-1H-pyrazino[1',2':4,5]pyrazino[2,3-c][1,8]naphthyridine-5,7-dione |
| 16n | 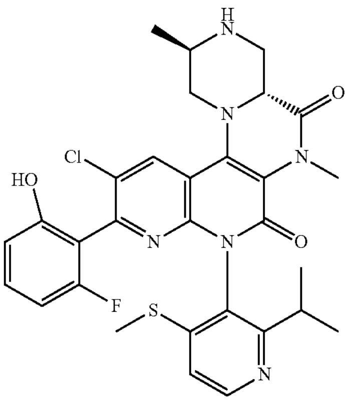 [SMILES: CSc1ccnc(C(C)C)c1-n1c(=O)c2c(c3cc(Cl)c(-c4c(O)cccc4F)nc31)N1C[C@@H](C)NC[C@@H]1C(=O)N2C] | (2R,4aR)-11-chloro-10-(2-fluoro-6-hydroxyphenyl)-8-(2-isopropyl-4-(methylthio)pyridin-3-yl)-2,6-dimethyl-2,3,4,4a,6,8-hexahydro-1H-pyrazino[1',2':4,5]pyrazino[2,3-c][1,8]naphthyridine-5,7-dione |

or a stereoisomer, tautomer, or pharmaceutically acceptable salt thereof.

In another aspect, the present disclosure provides a pharmaceutical composition, which comprises an effective dose of the compound represented by general formula (I), (II), (III), (IV), (V) or (VI), or the stereoisomer, tautomer, or pharmaceutically acceptable salt thereof, and an optional pharmaceutically acceptable carrier, excipient or a combination thereof.

In another aspect, the present disclosure provides a method for inhibiting K-Ras GTPase, comprising administering a pharmaceutical composition to a subject (including patients and healthy subjects), wherein the pharmaceutical composition comprises an effective dose of the compound represented by general formula (I), (II), (III), (IV), (V) or (VI), or the stereoisomer, tautomer, or pharmaceutically acceptable salt thereof, and an optional pharmaceutically acceptable carrier, excipient or a combination thereof, wherein the K-Ras GTPase is preferably KRAS G12C enzyme.

The present disclosure also provides use of the compound represented by general formula (I), (II), (III), (IV), (V) or (VI), or the stereoisomer, tautomer, or pharmaceutically acceptable salt thereof, or a pharmaceutically acceptable salt thereof in the manufacture of a medicament for treating a disease mediated by KRAS mutation, wherein the disease mediated by KRAS mutation is cancer, which is selected from the group consisting of pancreatic cancer, colorectal cancer, lung cancer, multiple myeloma, uterine cancer, cholangiocarcinoma, gastric cancer, bladder cancer, diffuse large B-cell lymphoma, rhabdomyosarcoma, squamous cell carcinoma, cervical cancer, and testicular germ cell carcinoma, preferably pancreatic cancer, colorectal cancer and lung cancer; wherein the lung cancer is preferably non-small cell lung cancer; wherein the KRAS mutation is preferably KRAS G12C mutation.

In another aspect, the present disclosure provides use of the compound represented by general formula (I), (II), (III), (IV), (V) or (VI), or the stereoisomer, tautomer, or pharmaceutically acceptable salt thereof, or a pharmaceutically acceptable salt thereof in the manufacture of a K-Ras GTPase inhibitor, wherein the K-Ras GTPase inhibitor is preferably a KRAS G12C inhibitor.

Another aspect of the present disclosure relates to a method for preventing and/or treating a disease mediated by KRAS mutation, comprising administering to a patient a therapeutically effective dose of the compound represented by general formula (I), (II), (III), (IV), (V) or (VI), or a tautomer, mesomer, racemate, enantiomer, or diastereoisomer thereof, or a mixture thereof, a pharmaceutically acceptable salt thereof or a pharmaceutical composition comprising the same, wherein the KRAS mutation is preferably a KRAS G12C mutation.

The present disclosure also provides use of the compound represented by general formula (I), (II), (III), (IV), (V) or (VI), or the stereoisomer, tautomer, or pharmaceutically acceptable salt thereof, or a pharmaceutically acceptable salt thereof in the manufacture of a medicament for treating cancer, wherein the cancer is selected from the group consisting of pancreatic cancer, colorectal cancer, lung cancer, multiple myeloma, uterine cancer, cholangiocarcinoma, gastric cancer, bladder cancer, diffuse large B-cell lymphoma, rhabdomyosarcoma, squamous cell carcinoma, cervical cancer, and testicular germ cell carcinoma, preferably pancreatic cancer, colorectal cancer and lung cancer; wherein the lung cancer is preferably non-small cell lung cancer.

The pharmaceutical formulation of the present disclosure can be administered topically, orally, transdermally, rectally, vaginally, parenterally, intranasally, intrapulmonarily, intraocularly, intravenously, intramuscularly, intraarterially, intrathecally, intravesicularly, intradermally, intraperitoneally, subcutaneously, subkeratinally or via inhalation. The pharmaceutical composition containing an active ingredient may be in a form suitable for oral administration, such as a tablet, a troche, a lozenge, an aqueous or oily suspension, dispersible powders or granules, an emulsion, a hard or soft capsule, a syrup or an elixir. The tablet may comprise an active ingredient and a non-toxic pharmaceutically acceptable excipient used for mixing that is suitable for the manufacture of a tablet.

The preparation of the present disclosure is suitably presented in unit dosage form and may be prepared by any of the methods well known in the art of pharmacy. An amount of the active ingredient in the single dosage form produced by combining with a carrier can vary depending upon the host treated and the particular mode of administration. The amount of the active ingredient in the single dosage form produced by combining with a carrier generally refers to an amount of a compound which produces a therapeutic effect.

A dosage form for the topical or transdermal administration of the compound of the present disclosure may include powders, a spray, an ointment, a paste, a cream, a lotion, a gel, a solution, a patch and an inhalant. The active compound can be mixed with a pharmaceutically acceptable carrier under an aseptic condition, and can be mixed with any preservatives, buffers or propellants that may be required.

When the compound of the present disclosure is administered to humans and animals in the form of medicine, the compound can be provided alone or in the form of a pharmaceutical composition. The pharmaceutical composition may comprise an active ingredient to be combined with a pharmaceutically acceptable carrier, such as 0.1% to 99.5% (more preferably, 0.5% to 90%) active ingredient.

Examples of pharmaceutically acceptable carriers include, but are not limited to: (1) sugars, such as lactose, glucose, and sucrose; (2) starches, such as corn starch and potato starch; (3) cellulose and its derivatives, such as sodium carboxymethyl cellulose, ethyl cellulose and cellulose acetate; (4) powdered gum tragacanth; (5) malt; (6) gelatin; (7) talc; (8) excipients, such as cocoa butter and suppository wax; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethanol; (20) phosphate buffer solutions; (21) cyclodextrin, such as a targeting ligand connecting to nanoparticles, such as Accurins™; and (22) other non-toxic compatible substances employed in pharmaceutical formulations, such as a polymer-based composition.

Examples of pharmaceutically acceptable antioxidants include, but are not limited to: (1) water-soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, α-tocopherol, and the like; and (3) metal chelating agents, such as citric acid, ethylenediamine tetraacetic acid (EDTA), sorbitol, tartaric acid, phosphoric acid, and the like. A solid dosage form (such as a capsule, a troche pill, a dragee, powders, granules, and the like) may comprise one or more pharmaceutically acceptable carriers such as sodium citrate or dicalcium phosphate, and/or any one selected from the group consisting of: (1) fillers or extenders, such as starch, lactose, sucrose, glucose, mannitol and/or silicic acid; (2) binders, such as carboxymethylcellulose, alginate, gelatin, polyvinyl pyrrolidone, sucrose, and/or gum arabic; (3) humectants, such as glycerin; (4) disintegrating agents, such as agar, calcium carbonate, potato starch or tapioca starch, alginic acid, certain silicate and sodium carbonate; (5) dissolution retarding agents, such as paraffin; (6) absorption accelerators, such as quaternary ammonium compounds; (7) wetting agents, such as cetyl alcohol and glycerol monostearate; (8) absorbents, such as kaolin and bentonite; (9) lubricants, such as talc, calcium stearate, magnesium stearate, solid polyethylene glycols, sodium lauryl sulfate, and a mixture thereof; and (10) coloring agents. A liquid dosage form may comprise a pharmaceutically acceptable emulsion, microemulsion, solution, suspension, syrup and elixir. In addition to the active ingredient, the liquid dosage form may comprise an inert diluting agent commonly used in the art, such as water or other solvents; a solubilizing agent and an emulsifying agent, such as ethanol, isopropanol, ethyl carbonate, ethyl acetate, benzyl alcohol, benzyl benzoate, propylene glycol, 1,3-butanediol, oils (especially cottonseed oil, peanut oil, corn oil, germ oil, olive oil, castor oil, and sesame oil), glycerin, tetrahydrofurfuryl alcohol, polyethylene glycols and fatty acid esters of sorbitan, and a mixture thereof.

In addition to the active compound, the suspension may further comprise a suspending agent such as ethoxylated isostearyl alcohols, polyoxyethylene sorbitol and sorbitan esters, microcrystalline cellulose, aluminum hydroxide oxide, bentonite, agar and tragacanth gum and a mixture thereof.

In addition to the active compound, the ointment, paste, cream and gel may further comprise an excipient such as animal and vegetable fats, oils, waxes, paraffins, starch, tragacanth gum, cellulose derivatives, polyethylene glycol, polysiloxane, bentonite, silicic acid, talc, zinc oxide or a mixture thereof.

In addition to the active compound, the powder and spray may further comprise an excipient such as lactose, talc, silicic acid, aluminum hydroxide, calcium silicate, polyamide powders, or a mixture thereof. The spray may comprise other common propellants, such as chlorofluorocarbon, and volatile unsubstituted hydrocarbon, such as butane and propane.

DETAILED DESCRIPTION OF THE INVENTION

Unless otherwise stated, some terms used in the specification and claims of the present disclosure are defined as follows:

"Chemical bond" means that the indicated substituent does not exist, and the two ends of the substituent are directly connected to form a bond.

"Alkyl" as a group or a part of a group refers to a $C_1$-$C_{20}$ straight chain or a branched aliphatic hydrocarbon group. It is preferably $C_1$-$C_{10}$ alkyl, more preferably $C_1$-$C_6$ alkyl, or $C_1$-$C_4$ alkyl. Examples of alkyl include, but are not limited to methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl and the like. Alkyl may be substituted or unsubstituted.

"Alkenyl" refers to alkyl as defined above consisting of at least two carbon atoms and at least one carbon-carbon double bond. Representative examples of alkenyl include but are not limited to ethenyl, 1-propenyl, 2-propenyl, 1-, 2- or 3-butenyl and the like. It is preferably $C_2$-$C_{10}$ alkenyl, more preferably $C_2$-$C_6$ alkenyl, most preferably $C_2$-$C_4$ alkenyl. Alkenyl may be optionally substituted or unsubstituted.

"Alkynyl" refers to an aliphatic hydrocarbon group containing one carbon-carbon triple bond, which may be straight or branched. It is preferably $C_2$-$C_{10}$ alkynyl, more preferably $C_2$-$C_6$ alkynyl, most preferably $C_2$-$C_4$ alkynyl. Examples of alkynyl include, but are not limited to ethynyl, 1-propynyl, 2-propynyl, 1-, 2-, or 3-butynyl, and the like. Alkynyl may be substituted or unsubstituted.

"Alkylene" is divalent alkyl. It is preferably $C_1$-$C_{10}$ alkylene, more preferably $C_1$-$C_6$ alkylene, and particularly preferably $C_1$-$C_4$ alkylene. Examples of alkylene include, but are not limited to methylene, ethylene, $-CH(CH_3)_2$, n-propylidene and the like. Alkylene may be substituted or unsubstituted.

"Cycloalkyl" refers to a saturated or partially saturated monocyclic, fused, bridged or spiro carbon ring. It is preferably $C_3$-$C_{12}$ cycloalkyl, more preferably $C_3$-$C_8$ cycloalkyl, and most preferably $C_3$-$C_6$ cycloalkyl. Examples of monocyclic cycloalkyl include, but are not limited to cyclopropyl, cyclobutyl, cyclopentyl, cyclopentenyl, cyclohexyl, cyclohexenyl, cyclohexadienyl, cycloheptyl, cycloheptatrienyl, cyclooctyl, and the like, preferably cyclopropyl and cyclohexenyl. Cycloalkyl may be optionally substituted or unsubstituted.

"Heterocyclyl", "heterocycle" and "heterocyclic" are used interchangeably in the present application and all refer to a non-aromatic heterocyclic group, where one or more atoms forming the ring are heteroatoms, such as oxygen, nitrogen and sulfur atoms, including a monocyclic ring, a fused ring, a bridged ring, and a spiro ring. It preferably has a 5 to 7 membered monocyclic ring or a 7 to 10 membered bi- or tricyclic ring, which may contain 1, 2 or 3 atoms selected from the group consisting of nitrogen, oxygen and sulfur. Examples of "heterocyclyl" include but are not limited to morpholinyl, oxetanyl, thiomorpholinyl, tetrahydropyranyl, 1,1-dioxothiomorpholinyl, piperidinyl, 2-oxopiperidinyl, pyrrolidinyl, 2-oxopyrrolidinyl, piperazin-2-one, 8-oxa-3-aza-bicyclo[3.2.1]octyl and piperazinyl. Heterocyclyl may be substituted or unsubstituted.

"Aryl" refers to a carbocyclic aromatic system containing one or two rings, wherein the rings may be fused together. The term "aryl" includes monocyclic or bicyclic aryl, such as an aromatic group of phenyl, naphthyl, or tetrahydronaphthyl. It is preferably $C_6$-$C_{10}$ aryl, more preferably phenyl and naphthyl. Aryl may be substituted or unsubstituted.

"Heteroaryl" refers to an aromatic 5 to 6 membered monocyclic ring or 8 to 10 membered bicyclic ring, which may contain 1 to 4 atoms selected from the group consisting of nitrogen, oxygen and sulfur. It is preferably bicyclic heteroaryl. Examples of "heteroaryl" include, but are not limited to the following: furanyl, pyridyl, 2-oxo-1,2-dihydropyridyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzodioxolyl, benzothienyl, benzimidazolyl, indolyl, isoindolyl, 1,3-dioxo-isoindolyl, quinolinyl, indazolyl, benzisothiazolyl, benzoxazolyl, benzisoxazolyl,

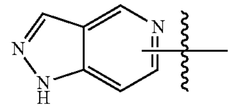
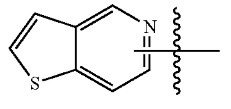
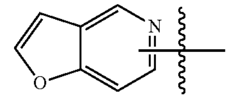
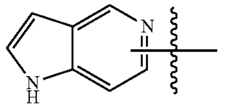
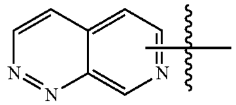
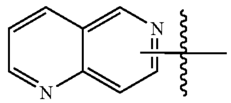
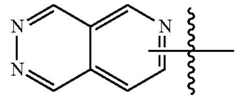
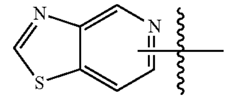
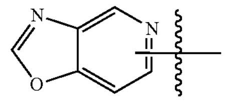
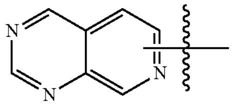
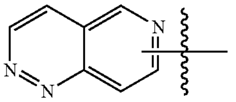
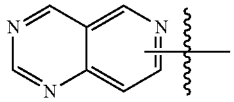
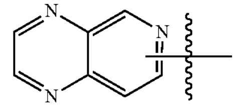
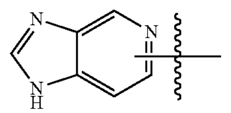
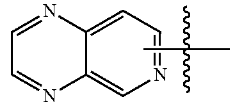
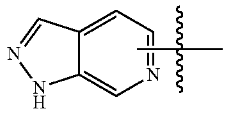
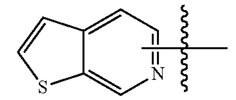
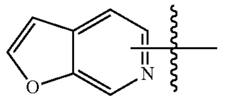
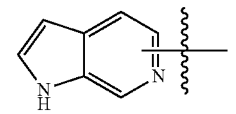
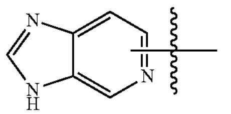
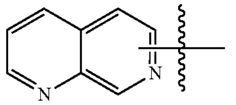
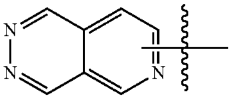
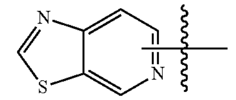
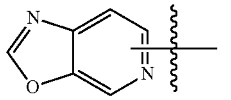
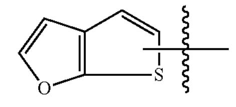
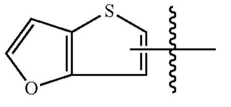

-continued

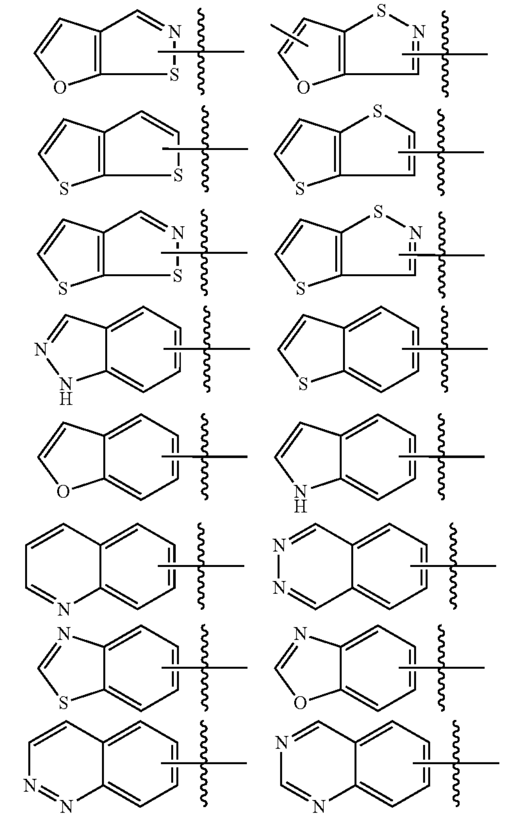

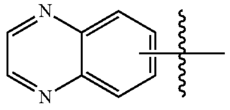

or

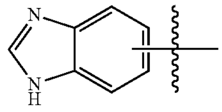

;

Heteroaryl May be Substituted or Unsubstituted.

"Fused ring" refers to a polycyclic group in which two or more cyclic structures share a pair of atoms with each other, wherein one or more rings may contain one or more double bonds, but at least one ring has no completely conjugated π-electron aromatic system, wherein the ring atoms are selected from 0, one or more heteroatoms selected from the group consisting of nitrogen, oxygen and $S(O)_r$ (where r is selected from 0, 1 or 2), and the rest ring atoms are carbon. The fused ring is preferably a bicyclic or tricyclic fused ring, wherein the bicyclic fused ring is preferably a fused ring of aryl or heteroaryl with a monocyclic heterocyclic group or a monocyclic cycloalkyl group. It is preferably 7 to 14 membered, more preferably 8 to 10 membered. Examples of "fused ring" include, but are not limited to:

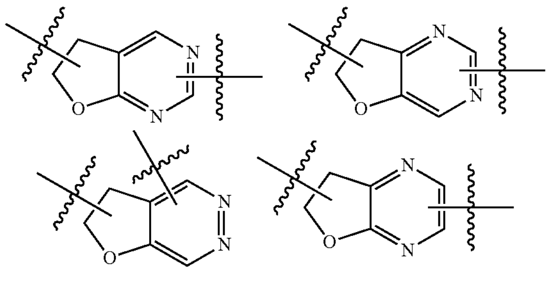

-continued

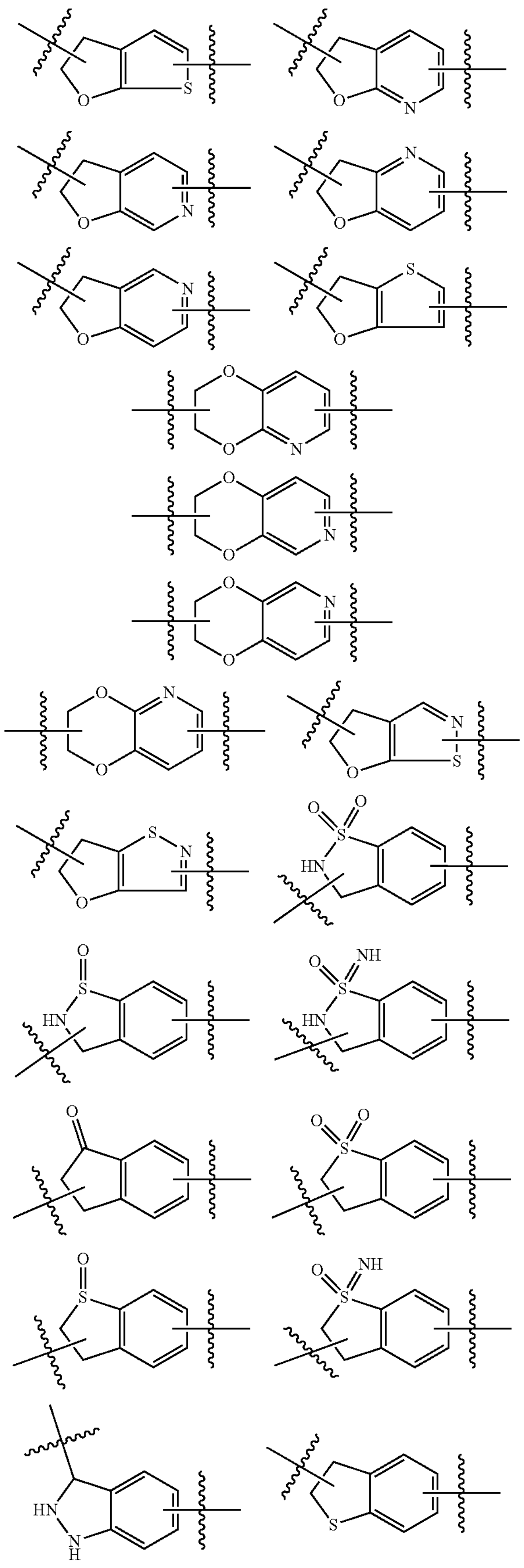

-continued

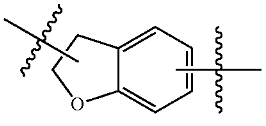
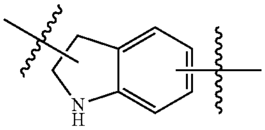
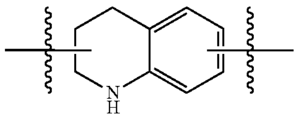
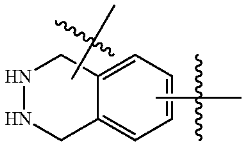
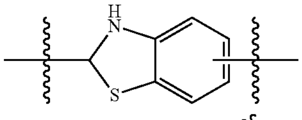
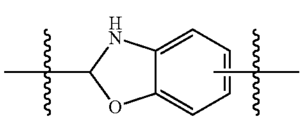
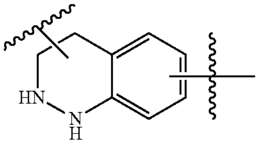
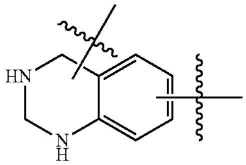
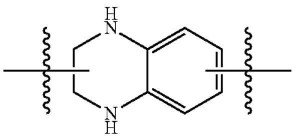
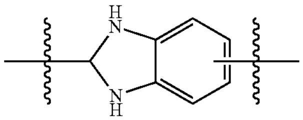
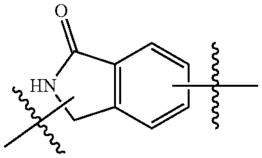
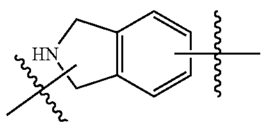
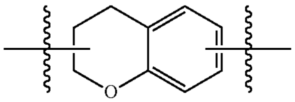
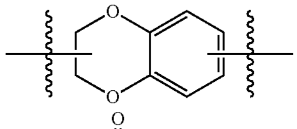
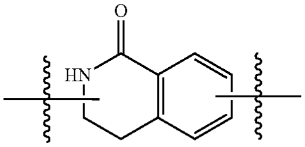
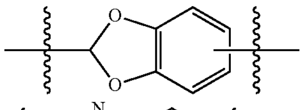
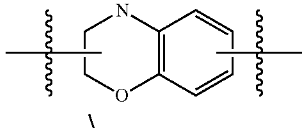

or

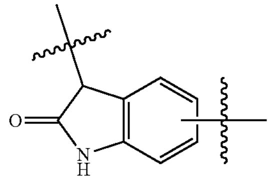

.

"Alkoxy" refers to a group of (alkyl-O—), wherein the alkyl is as defined herein. It is preferably $C_1$-$C_6$ and $C_1$-$C_4$ alkoxy. Examples of alkoxy include, but are not limited to: methoxy, ethoxy, n-propoxy, isopropoxy, n-butoxy, isobutoxy, tert-butoxy, and the like.

"Haloalkyl" refers to an alkyl group further optionally substituted with one or more halogens, wherein the alkyl is as defined herein.

"Deuterated alkyl" refers to an alkyl group further optionally substituted with one or more deuterium atoms, wherein the alkyl is as defined herein. "Deuterated alkyl" is preferably deuterated methyl, including: mono-, di- and tri-deuterated methyl, preferably tri-deuterated methyl.

"Hydroxyalkyl" refers to an alkyl group further optionally substituted with one or more hydroxyls, wherein the alkyl is as defined herein.

"Haloalkoxy" refers to an alkyl group of (alkyl-O—) further optionally substituted with one or more halogens, wherein alkoxy is as defined herein.

"Hydroxyl" refers to —OH.

"Halogen" refers to fluorine, chlorine, bromine and iodine.

"Amino" refers to $—NH_2$.

"Cyano" refers to —CN.

"Nitro" refers to $—NO_2$.

"Benzyl" refers to $—CH_2$-phenyl.

"Carboxyl" refers to —C(O)OH.

"Carboxylate" refers to —C(O)O-alkyl or —C(O)O-cycloalkyl, wherein alkyl and cycloalkyl are as defined above.

"DMSO" refers to dimethylsulfoxide.

"BOC" refers to tert-butoxycarbonyl.

"Ts" refers to p-toluenesulfonyl.

"T3P" refers to propylphosphoric anhydride.

"DPPA" refers to diphenylphosphoryl azide.

"DEA" refers to diethylamine.

"TFA" refers to trifluoroacetic acid.

"$CaCl_2$)" refers to calcium chloride.

"$MgCl_2$" refers to magnesium chloride.

"KCl" refers to potassium chloride.

"NaCl" refers to sodium chloride.

"Glucose" refers to glucose.

"HEPES" refers to N-2-hydroxyethylpiperazine-N'-2-ethanesulfonic acid.

"EGTA" refers to ethylene glycol bis(2-aminoethyl ether) tetraacetic acid.

"Substituted" means that one or more hydrogen atoms in a group, preferably up to 5, more preferably 1 to 3 hydrogen atoms are independently substituted by the corresponding number of substituents. Apparently, substituents are only in their possible chemical positions, and those skilled in the art can determine (by experiment or theory) possible or impossible substitutions without making too much effort. For example, an amino or hydroxyl group with free hydrogen may be unstable when binding to a carbon atom with an unsaturated (for example, olefinic) bond.

Unless otherwise specified, the "substitution" or "substituted" described herein means that a group can be substituted with one or more groups selected from the group consisting of: alkyl, alkenyl, alkynyl, alkoxy, alkylthio, alkylamino, halogen, sulfhydryl, hydroxyl, nitro, cyano, cycloalkyl, heterocyclyl, aryl, heteroaryl, cycloalkoxy, heterocycloalkoxy, cycloalkylthio, heterocycloalkylthio, amino, haloalkyl, hydroxyalkyl, carboxyl, carboxylate, =O, $—C(O)R^7$, $—C(O)OR^7$, $—NHC(O)R^7$, $—NHC(O)OR^7$, $—NR^8R^9$, $—C(O)NR^8R^9$, $—CH_2NHC(O)OR^7$, $—CH_2NR^8R^9$ and $—S(O)_rR^7$;

wherein, $R^7$ is selected from the group consisting of a hydrogen atom, alkyl, cycloalkyl, heterocyclyl, aryl and heteroaryl, wherein the alkyl, cycloalkyl, heterocyclyl, aryl or heteroaryl is further optionally substituted by one or more substituents selected from the group consisting of hydroxyl, halogen, nitro, cyano, alkyl, alkoxy, haloalkyl, haloalkoxy, cycloalkyl, heterocyclyl, aryl, heteroaryl, =O, —C(O)$R^{10}$, —C(O)$OR^{10}$, —OC(O)$R^{10}$, —$NR^{11}R^{12}$, —C(O)$NR^{11}R^{12}$, —$SO_2NR^{11}R^{12}$ and —NR C(O)$R^2$;

$R^8$ and $R^9$ are each independently selected from the group consisting of a hydrogen atom, hydroxyl, halogen, alkyl, alkoxy, cycloalkyl, heterocyclyl, aryl and heteroaryl, wherein the alkyl, alkoxy, cycloalkyl, heterocyclyl, aryl or heteroaryl is further optionally substituted by one or more substituents selected from the group consisting of hydroxyl, halogen, nitro, cyano, alkyl, alkoxy, cycloalkyl, heterocyclyl, aryl, heteroaryl, =O, —C(O)$R^{10}$, —C(O)$OR^{10}$, —OC(O)$R^{10}$, —$NR^{11}R^{12}$, —C(O)$NR^{11}R^{12}$, —$SO_2NR^{11}R^{12}$, and —$NR^{11}$C(O)$R^{12}$;

alternatively, $R^8$ and $R^9$ form a 4-8 membered heterocyclic group together with the atom they are connected to, wherein the 4-8 membered heterocyclic group contains one or more N, O or $S(O)_r$, and the 4-8 membered heterocyclic group is further optionally substituted by one or more substituents selected from the group consisting of hydroxyl, halogen, nitro, cyano, alkyl, alkoxy, cycloalkyl, heterocyclyl, aryl, heteroaryl, =O, —C(O)$R^{10}$, —C(O)$OR^{10}$, —OC(O)$R^{10}$, —$NR^{11}R^{12}$, —C(O)$NR^{11}R^{12}$, —$SO_2NR^{11}R^{12}$, and —$NR^{11}$C(O) $R^{12}$;

$R^{10}$, $R^{11}$ and $R^{12}$ are each independently selected from the group consisting of a hydrogen atom, alkyl, amino, cycloalkyl, heterocyclyl, aryl and heteroaryl, wherein the alkyl, cycloalkyl, heterocyclyl, aryl or heteroaryl is further optionally substituted by one or more substituents selected from the group consisting of hydroxyl, halogen, nitro, amino, cyano, alkyl, alkoxy, cycloalkyl, heterocyclyl, aryl, heteroaryl, carboxyl and carboxylate;

r is 0, 1 or 2.

The compounds of the present disclosure can contain asymmetric centers or chiral centers and thus exist in different stereoisomeric forms. It is expected that all stereoisomeric forms of the compounds of the present disclosure, including but not limited to diastereomers, enantiomers, atropisomers, geometric (conformational) isomers and a mixture thereof, such as a racemic mixture, are within the scope of the present disclosure.

Unless otherwise indicated, the structures described in the present disclosure also include all isomeric forms of such structures (for example, diastereoisomers, enantiomers, atropisomers, and geometric (conformational) isomers), for example, R and S configurations of each asymmetric center, (Z) and (E) double bond isomers, and (Z) and (E) conformational isomers. Therefore, an individual stereoisomer, a mixture of enantiomers, a mixture of diastereoisomers and a mixture of geometric (conformational) isomers of the compounds of the present disclosure are within the scope of the present disclosure.

"Pharmaceutically acceptable salt" refers to a certain salt of the above compound that can maintain the original biological activity and is suitable for medical use. The pharmaceutically acceptable salt of the compound represented by formula (I) may be a metal salt or an amine salt formed with a suitable acid.

"Pharmaceutical composition" refers to a mixture comprising one or more compounds described herein or a physiologically acceptable salt or a prodrug thereof with other chemical components and other optional components such as a physiologically acceptable carrier and excipient. The purpose of the pharmaceutical composition is to promote the administration to organisms, and facilitate the absorption of active ingredient, thus exerting biological activity.

Synthetic Method of the Compounds of the Present Disclosure

In order to accomplish the purpose of the present disclosure, the present disclosure adopts the following technical solution:

A method for producing the compound represented by general formula (I), or a stereoisomer, tautomer, or pharmaceutically acceptable salt thereof, comprising the following steps:

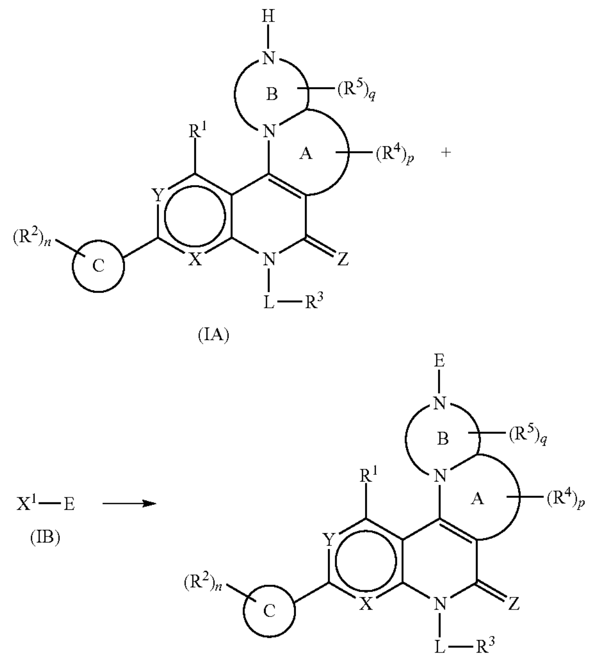

(IA) (IB) (I)

reacting a compound represented by general formula (IA) with a compound represented by general formula (IB) under a basic condition, and further optionally removing a protecting group to obtain the compound represented by general formula (I);

wherein:

$X^1$ is a leaving group, and is preferably chlorine;

ring A, ring B, ring C, $R^1$-$R^5$, X, Y, Z, E, L, n, p and q are as defined in general formula (I).

DETAILED DESCRIPTION

Figure 1:
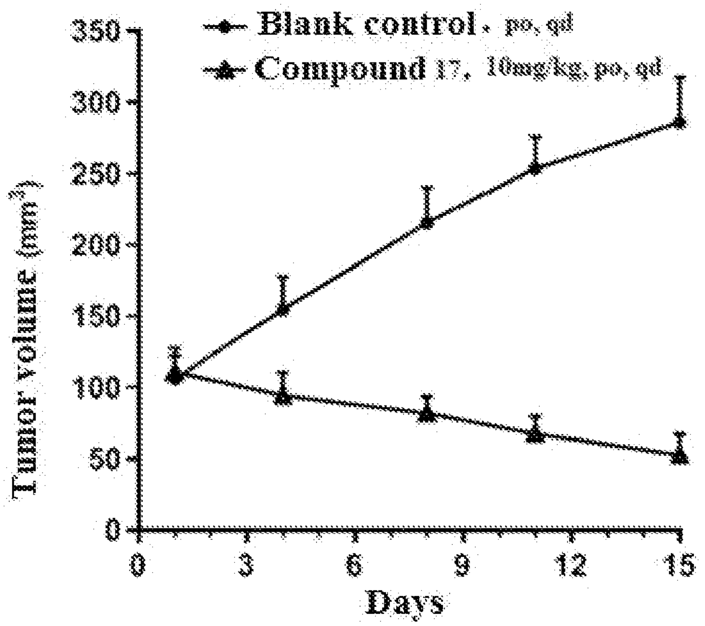
FIG. 1 shows the change in tumor volume of BALB/c nude mice with NCI-H358 cell xenograft tumor treated with the compound 17 of the present disclosure in Test Example 6.

The following examples are used to further describe the present disclosure, but these examples do not limit the scope of the present disclosure.

EXAMPLES

The examples provide the preparation of representative compounds represented by formula (I) and relevant structure identification data. It must be noted that the following examples are used to illustrate the present disclosure rather than limit the present disclosure. $^1$HNMR spectrum was measured by Bruker instrument (400 MHz), and the chemical shift is expressed in ppm. Tetramethylsilane was used as internal standard (0.00 ppm). $^1$HNMR is expressed as in a way of: s=singlet, d=doublet, t=triplet, m=multiplet, br=broadened, dd=doublet of doublet, and dt=doublet of triplet. The unit for a coupling constant provided is Hz.

Mass spectrum was measured by an LC/MS instrument, and ionization was carried out in a manner of ESI or APCI.

A Yantai Huanghai HSGF254 or Qingdao GF254 silica gel plate was used as a thin-layer chromatography silica gel plate. The silica gel plate used in thin-layer chromatography (TLC) has a specification of 0.15 mm-0.2 mm, and the silica gel plate used in thin-layer chromatography for separating and purifying products has a specification of 0.4 mm-0.5 mm.

In column chromatography, Yantai Huanghai 200-300 mesh silica gel was generally used as a carrier.

In the following examples, unless otherwise indicated, all temperatures are expressed in degree Celsius. Unless otherwise indicated, various starting materials and reagents were either commercially available or synthesized according to known methods, and commercially available materials and reagents were used directly without further purification. Unless otherwise specified, commercially available manufacturers include but are not limited to Shanghai Haohong Scientific Co., Ltd., Shanghai Accela ChemBio Co., Ltd., Shanghai Bide Pharmaceutical Technology Co., Ltd., Sa'en Chemistry Technology (Shanghai) Co., Ltd., Shanghai Lingkai Medicine Technology Co., Ltd., etc.

$CD_3OD$: deuterated methanol.

$CDCl_3$: deuterated chloroform.

DMSO-$d_6$: deuterated dimethyl sulfoxide.

In the examples, unless otherwise specified, the solution in the reaction refers to an aqueous solution.

The compounds were purified by column chromatography and thin layer chromatography using an eluent system, wherein the system is selected from the group consisting of: A: petroleum ether and ethyl acetate system; B: dichloromethane and methanol system; C: dichloromethane and ethyl acetate system; D: dichloromethane and ethanol system; E: tetrahydrofuran/petroleum ether system; F: tetrahydrofuran and methanol system; wherein the volume ratio of the solvents varies according to the polarity of the compound, and a small amount of acidic or alkaline reagents such as acetic acid, triethylamine, etc. can be added for adjustment.

Example 1—Compound 7

(2R,4aR)-3-acryloyl-10-(2-amino-7-fluorobenzo[d]thiazol-4-yl)-11-fluoro-8-(2-isoprop yl-4-methylpyridin-3-yl)-2,6-dimethyl-2,3,4,4a,6,8-hexahydro-1H-pyrazino[1',2':4,5]pyrazino[2, 3-c][1,8]naphthyridine-5,7-dione

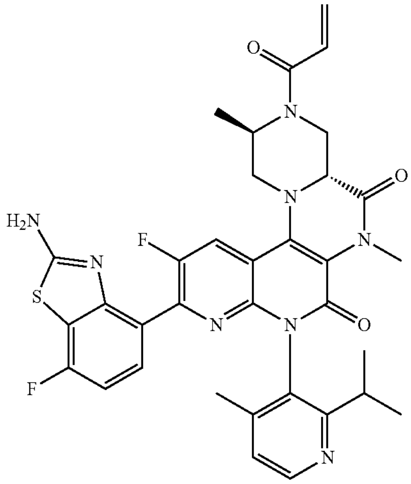

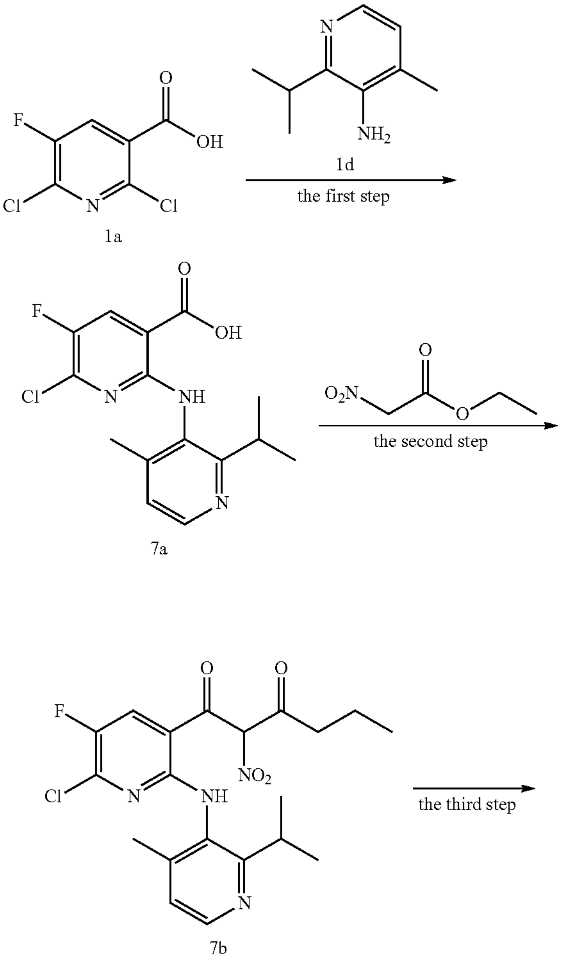

-continued
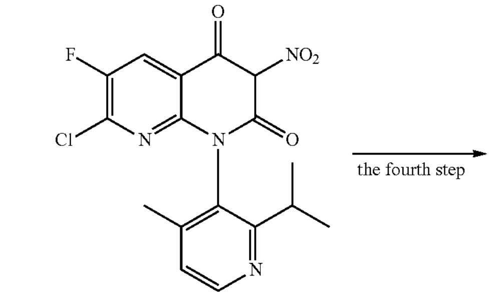
7c
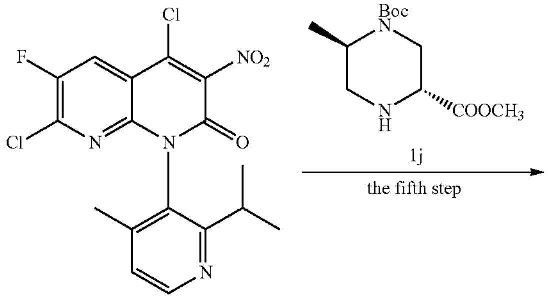
7d
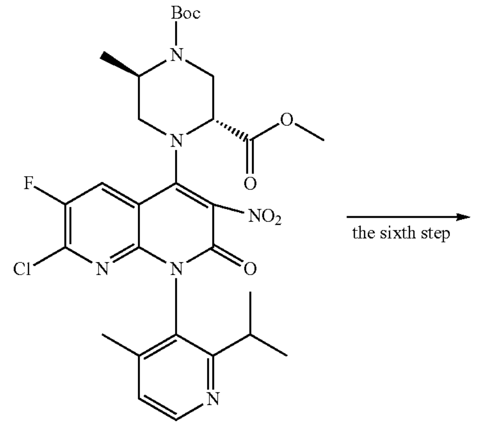
7e
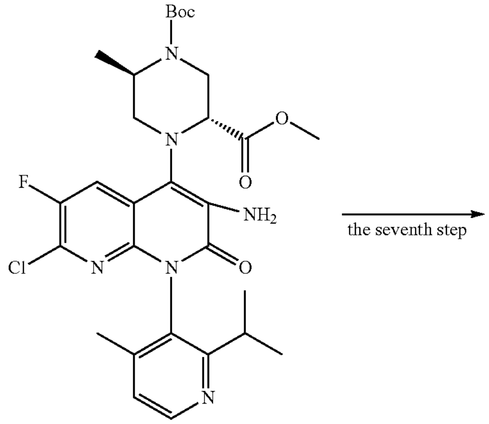
7f
-continued
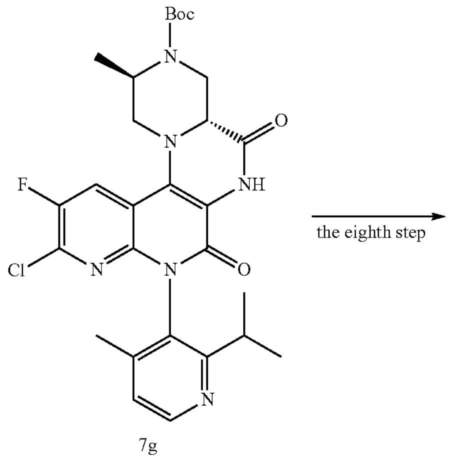
7g
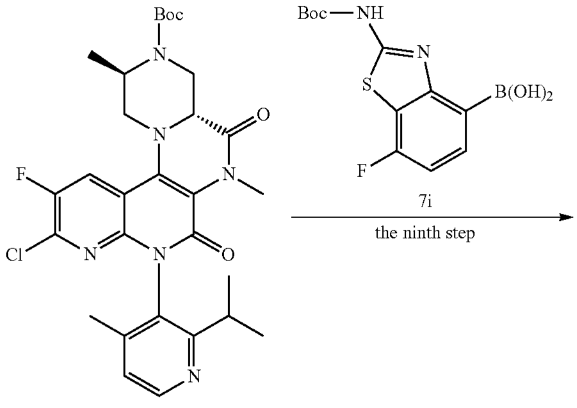
7h
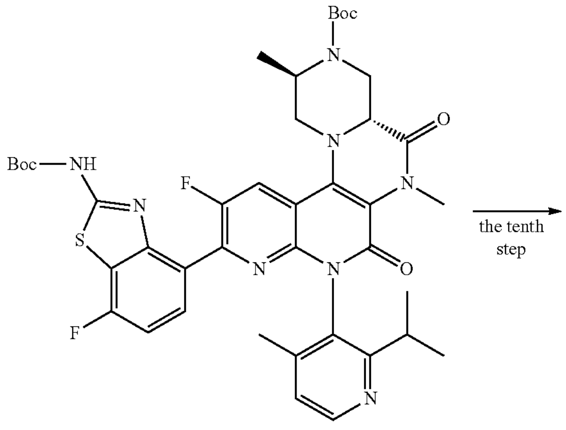
7j -continued

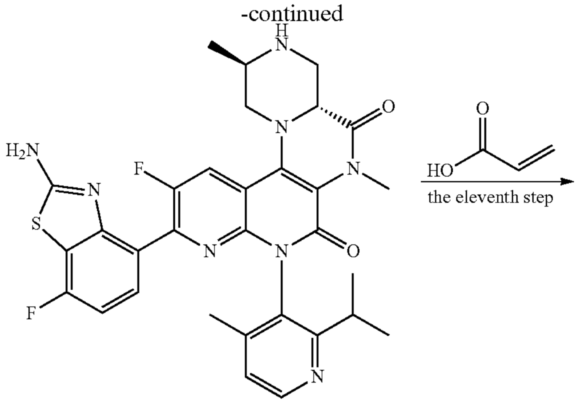

7k

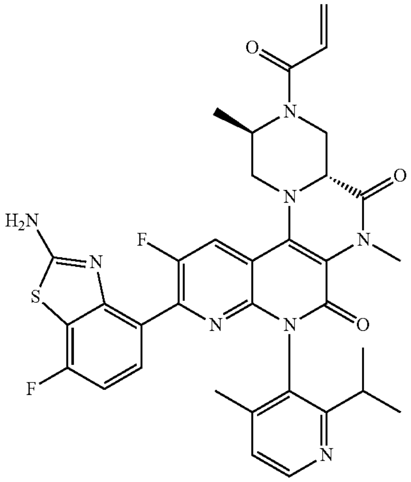

7

The First Step

6-Chloro-5-fluoro-2-((2-isopropyl-4-methylpyridin-3-yl)amino)nicotinic acid

2-Isopropyl-4-methylpyridin-3-amine 1d (21.46 g, 142.86 mmol) was dissolved in 200 mL of tetrahydrofuran, cooled down to −78° C., dropwise added with lithium bis(trimethylsilyl)amide (1.0 M, 238.11 mL) under nitrogen protection, then stirred at −78° C. for 15 mm, and dropwise added with a solution of 2,6-dichloro-5-fluoronicotinic acid 1a (20 g, 95.24 mmol) in tetrahydrofuran (100 mL) for 1 h of reaction at −78° C. followed by 3 h of reaction at 25° C. After the reaction was completed, the reaction solution was poured into 100 mL of ice water, and added with methyl tert-butyl ether (100 mL). The aqueous phase was adjusted to pH=4 with 2 M dilute hydrochloric acid for separation of layers, and the organic phase was dried over anhydrous sodium sulfate, then filtered, and concentrated under reduced pressure to obtain 6-chloro-5-fluoro-2-((2-isopropyl-4-methylpyridin-3-yl)amino)nicotinic acid 7a (15 g, 46.33 mmol) with a yield of 48.65%.

MS m/z(ESI): 323.8 $[M+1]^+$

The Second Step

Ethyl 3-(6-chloro-5-fluoro-2-((2-isopropyl-4-methylpyridin-3-yl)amino)pyridin-3-yl)-2-nitro-3-oxopropionate 6-Chloro-5-fluoro-2-((2-isopropyl-4-methylpyridin-3-yl)amino)nicotinic acid 7a (5 g, 15.44 mmol) was dissolved in N,N-dimethylformamide (50 mL), added with potassium carbonate (6.40 g, 46.33 mmol) and ethyl 2-nitroacetate (6.17 g, 46.33 mmol), and then added with 2-chloro-1-methylpyridine iodide (7.89 g, 30.89 mmol) for 3 h of reaction at 25° C. Then the reaction solution was added with 10 mL of ethyl acetate and 10 mL of saturated brine for separation of layers, and the organic phase was dried over anhydrous sodium sulfate, then filtered, and concentrated under reduced pressure. The obtained residue was separated and purified by flash silica gel column chromatography (eluent: system E) to obtain ethyl 3-(6-chloro-5-fluoro-2-((2-isopropyl-4-methylpyridin-3-yl)amino)pyridin-3-yl)-2-nitro-3-oxopro pionate 7b (2.3 g, 5.24 mmol) with a yield of 33.94%.

MS m/z(ESI): 438.9 $[M+1]^+$

The Third Step

7-Chloro-6-fluoro-1-(2-isopropyl-4-methylpyridin-3-yl)-3-nitro-1,8-naphthyridine-2,4(1H, 3H)-dione Ethyl 3-(6-chloro-5-fluoro-2-((2-isopropyl-4-methylpyridin-3-yl)amino)pyridin-3-yl)-2-nitro-3-oxopropionate 7b (2.3 g, 5.24 mmol) was dissolved in N,N-dimethylformamide (20 mL), and added with cesium carbonate (2.56 g, 7.86 mmol) for 16 h of reaction at 50° C. under stirring. After the reaction was completed, the reaction solution was cooled to 25° C., and added with 10 mL ethyl acetate and 10 mL saturated brine for separation of layers, and the organic phase was dried over anhydrous sodium sulfate, then filtered, and concentrated under reduced pressure. The obtained residue was separated and purified by flash silica gel column chromatography (eluent: system E-system F) to obtain 7-chloro-6-fluoro-1-(2-isopropyl-4-methylpyridin-3-yl)-3-nitro-1,8-naphthyridine-2,4(1H, 3H)-dione 7c (1.7 g, 4.33 mmol) with a yield of 82.58%.

MS m/z(ESI): 393.0 $[M+1]^+$

The Fourth Step 4,7-Dichloro-6-fluoro-1-(2-isopropyl-4-methylpyridin-3-yl)-3-nitro-1,8-naphthyridin-2(1H)-one 7-Chloro-6-fluoro-1-(2-isopropyl-4-methylpyridin-3-yl)-3-nitro-1,8-naphthyridine-2,4(1H, 3H)-dione 7c (400 mg, 1.02 mmol) was dissolved in phosphoryl chloride (3 mL) for 1 h of reaction at 90° C. The progress of the reaction was monitored by LC-MS. After the reaction was completed, the reaction solution was concentrated under reduced pressure. The obtained residue was separated and purified by flash silica gel column chromatography (eluent: E system) to obtain 4,7-dichloro-6-fluoro-1-(2-isopropyl-4-methylpyridin-3-yl)-3-nitro-1,8-naphthyridin-2 (1H)-one 7d (350 mg, 851.14 μmol) with a yield of 83.58%.

MS m/z(ESI): 410.8 $[M+1]^+$

The Fifth Step Methyl (3R,6R)-1-N-tert-butoxycarbonyl-4-(7-chloro-6-fluoro-1-(2-isopropyl-4-methylpyridin-3-yl)-3-nitro-2-oxo-1,2-dihydro-1,8-naphthyridin-4-yl)-6-methylpiperazine-3-carb oxylate 4,7-Dichloro-6-fluoro-1-(2-isopropyl-4-methylpyridin-3-yl)-3-nitro-1,8-naphthyridin-2 (1H)-one 7d (1.3 g, 3.16 mmol) was dissolved in acetonitrile (15 mL), and added with 1-(tert-butyl)-3-methyl(3R,6R)-6-methylpiperazine-1,3-dicarboxylate 1j (1.63 g, 6.32 mmol) for 16 h of reaction at 80° C. The progress of the reaction was monitored by LC-MS. After the reaction was completed, the reaction solution was concentrated under reduced pressure. The obtained residue was separated and purified by flash silica gel column chromatography (eluent: system E) to obtain methyl (3R,6R)-1-N-tert-butoxycarbonyl-4-(7-chloro-6-fluoro-1-(2-isopropyl-4-methylpyridin-3-yl)-3-nitro-2-oxo-1,2-dihydro-1,8-naphthyridin-4-yl)-6-methylpiperazine-3-c arboxylate 7e (1 g, 1.58 mmol) with a yield of 49.97%.

MS m/z(ESI): 633.0 $[M+1]^+$

The Sixth Step

Methyl (3R,6R)-1-N-tert-butoxycarbonyl-4-(3-amino-7-chloro-6-fluoro-1-(2-isopropyl-4-methylpyridin-3-yl)-2-oxo-1,2-dihydro-1,8-naphthyridin-4-yl)-6-methylpiperazine-3-carboxylate Methyl (3R,6R)-1-N-tert-butoxycarbonyl-4-(7-chloro-6-fluoro-1-(2-isopropyl-4-methylpyridin-3-yl)-3-nitro-2-oxo-1,2-dihydro-1,8-naphthyridin-4-yl)-6-methylpiperazine-3-carb oxylate 7e (1 g, 1.58 mmol) and Raney nickel (10 mg, 157.96 μmol) were dissolved in tetrahydrofuran (10 mL), and replaced with hydrogen three times for 2 h of reaction at 25° C. under the protection of hydrogen. Then the reaction solution was filtered, and the filtrate was concentrated under reduced pressure to obtain a crude product methyl (3R,6R)-1-N-tert-butoxycarbonyl-4-(3-amino-7-chloro-6-fluoro-1-(2-isopropyl-4-methylpyridin-3-yl)-2-oxo-1,2-di hydro-1,8-naphthyridin-4-yl)-6-methylpiperazine-3-carboxylate 7f (0.83 g, 1.38 mmol) with a yield of 87.13%, which was directly used in the next reaction.

MS m/z(ESI): 603.3 $[M+1]^+$

The Seventh Step

Tert-butyl (2R,4aR)-10-chloro-11-fluoro-8-(2-isopropyl-4-methylpyridin-3-yl)-2-methyl-5,7-dioxo-1,2,4,4a,5,6,7,8-octahydro-3H-pyrazino[1',2':4,5]pyrazino[2,3-c][1,8]naphthyr idine-3-carboxylate Methyl (3R,6R)-1-N-tert-butoxycarbonyl-4-(3-amino-7-chloro-6-fluoro-1-(2-isopropyl-4-methylpyridin-3-yl)-2-oxo-1,2-dihydro-1,8-naphthyridin-4-yl)-6-methylpiperazine-3-carboxyla the 7f (0.83 g, 1.38 mmol) and potassium carbonate (570.64 mg, 4.13 mmol) were dissolved in N,N-dimethylformamide (10 mL) for 1 h of reaction at 50° C. After the reaction was completed, the reaction solution was added with 10 mL of ethyl acetate and 10 mL of saturated brine for separation of layers, and the organic phase was dried over anhydrous sodium sulfate, then filtered, and concentrated under reduced pressure to obtain a crude product tert-butyl (2R,4aR)-10-chloro-11-fluoro-8-(2-isopropyl-4-methylpyridin-3-yl)-2-methyl-5,7-dioxo-1,2,4,4a,5,6,7,8-octahydro-3H-pyrazino[1',2':4,5]pyrazino[2,3-c][1,8]naphthyridine-3-carboxylate 7g (0.7 g, 1.23 mmol), which was then used directly in the next reaction.

MS m/z(ESI): 571.0$[M+1]^+$

The Eighth Step

Tert-butyl (2R,4aR)-10-chloro-11-fluoro-8-(2-isopropyl-4-methylpyridin-3-yl)-2,6-dimethyl-5,7-dioxo-1,2,4,4a,5,6,7,8-octahydro-3H-pyrazino[1',2':4,5]pyrazino[2,3-c][1,8]naphthyridine-3-carboxylate Tert-butyl (2R,4aR)-10-chloro-11-fluoro-8-(2-isopropyl-4-methylpyridin-3-yl)-2-methyl-5,7-dioxo-1,2,4,4a,5,6,7,8-octahydro-3H-pyrazino[1',2':4,5]pyrazino[2,3-c][1,8]naphthyr idine-3-carboxylate 7g (0.7 g, 1.23 mmol), iodomethane (521.98 mg, 3.68 mmol) and potassium carbonate (508.27 mg, 3.68 mmol) were dissolved in N,N-dimethylformamide (10 mL) for 16 h of reaction at 25° C. Then the reaction solution was added with 10 mL of ethyl acetate and 10 mL of water for separation of layers, and the organic phase was dried over anhydrous sodium sulfate, then filtered, and concentrated under reduced pressure. The obtained residue was separated and purified by flash silica gel column chromatography (eluent: system E) to obtain tert-butyl (2R,4aR)-10-chloro-11-fluoro-8-(2-isopropyl-4-methylpyridin-3-yl)-2,6-dimethyl-5,7-dioxo-1,2, 4,4a,5,6,7,8-octahydro-3H-pyrazino[1',2':4,5]pyrazino[2,3-c][1,8]naphthyridine-3-carboxylate 7h (0.45 g, 769.14 μmol) with a yield of 62.74%.

MS m/z(ESI): 585.0$[M+1]^+$

The Ninth Step

Tert-butyl (2R,4aR)-10-(2-((tert-butoxycarbonyl)amino)-7-fluorobenzo[d]thiazol-4-yl)-11-fluoro-8-(2-isopropyl-4-methylpyridin-3-yl)-2,6-dimethyl-5,7-dioxo-1,2,4,4a,5,6,7,8-octahydr o-3H-pyrazino[1',2':4,5]pyrazino[2,3-c][1,8]naphthyridine-3-carboxylate Tert-butyl (2R,4aR)-10-chloro-11-fluoro-8-(2-isopropyl-4-methylpyridin-3-yl)-2,6-dimethyl-5,7-dioxo-1,2,4,4a,5,6,7,8-octahydro-3H-pyrazino[1',2':4,5]pyrazino[2,3-c][1,8] naphth yridine-3-carboxylate 7h (0.12 g, 205.10 μmol), (2-((tert-butoxycarbonyl)amino)-7-fluorobenzo[d]thiazol-4-yl)boronic acid 7i (192.05 mg, 615.31 μmol), tetrakis(triphenylphosphine) palladium (23.70 mg, 20.51 μmol) and potassium phosphate (217.68 mg, 1.03 mmol) were dissolved in a mixed solvent of 0.2 mL of water and 1 mL of 1,4-dioxane, and replaced with nitrogen 3 times for 16 h of reaction at 100° C. under nitrogen atmosphere. The progress of the reaction was monitored by LC-MS. After the reaction was completed, the reaction solution was concentrated under reduced pressure. The obtained residue was separated and purified by flash silica gel column chromatography (eluent: system E) to obtain tert-butyl (2R,4aR)-10-(2-((tert-butoxycarbonyl)amino)-7-fluorobenzo[d]thiazol-4-yl)-11-fluoro-8-(2-isopropyl-4-methylpyridin-3-yl)-2,6-dimethyl-5,7-dioxo-1,2,4,4a,5,6,7,8-octahydro-3H-pyrazino[1',2':4,5] pyrazino[2,3-c][1, 8]naphthyridine-3-carboxylate 7j (0.1 g, 122.41 μmol) with a yield of 59.68%.

MS m/z(ESI): 817.4 [M+1]$^+$

The Tenth Step (2R,4aR)-10-(2-amino-7-fluorobenzo[d]thiazol-4-yl)-11-fluoro-8-(2-isopropyl-4-methylpyridin-3-yl)-2,6-dimethyl-2,3,4,4a,6,8-hexahydro-1H-pyrazino [1',2':4,5]pyrazino[2,3-c][1,8]naphthyridi ne-5,7-dione Tert-butyl (2R,4aR)-10-(2-((tert-butoxycarbonyl)amino)-7-fluorobenzo[d]thiazol-4-yl)-11-fluoro-8-(2-isopropyl-4-methylpyridin-3-yl)-2,6-dimethyl-5,7-dioxo-1,2,4,4a,5,6,7,8-octahydr o-3H-pyrazino[1',2':4,5]pyrazino[2,3-c][1,8] naphthyridine-3-carboxylate 7j (0.1 g, 122.41 μmol) was dissolved in dichloromethane (2 mL), and added with trifluoroacetic acid (300 mg, 2.63 mmol) for 16 h of reaction at 20° C. Then the reaction solution was concentrated under reduced pressure to obtain a crude product (2R,4aR)-10-(2-amino-7-fluorobenzo[d]thiazol-4-yl)-11-fluoro-8-(2-isopropyl-4-methylpyridin-3-yl)-2,6-dimethyl-2,3,4,4a,6,8-hexahydro-1H-pyrazin o[1',2':4,5]pyrazino[2,3-c][1,8] naphthyridine-5,7-dione 7k (100 mg, 136.85 μmol), which was then directly used in the next reaction.

MS m/z (ESI): 617.5 [M+1]$^+$

The Eleventh Step (2R,4aR)-3-acryloyl-10-(2-amino-7-fluorobenzo[d] thiazol-4-yl)-11-fluoro-8-(2-isopropyl-4-meth ylpyridin-3-yl)-2,6-dimethyl-2,3,4,4a,6,8-hexahydro-1H-pyrazino[1',2':4,5]pyrazino[2,3-c][1,8]n aphthy-ridine-5,7-dione Acrylic acid (18.33 mg, 254.41 μmol), (2R,4aR)-10-(2-amino-7-fluorobenzo[d]thiazol-4-yl)-11-fluoro-8-(2-isopropyl-4-methylpyridin-3-yl)-2,6-dimethyl-2,3,4,4a,6,8-hexahydro-1H-py razino[1',2':4,5]pyrazino[2,3-c][1,8] naphthyridine-5,7-dione 7k (110 mg, 150.54 μmol) and N,N-diisopropylethylamine (194.56 mg, 1.51 mmol) were dissolved in acetonitrile (1 mL), and added with propylphosphoric anhydride (191.59 mg, 301.08 μmol, 50% purity) for 16 h of reaction at 25° C. After the reaction was completed, the reaction solution was added with 20 mL of water, and extracted with ethyl acetate (20 mL×2). The organic phases were combined, dried over anhydrous magnesium sulfate, filtered, and concentrated under reduced pressure. The obtained residue was separated and purified by preparative liquid chromatography (separation column: Boston Prime C18, 150×30 mm I.D., 5 μm; mobile phase A: water (0.05% $NH_3H_2O$+10 mM $NH_4HCO_3$), mobile phase B: acetonitrile; flow rate: 25 mL/min) to obtain (2R,4aR)-3-acryloyl-10-(2-amino-7-fluorobenzo[d]thiazol-4-yl)-11-fluoro-8-(2-isopropyl-4-meth ylpyridin-3-yl)-2,6-dimethyl-2,3,4,4a,6,8-hexahydro-1H-pyrazino[1',2':4,5]pyrazino[2,3-c][1,8]n aphthyridine-5,7-dione 7 (30 mg).

MS m/z (ESI): 671.1 [M+1]$^+$

Example 2—Compound 8 and Compound 9

(2R,4aR,8R)-3-acryloyl-10-(2-amino-7-fluorobenzo [d]thiazol-4-yl)-11-fluoro-8-(2-isopropyl-4-m ethylpyridin-3-yl)-2,6-dimethyl-2,3,4,4a,6,8-hexahydro-1H-pyrazino[1',2':4,5]pyrazino[2,3-c][1, 8]naphthyridine-5,7-dione 8

(2R,4aR,8S)-3-acryloyl-10-(2-amino-7-fluorobenzo [d]thiazol-4-yl)-11-fluoro-8-(2-isopropyl-4-m ethylpyridin-3-yl)-2,6-dimethyl-2,3,4,4a,6,8-hexahydro-1H-pyrazino[1',2':4,5]pyrazino[2,3-c][1, 8]naphthyridine-5,7-dione 9

8

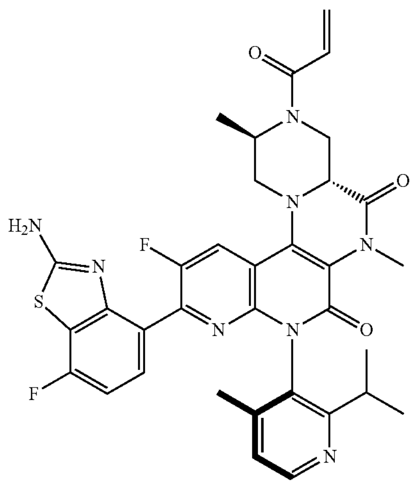

9

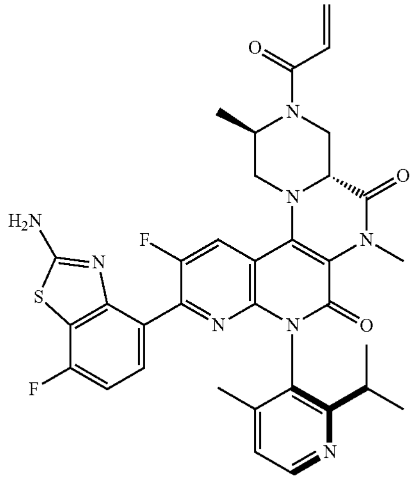

-continued

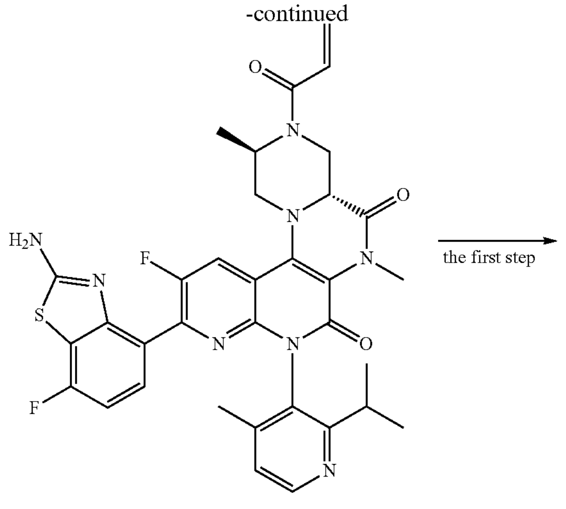

7

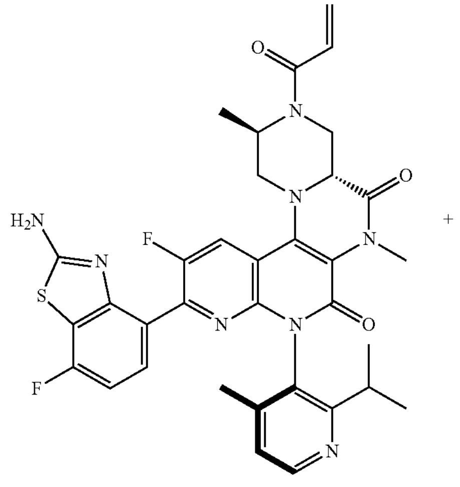

+

8

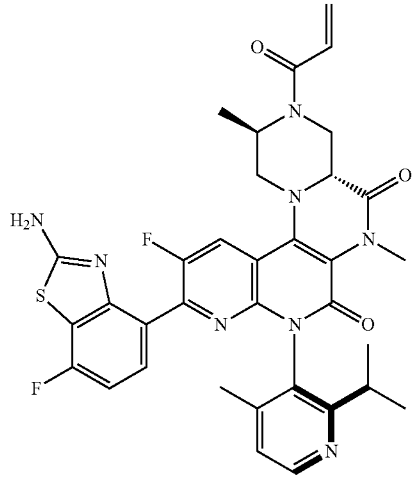

9

(2R,4aR)-3-acryloyl-10-(2-amino-7-fluorobenzo[d]thiazol-4-yl)-11-fluoro-8-(2-isoprop yl-4-methylpyridin-3-yl)-2,6-dimethyl-2,3,4,4a,6,8-hexahydro-1H-pyrazino[1',2':4,5] pyrazino[2, 3-c][1,8]naphthyridine-5,7-dione 7 (30 mg) was chirally resolved by preparative SFC (column type: (s,s) WHELK-01, 250×30 mm I.D., 5 μm; mobile phase: A for $CO_2$ and B for EtOH (0.1% $NH_3H_2O$); column pressure: 100 bar; flow rate: 70 mL/min; detection wavelength: 220 nm; column temperature: 40° C.). Then purification was performed to obtain a compound 8 with a single configuration (with a shorter retention time) and a compound 9 with a single configuration (with a longer retention time).

Compound 8 with a single configuration (with a shorter retention time):

MS m/z(ESI): 671.1 [M+1]$^+$ 2.05 mg; retention time: 3.446 min; chiral purity: 100% ee.

$^1$H NMR (400 MHz, DMSO-$d_6$) δ 8.46 (d, J=4.9 Hz, 1H), 8.02-7.83 (m, 3H), 7.25 (d, J=4.9 Hz, 1H), 7.10-6.80 (m, 3H), 6.24-6.08 (m, 1H), 5.82-5.69 (m, 1H), 5.17-4.37 (m, 2H), 4.08-3.92 (m, 1H), 3.75 (br dd, J=3.9, 13.8 Hz, 1H), 3.34 (s, 3H), 3.02-2.71 (m, 3H), 1.83 (s, 3H), 1.62-1.45 (m, 3H), 1.11 (br d, J=6.6 Hz, 3H), 0.99 (br d, J=6.5 Hz, 3H).

Compound 9 with a single configuration (with a longer retention time):

MS m/z(ESI): 671.1 [M+1]$^+$ 9.35 mg; retention time: 4.235 min; chiral purity: 100% ee.

$^1$H NMR (400 MHz, DMSO-d6) δ 8.47 (d, J=4.8 Hz, 1H), 8.00-7.87 (m, 3H), 7.25 (d, J=4.9 Hz, 1H), 7.09-6.83 (m, 3H), 6.23-6.09 (m, 1H), 5.76-5.69 (m, 1H), 5.10-4.42 (m, 2H), 4.13-3.96 (m, 1H), 3.75 (dd, J=4.0, 14.0 Hz, 1H), 3.37 (s, 3H), 3.32-3.22 (m, 2H), 2.99-2.77 (m, 1H), 2.00 (s, 3H), 1.60-1.51 (m, 3H), 1.05 (br d, J=6.6 Hz, 3H), 0.92 (br d, J=6.6 Hz, 3H).

Example 3—Compound 10

(2R,4aR)-3-acryloyl-10-(6-amino-3-chloropyridin-2-yl)-11-fluoro-8-(2-isopropyl-4-methylpyridi n-3-yl)-2,6-dimethyl-2,3,4,4a,6,8-hexahydro-1H-pyrazino [1',2':4,5]pyrazino[2,3-c][1,8]naphthyr idine-5,7-dione

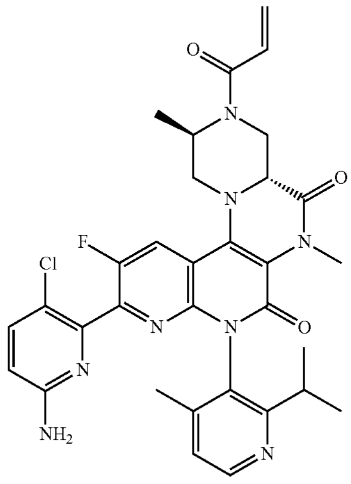

-continued

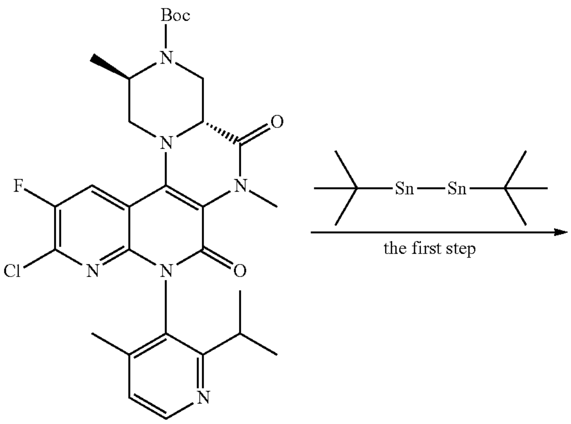

7h

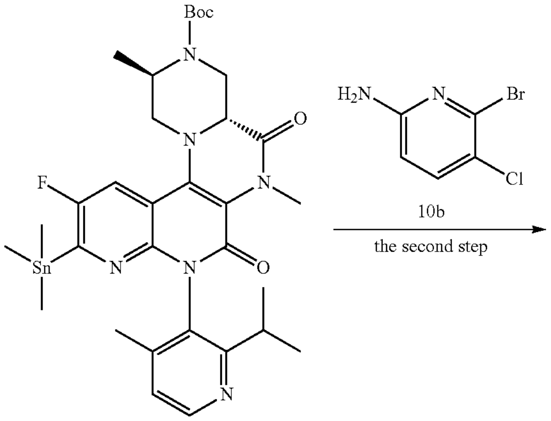

10a

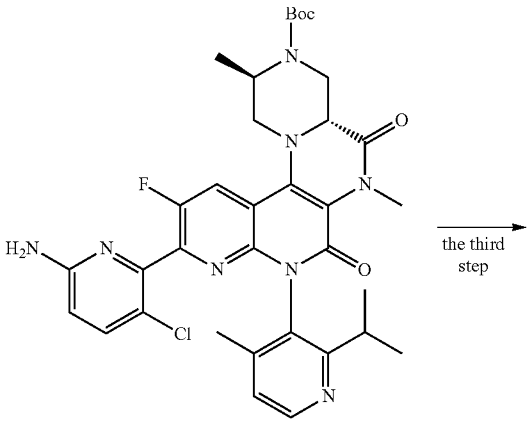

10c

-continued

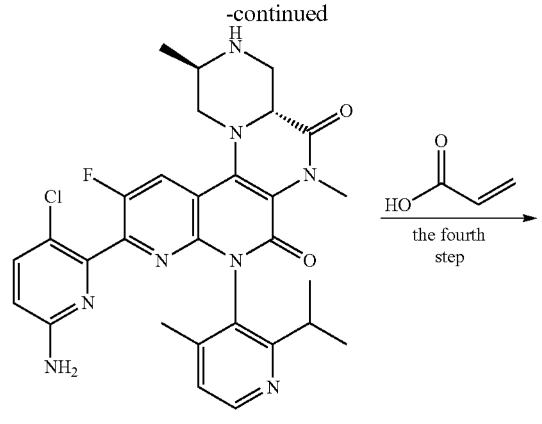

10d

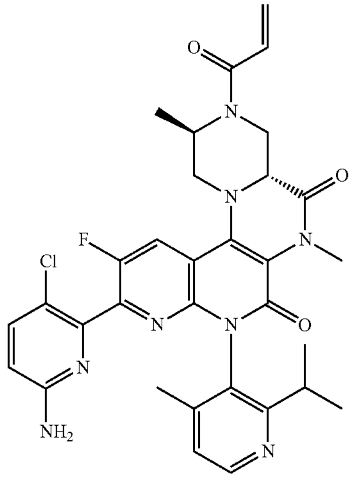

10

The First Step

Tert-butyl (2R,4aR)-11-fluoro-8-(2-isopropyl-4-methylpyridin-3-yl)-2,6-dimethyl-5,7-dioxo-10-(trimethylstannyl)-1,2,4,4a,5,6,7,8-octahydro-3H-pyrazino[1',2':4,5]pyrazino[2,3-c][1,8]naphthyridine-3-carboxylate Tert-butyl (2R,4aR)-10-chloro-11-fluoro-8-(2-isopropyl-4-methylpyridin-3-yl)-2,6-dimethyl-5,7-dioxo-1,2,4,4a,5,6,7,8-octahydro-3H-pyrazino[1',2':4,5]pyrazino[2,3-c][1,8] naphth yridine-3-carboxylate 7h (0.1 g, 170.92 μmol), hexamethylditin (139.99 mg, 427.30 μmol) and tetrakis (triphenylphosphine)palladium (19.75 mg, 17.09 μmol) were dissolved in 1,4-dioxane (1 mL), and replaced with nitrogen three times for 16 h of reaction at 110° C. under nitrogen atmosphere. Then the reaction solution was concentrated under reduced pressure. The obtained residue was separated and purified by flash silica gel column chromatography (eluent: system E) to obtain tert-butyl (2R,4aR)-11-fluoro-8-(2-isopropyl-4-methylpyridin-3-yl)-2,6-dimethyl-5,7-dioxo-10-(trimethylstannyl)-1,2,4,4a,5,6,7,8-octahydro-3H-pyrazino[1',2':4,5]pyrazino[2,3-c][1,8] naphthyridine-3-carboxylate 10a (95 mg, 133.16 μmol) with a yield of 77.91%.

MS m/z(ESI): 714.8[M+1]$^+$

The Second Step

Tert-butyl (2R,4aR)-10-(6-amino-3-chloropyridin-2-yl)-11-fluoro-8-(2-isopropyl-4-methylpyridin-3-yl)-2,6-dimethyl-5,7-dioxo-1,2,4,4a,5,6,7,8-octahydro-3H-pyrazino[1',2':4,5]py razino[2,3-c][1,8]naphthyridine-3-carboxylate Tert-butyl (2R,4aR)-11-fluoro-8-(2-isopropyl-4-methylpyridin-3-yl)-2,6-dimethyl-5,7-dioxo-10-(trimethylstannyl)-1,2,4,4a,5,6,7,8-octahydro-3H-pyrazino[1',2':4,5]pyrazino[2,3-c][1,8]naphthyridine-3-carboxylate 10a (40 mg, 56.07 μmol), 6-bromo-5-chloropyridin-2-amine 10b (13.96 mg, 67.28 μmol), cuprous iodide (1.07 mg, 5.61 μmol) and tetrakis(triphenylphosphine)palladium (3.24 mg, 2.80 μmol) were dissolved in 1,4-dioxane (0.5 mL), and replaced with nitrogen three times for 16 h of reaction at 100° C. under nitrogen atmosphere. Then the reaction solution was concentrated under reduced pressure. The obtained residue was separated and purified by flash silica gel column chromatography (eluent: system E) to obtain tert-butyl (2R,4aR)-10-(6-amino-3-chloropyridin-2-yl)-11-fluoro-8-(2-isopropyl-4-methylpyridin-3-yl)-2,6-dimethyl-5,7-dioxo-1,2,4,4a,5,6,7,8-octahydro-3H-pyrazino[1',2':4,5]py razino[2,3-c][1,8]naphthyridine-3-carboxylate 10c (15 mg, 22.15 μmol) with a yield of 39.51%.

MS m/z(ESI): 677.3[M+1]$^+$

The Third Step (2R,4aR)-10-(6-amino-3-chloropyridin-2-yl)-11-fluoro-8-(2-isopropyl-4-methylpyridin-3-yl)-2,6-dimethyl-2,3,4,4a,6,8-hexahydro-1H-pyrazino[1',2':4,5]pyrazino[2,3-c][1,8]naphthyridine-5,7-di one Tert-butyl (2R,4aR)-10-(6-amino-3-chloropyridin-2-yl)-11-fluoro-8-(2-isopropyl-4-methylpyridin-3-yl)-2,6-dimethyl-5,7-dioxo-1,2,4,4a,5,6,7,8-octahydro-3H-pyrazino[1',2':4,5]py razino[2,3-c][1,8]naphthyridine-3-carboxylate 10c (30 mg, 44.30 μmol) was dissolved in dichloromethane (3 mL), and added with trifluoroacetic acid (1 g, 8.77 mmol) for 16 h of reaction at 20° C. Then the reaction solution was concentrated under reduced pressure to obtain a crude product (2R,4aR)-10-(6-amino-3-chloropyridin-2-yl)-11-fluoro-8-(2-isopropyl-4-methylpyridin-3-yl)-2,6-dimethyl-2,3,4,4a,6,8-hexahydro-1H-pyrazino[1',2':4,5]pyrazino[2,3-c][1,8]naphthyridine-5,7-dione 10d (30 mg, 51.99 μmol), which was then directly used in the next reaction.

MS m/z(ESI): 577.0 [M+1]$^+$

The Fourth Step (2R,4aR)-3-acryloyl-10-(6-amino-3-chloropyridin-2-yl)-11-fluoro-8-(2-isopropyl-4-methylpyridi n-3-yl)-2,6-dimethyl-2,3,4,4a,6,8-hexahydro-1H-pyrazino[1',2':4,5]pyrazino[2,3-c][1,8]naphthyr idine-5,7-dione Acrylic acid (4.41 mg, 61.14 μmol), (2R,4aR)-10-(6-amino-3-chloropyridin-2-yl)-11-fluoro-8-(2-isopropyl-4-methylpyridin-3-yl)-2,6-dimethyl-2,3,4,4a,6,8-hexahydro-1H-pyrazin o[1',2':4,5]pyrazino[2,3-c][1,8]naphthyridine-5,7-dione 10d (25 mg, 36.18 μmol) and N,N-diisopropylethylamine (46.75 mg, 361.76 μmol) were dissolved in acetonitrile (5 mL), and added with propylphosphoric anhydride (46.04 mg, 72.35 μmol, 50% purity) for 16 h of reaction at 25° C. After the reaction was completed, the reaction solution was added with 20 mL of water, and extracted with ethyl acetate (20 mL×2). The organic phases were combined, dried over anhydrous magnesium sulfate, filtered, and concentrated under reduced pressure. The obtained residue was separated and purified by preparative liquid chromatography (separation column: Boston Prime C18, 150×30 mm I.D., 5 μm; mobile phase A: water (0.05% $NH_3H_2O$+10 mM $NH_4HCO_3$), mobile phase B: acetonitrile; flow rate: 25 mL/min) to obtain (2R,4aR)-3-acryloyl-10-(6-amino-3-chloropyridin-2-yl)-11-fluoro-8-(2-isopropyl-4-methylpyridi n-3-yl)-2,6-dimethyl-2,3,4,4a,6,8-hexahydro-1H-pyrazino[1',2':4,5]pyrazino[2,3-c][1,8]naphthyr idine-5,7-dione 10 (13 mg, 20.60 μmol) with a yield of 56.94%.

MS m/z (ESI): 631.4[M+1]$^+$ $^1$H NMR (400 MHz, DMSO-$d_6$) δ 8.46 (dd, J=2.3, 4.8 Hz, 1H), 8.09-7.99 (m, 1H), 7.49 (d, J=8.8 Hz, 1H), 7.26 (dd, J=4.9, 12.3 Hz, 1H), 7.10-6.80 (m, 1H), 6.52 (d, J=8.9 Hz, 1H), 6.33 (br s, 2H), 6.22-6.11 (m, 1H), 5.83-5.70 (m, 1H), 5.10-4.29 (m, 2H), 4.09-3.92 (m, 1H), 3.74 (dd, J=4.0, 14.1 Hz, 1H), 3.3-3.33 (m, 3H), 2.97-2.72 (m, 2H), 2.46-2.36 (m, 1H), 2.04-1.75 (m, 3H), 1.61-1.49 (m, 3H), 1.14-0.83 (m, 6H).

Example 4—Compound 11

(2R,4aR)-3-acryloyl-11-fluoro-10-(3-hydroxynaphthalen-1-yl)-8-(2-isopropyl-4-methylpyridin-3-yl)-2,6-dimethyl-2,3,4,4a,6,8-hexahydro-1H-pyrazino[1',2':4,5]pyrazino[2,3-c][1,8]naphthyridin e-5,7-dione

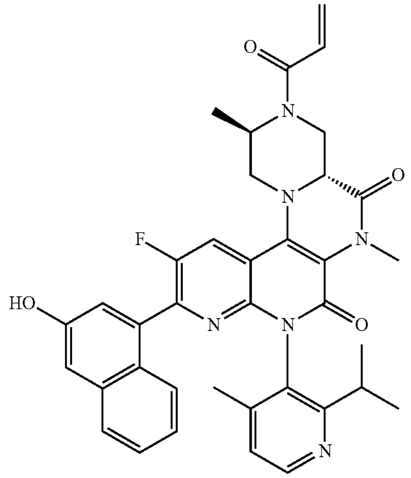

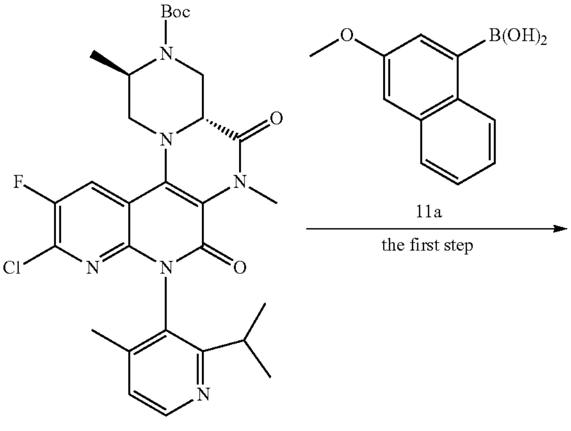

7h

-continued

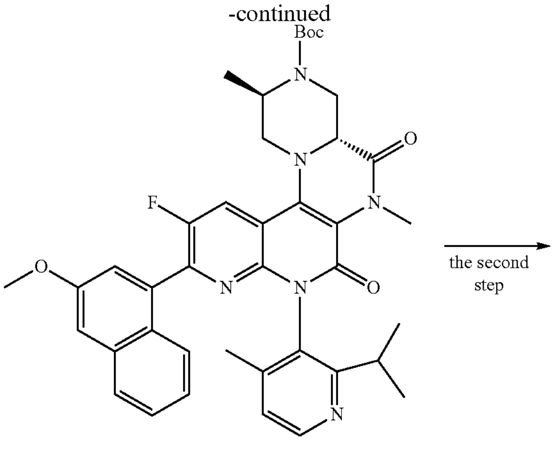

11b

-continued

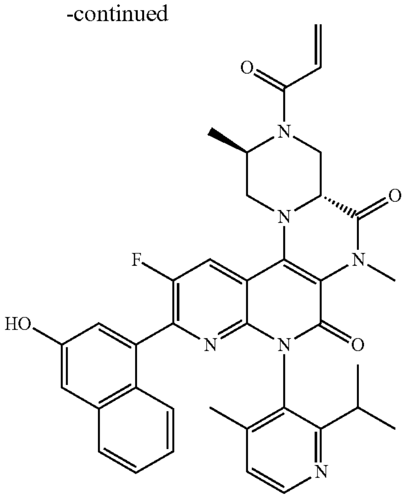

11

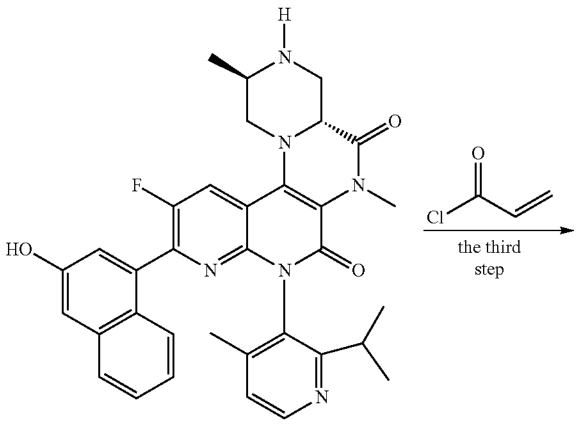

11c

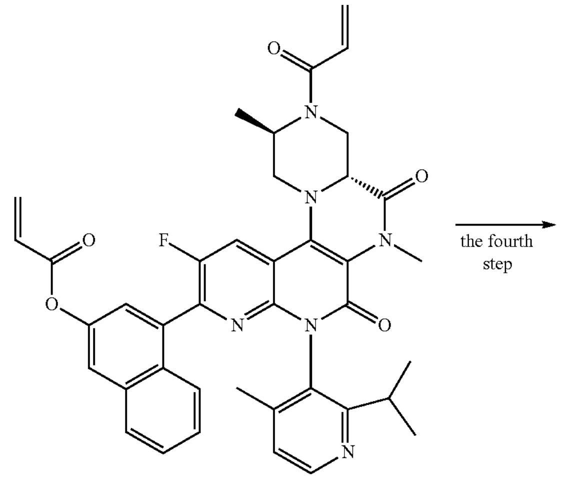

11d

The First Step

Tert-butyl (2R,4aR)-11-fluoro-8-(2-isopropyl-4-methylpyridin-3-yl)-10-(3-methoxynaphthalen-1-yl)-2,6-dimethyl-5,7-dioxo-1,2,4,4a,5,6,7,8-octahydro-3H-pyrazino[1',2':4, 5]pyrazino[2,3-c][1,8]naphthyridine-3-carboxylate Tert-butyl (2R,4aR)-10-chloro-11-fluoro-8-(2-isopropyl-4-methylpyridin-3-yl)-2,6-dimethyl-5,7-dioxo-1,2,4,4a,5,6,7,8-octahydro-3H-pyrazino[1',2':4,5]pyrazino[2,3-c][1,8]naphth yridine-3-carboxylate 7h (100 mg, 170.92 μmol), (3-methoxynaphthalen-1-yl)boronic acid 11a (103.58 mg, 512.76 μmol), tetrakis(triphenylphosphine)palladium (19.75 mg, 17.09 μmol) and potassium phosphate (181.40 mg, 854.60 μmol) were dissolved in a mixed solvent of 0.3 mL of water and 1.5 mL of 1,4-dioxane, and replaced with nitrogen 3 times for 16 h of reaction at 100° C. under nitrogen atmosphere. The progress of the reaction was monitored by LC-MS. Then the reaction solution was concentrated under reduced pressure, and the obtained residue was separated and purified by flash silica gel column chromatography (eluent: system E) to obtain tert-butyl (2R,4aR)-11-fluoro-8-(2-isopropyl-4-methylpyridin-3-yl)-10-(3-methoxynaphthalen-1-yl)-2,6-dimethyl-5,7-dioxo-1,2,4,4a,5,6,7,8-octahydro-3H-pyrazino[1',2':4,5]pyrazino[2,3-c][1,8]naphthyridine-3-carboxylate 11b (0.1 g, 141.48 μmol) with a yield of 82.78%.

MS m/z(ESI): 707.7 $[M+1]^+$

The Second Step (2R,4aR)-11-fluoro-10-(3-hydroxynaphthalen-1-yl)-8-(2-isopropyl-4-methylpyridin-3-yl)-2,6-di methyl-2,3,4,4a,6,8-hexahydro-1H-pyrazino[1',2':4,5]pyrazino[2,3-c][1,8]naphthyridine-5,7-dione Tert-butyl (2R,4aR)-11-fluoro-8-(2-isopropyl-4-methylpyridin-3-yl)-10-(3-methoxynaphthalen-1-yl)-2,6-dimethyl-5,7-dioxo-1,2,4,4a,5,6,7,8-octahydro-3H-pyrazino[1',2':4, 5]pyrazino[2,3-c][1,8]naphthyridine-3-carboxylate 11b (70 mg, 99.04 μmol) was dissolved in 5 mL of dichloromethane, and added with boron tribromide (1.40 g, 5.59 mmol) for 16 h of reaction at 20° C. Then the reaction solution was added with 10 mL of methanol for quenching the reaction, concentrated under reduced pressure, diluted with 20 mL of water, and washed with ethyl acetate (20 mL×2). The aqueous phase was collected, and freeze-dried to obtain a crude product (2R,4aR)-11-fluoro-10-(3-hydroxynaphthalen-1-yl)-8-(2-isopropyl-4-methylpyridin-3-yl)-2,6-dimethyl-2,3,4,4a,6,8-hexahydro-1H-pyrazino[1',2':4,5]pyrazino[2,3-c][1,8]naphthyrid ine-5,7-dione 11c (100 mg, 168.73 μmol).

MS m/z(ESI): 593.4 $[M+1]^+$

The Third Step

Butyl 4-((2R,4aR)-3-acryloyl-11-fluoro-8-(2-isopropyl-4-methylpyridin-3-yl)-2,6-dimethyl-5,7-dioxo-2,3,4,4a,5,6,7,8-octahydro-1H-pyrazino[1',2':4,5]pyrazino[2,3-c][1,8]naphthyridin-10-yl)naphthalene-2-yl acrylate (2R,4aR)-11-fluoro-10-(3-hydroxynaphthalen-1-yl)-8-(2-isopropyl-4-methylpyridin-3-yl)-2,6-dimethyl-2,3,4,4a,6,8-hexahydro-1H-pyrazino[1',2':4,5]pyrazino[2,3-c][1,8]naphthyrid ine-5,7-dione 11c (100 mg, 168.73 μmol) and triethylamine (85.37 mg, 843.65 μmol) were dissolved in dichloromethane (5 mL), and dropwise added with acryloyl chloride (15.27 mg, 168.73 μmol) at 10° C. for 16 h of reaction at 10-20° C. The progress of the reaction was monitored by LC-MS. After the reaction was completed, the reaction solution was added with 10 mL of water, and extracted with dichloromethane (10 mL×2). The organic phases were combined, dried over anhydrous magnesium sulfate, filtered, and concentrated under reduced pressure to obtain a crude product butyl 4-((2R,4aR)-3-acryloyl-11-fluoro-8-(2-isopropyl-4-methylpyridin-3-yl)-2,6-dimethyl-5,7-dioxo-2,3,4,4a,5,6,7,8-octahydro-1H-pyrazino[1',2':4,5]pyrazino[2,3-c][1,8]naphthyridin-10-yl)naphthal ene-2-yl acrylate 11d (150 mg, 214.05 μmol), which was then directly used in the next reaction.

MS m/z(ESI): 701.2 $[M+1]^+$

The Fourth Step

(2R,4aR)-3-acryloyl-11-fluoro-10-(3-hydroxynaphthalen-1-yl)-8-(2-isopropyl-4-methylpyridin-3-yl)-2,6-dimethyl-2,3,4,4a,6,8-hexahydro-1H-pyrazino[1',2':4,5]pyrazino[2,3-c][1,8]naphthyridin e-5,7-dione 4-((2R,4aR)-3-acryloyl-11-fluoro-8-(2-isopropyl-4-methylpyridin-3-yl)-2,6-dimethyl-5,7-dioxo-2,3,4,4a,5,6,7,8-octahydro-1H-pyrazino[1',2':4,5]pyrazino[2,3-c][1,8]naphthyridin-10-yl)naphthalene-2-yl butyl acrylate 11d (150 mg, 214.05 μmol) was dissolved in 1 mL of tetrahydrofuran, and dropwise added with an aqueous solution (1 mL) of lithium hydroxide monohydrate (26.95 mg, 642.16 μmol) for 16 h of reaction at 15° C. The progress of the reaction was monitored by LC-MS. After the reaction was completed, the reaction solution was dropwise added with 1 M dilute hydrochloric acid for adjustment of the pH to 7, and extracted with ethyl acetate (10 mL×2). The organic phases were combined, dried over anhydrous magnesium sulfate, filtered, and concentrated under reduced pressure. The obtained residue was separated and purified by preparative liquid chromatography (separation column: Boston Prime C18, 150×30 mm I.D., 5 μm; mobile phase A: water (0.05% $NH_3H_2O$+10 mM $NH_4HCO_3$), mobile phase B: acetonitrile; flow rate: 25 mL/min) to obtain (2R,4aR)-3-acryloyl-11-fluoro-10-(3-hydroxynaphthalen-1-yl)-8-(2-isopropyl-4-methylpyridin-3-yl)-2,6-dimethyl-2,3,4,4a,6,8-hexahydro-1H-pyrazino[1',2':4,5]pyrazino[2,3-c][1,8]naphthyridin e-5,7-dione 11(26 mg, 40.20 μmol) with a yield of 18.78%.

MS m/z(ESI): 647.2$[M+1]^+$ $^1H$ NMR (400 MHz, DMSO-$d_6$) δ 10.02 (s, 1H), 8.42-8.37 (m, 1H), 8.14-8.04 (m, 1H), 7.75 (d, J=8.3 Hz, 1H), 7.45-7.33 (m, 2H), 7.27-7.12 (m, 3H), 7.11-6.83 (m, 2H), 6.22-6.12 (m, 1H), 5.83-5.71 (m, 1H), 5.05 (br d, J=13.8 Hz, 1H), 4.81 (br s, 1H), 4.63 (br d, J=13.3 Hz, 1H), 4.46 (s, 1H), 4.07-3.95 (m, 1H), 3.77 (dd, J=4.1, 14.2 Hz, 1H), 3.54-3.41 (m, 2H), 3.29-3.22 (m, 1H), 2.95-2.79 (m, 1H), 2.07-1.81 (m, 3H), 1.64-1.52 (m, 3H), 1.14-0.84 (m, 6H).

Example 5—Compound 16

(2R,4aR)-3-acryloyl-11-chloro-10-(2-fluoro-6-hydroxyphenyl)-8-(2-isopropyl-4-(methylthio)pyri din-3-yl)-2,6-dimethyl-2,3,4,4a,6,8-hexahydro-1H-pyrazino[1',2':4,5]pyrazino[2,3-c][1,8]naphth yridine-5,7-dione

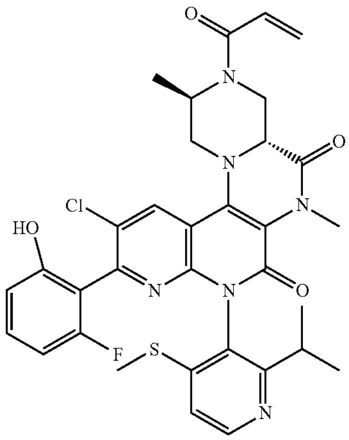 [SMILES: C=CC(=O)N1C[C@@H]2C(=O)N(C)c3c(c4cc(Cl)c(-c5c(O)cccc5F)nc4n(-c4c(SC)ccnc4C(C)C)c3=O)N2C[C@H]1C]

Method 1

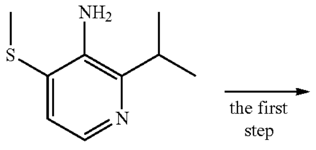

16a

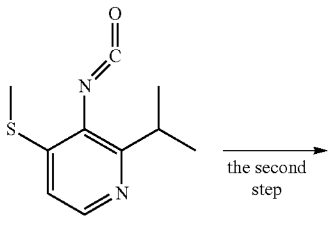

16b

-continued
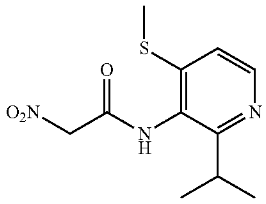
16c
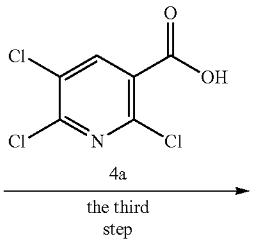
4a
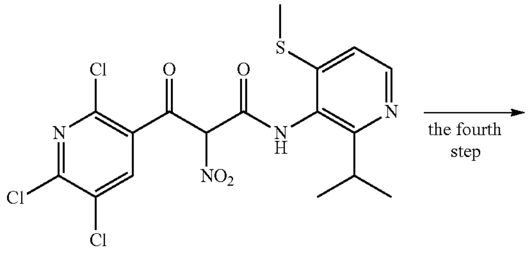
16e
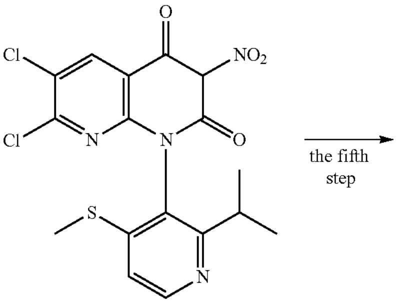
16f
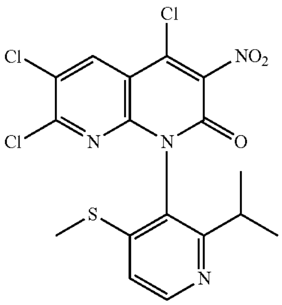
16g
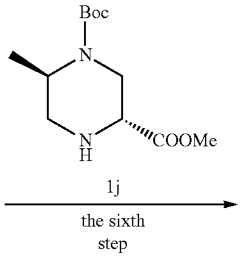
1j
-continued
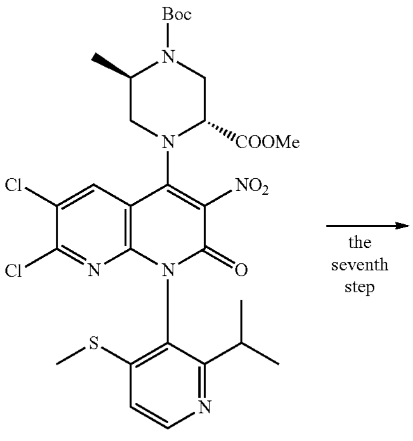
16i
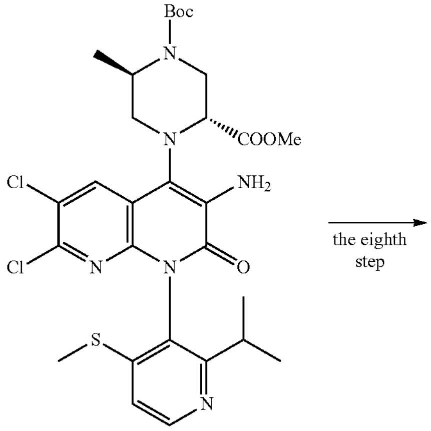
16j
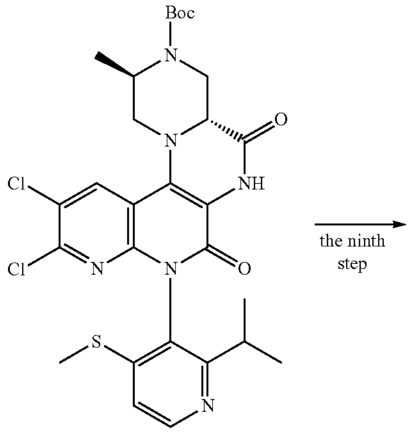
16k -continued

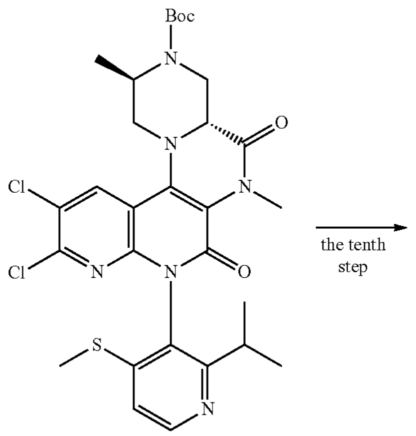

16l

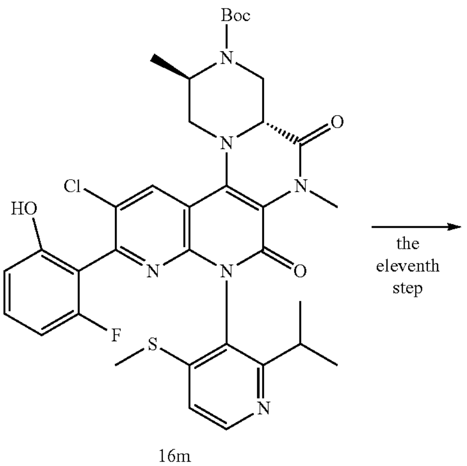

16m

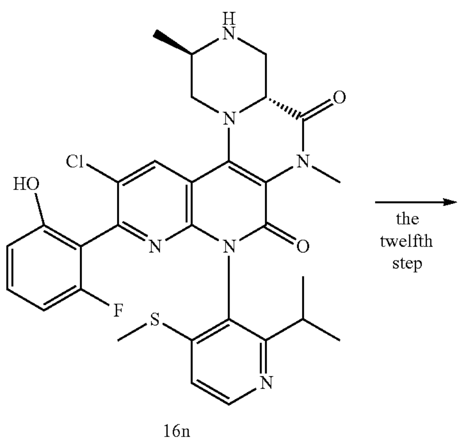

16n

-continued

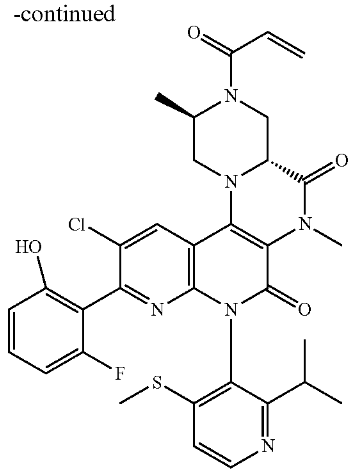

16

The First Step

3-Isocyanato-2-isopropyl-4-(methylthio)pyridine

2-Isopropyl-4-(methylthio)pyridin-3-amine 16a (3.38 g, 18.45 mmol, self-produced according to patent WO2020239077) was added into tetrahydrofuran (20 mL), cooled to 0° C., then added with triethylamine (1.86 g, 18.45 mmol), and slowly added in batches with triphosgene (5.48 g, 18.45 mmol) for 0.5 h of reaction at 0° C. Then the reaction solution was filtered to obtain 3-isocyanato-2-isopropyl-4-(methylthio)pyridine 16b (3.83 g) with a yield of 100%, which was directly used in the next reaction without purification.

The Second Step

N-(2-isopropyl-4-(methylthio)pyridin-3-yl)-2-nitroacetamide

Nitromethane (1.12 g, 18.45 mmol) was added into tetrahydrofuran (20 mL), cooled down to 0° C., then added with potassium tert-butoxide (4.41 g, 36.9 mmol) for 0.5 h of reaction at 0° C., and then slowly dropwise added with 3-isocyanate-2-isopropyl-4-(methylthio)pyridine 16b (3.83 g, 18.45 mmol). After the reaction was completed, the reaction solution was extracted with ethyl acetate (30 mL) and water (30 mL), and the organic phase was washed with saturated brine (30 mL×3), and dried over anhydrous sodium sulfate. The obtained residue was purified by silica gel column chromatography (eluent: system A) to obtain N-(2-isopropyl-4-(methylthio)pyridin-3-yl)-2-nitroacetamide 16c (2.2 g) with a yield of 44.95%.

MS m/z(ESI): 270.1 $[M+1]^+$

The Third Step

N-(2-isopropyl-4-(methylthio)pyridin-3-yl)-2-nitro-3-oxo-3-(2,5,6-trichloropyridin-3-yl)propana mide N-(2-isopropyl-4-(methylthio)pyridin-3-yl)-2-nitroacetamide 16c (820 mg, 3.05 mmol), 2,5,6-trichloronicotinic acid 4a (686.25 mg, 3.05 mmol), tetramethylfluorourea hexafluorophosphate (1.2 g, 4.57 mmol) and N,N-diisopropylethylamine (923 mg, 7.1 mmol) were added to acetonitrile (20 mL) for 3 h of reaction at room temperature. After the reaction was completed, the reaction solution was extracted with ethyl acetate (30 mL) and water (30 mL), and the organic phase was washed with saturated brine (30 mL×3), and dried over anhydrous sodium sulfate. The obtained residue was purified by silica gel column chromatography (eluent: system A) to obtain N-(2-isopropyl-4-(methylthio)pyridin-3-yl)-2-nitro-3-oxo-3-(2,5,6-trichloropyridin-3-yl)propanamide 16e (1.2 g) with a yield of 82.56%.

MS m/z(ESI): 477.1 $[M+1]^+$

The Fourth Step 6,7-Dichloro-1-(2-isopropyl-4-(methylthio)pyridin-3-yl)-3-nitro-1,8-naphthyridine-2,4(1H,3H)-di one N-(2-isopropyl-4-(methylthio)pyridin-3-yl)-2-nitro-3-oxo-3-(2,5,6-trichloropyridin-3-yl)propanamide 16e (1.2 g, 2.52 mol) was added to N,N-dimethylformamide (20 mL), added with cesium carbonate (1.6 g, 5.04 mmol), and heated to 85° C. for reaction overnight After the reaction was completed, the reaction solution was extracted with ethyl acetate (30 mL) and water (30 mL), and the organic phase was washed with saturated brine (30 mL×3), and dried over anhydrous sodium sulfate. The obtained residue was purified by silica gel column chromatography (eluent: system A) to obtain 6,7-dichloro-1-(2-isopropyl-4-(methylthio)pyridin-3-yl)-3-nitro-1,8-naphthyridine-2,4(1H,3H)-di one 16f (980 mg) with a yield of 87.64%.

MS m/z(ESI): 441.1 $[M+1]^+$

The Fifth Step 4,6,7-Trichloro-1-(2-isopropyl-4-(methylthio)pyridin-3-yl)-3-nitro-1,8-naphthyridin-2(1H)-one 6,7-dichloro-1-(2-isopropyl-4-(methylthio)pyridin-3-yl)-3-nitro-1,8-naphthyridine-2,4(1H,3H)-dione 16f (610 mg, 1.38 mol) was added to phosphoryl chloride (10 mL), and heated to 110° C. for 3 h of reaction. After the reaction was completed, the reaction solution was poured into ice water, adjusted to alkaline, extracted with dichloromethane (50 mL) and dried over anhydrous sodium sulfate. The obtained residue was purified by silica gel column chromatography (eluent: system A) to obtain 4,6,7-trichloro-1-(2-isopropyl-4-(methylthio)pyridin-3-yl)-3-nitro-1,8-naphthyridin-2(1H)-one 16g (460 mg) with a yield of 72.24%.

MS m/z(ESI): 459.1 $[M+1]^+$

The Sixth Step 1-(Tert-butyl)-3-methyl(3R,6R)-4-(6,7-dichloro-1-(2-isopropyl-4-(methylthio)pyridin-3-yl)-3-nitr o-2-oxo-1,2-dihydro-1,8-naphthyridin-4-yl)-6-methylpiperazine-1,3-dicarboxylate 4,6,7-Trichloro-1-(2-isopropyl-4-(methylthio)pyridin-3-yl)-3-nitro-1,8-naphthyridin-2(1H)-one 16g (460 mg, 1 mmol), and 1-(tert-butyl)-3-methyl(3R,6R)-6-methylpiperazine-1,3-dicarboxylate 1j (309.42 mg, 1.15 mmol) were added into acetonitrile (20 mL) and heated to reflux overnight under argon protection. After the reaction was completed, the reaction solution was extracted with ethyl acetate (20 mL) and water (20 mL), and the organic phase was washed with saturated brine (20 mL×3), and dried over anhydrous sodium sulfate. The obtained residue was purified by silica gel column chromatography (eluent: system A) to obtain 1-(tert-butyl)-3-methyl(3R,6R)-4-(6,7-dichloro-1-(2-isopropyl-4-(methylthio)pyridin-3-yl)-3-nitr o-2-oxo-1,2-dihydro-1,8-naphthyridin-4-yl)-6-methylpiperazine-1,3-dicarboxylate 16i (544 mg) with a yield of 80%.

MS m/z(ESI): 681.1 $[M+1]^+$

The Seventh Step 1-(Tert-butyl)-3-methyl(3R,6R)-4-(6,7-dichloro-1-(2-isopropyl-4-(methylthio)pyridin-3-yl)-3-amino-2-oxo-1,2-dihydro-1,8-naphthyridin-4-yl)-6-methylpiperazine-1,3-dicarboxylate 1-(Tert-butyl)-3-methyl(3R,6R)-4-(6,7-dichloro-1-(2-isopropyl-4-(methylthio)pyridin-3-yl)-3-nitro-2-oxo-1,2-dihydro-1,8-naphthyridin-4-yl)-6-methylpiperazine-1,3-dicarboxylate 16i (544 mg, 800 μmol) was added into acetonitrile (20 mL), cooled to 0° C., and added with N,N-diisopropylethylamine (520.0 mg, 4.0 mmol) and trichlorosilane (379.26 mg, 2.5 mmol) for 2 h of reaction at room temperature. After the reaction was completed, the reaction solution was extracted with ethyl acetate (20 mL) and water (20 mL), and the organic phase was washed with saturated brine (20 mL×3), and dried over anhydrous sodium sulfate. The obtained residue was purified by silica gel column chromatography (eluent: system A) to obtain 1-(tert-butyl)-3-methyl(3R,6R)-4-(6,7-dichloro-1-(2-isopropyl-4-(methylthio)pyridin-3-yl)-3-ami no-2-oxo-1,2-dihydro-1,8-naphthyridin-4-yl)-6-methylpiperazine-1,3-dicarboxylate 16j (420 mg) with a yield of 81.37%.

MS m/z(ESI): 651.1 $[M+1]^+$

The Eighth Step

Tert-butyl (2R,4aR)-10,11-dichloro-8-(2-isopropyl-4-(methylthio)pyridin-3-yl)-2-methyl-5,7-dioxo-1,2,4,4a,5,6,7,8-octahydro-3H-pyrazino[1',2':4,5]pyrazino[2,3-c][1,8]naphthyr idine-3-carboxylate 1-(Tert-butyl)-3-methyl(3R,6R)-4-(6,7-dichloro-1-(2-isopropyl-4-(methylthio)pyridin-3-yl)-3-amino-2-oxo-1,2-dihydro-1,8-naphthyridin-4-yl)-6-methylpiperazine-1,3-dicarboxylate 16j (420 mg, 651.22 μmol) was added to N,N-dimethylformamide (10 mL), and added with potassium carbonate (179.73 mg, 1.31 mmol) for 3 h of reaction at room temperature. After the reaction was completed, the reaction solution was extracted with ethyl acetate (20 mL) and water (20 mL), and the organic phase was washed with saturated brine (20 mL×3), and dried over anhydrous sodium sulfate. The obtained residue was purified by silica gel column chromatography (eluent: system A) to obtain tert-butyl (2R,4aR)-10,11-dichloro-8-(2-isopropyl-4-(methylthio)pyridin-3-yl)-2-methyl-5,7-dioxo-1,2,4,4a,5,6,7,8-octahydro-3H-pyrazin o[1',2':4,5]pyrazino[2,3-c][1,8]naphthyridine-3-carboxylate 16k (330 mg), yield: 82.04%.

MS m/z(ESI): 619.1 $[M+1]^+$

The Ninth Step

Tert-butyl (2R,4aR)-10,11-dichloro-8-(2-isopropyl-4-(methylthio)pyridin-3-yl)-2,6-dimethyl-5,7-dioxo-1,2,4,4a,5,6,7,8-octahydro-3H-pyrazino[1',2':4,5]pyrazino[2,3-c][1,8]naphth yridine-3-carboxylate Tert-butyl (2R,4aR)-10,11-dichloro-8-(2-isopropyl-4-(methylthio)pyridin-3-yl)-2-methyl-5,7-dioxo-1,2,4,4a,5,6, 7,8-octahydro-3H-pyrazino[1',2':4,5]pyrazino[2,3-c][1,8] naphthyr idine-3-carboxylate 16k (330 mg, 533.98 μmol) and potassium carbonate (147.72 mg, 1.06 mmol) were added into acetone (10 mL), dropwise added with iodomethane (149.46 mg, 1.06 mmol), and heated to reflux for 2 h. After the reaction was completed, the reaction solution was extracted with ethyl acetate (20 mL) and water (20 mL), and the organic phase was washed with saturated brine (20 mL×3), and dried over anhydrous sodium sulfate. The obtained residue was purified by silica gel column chromatography (eluent: system A) to obtain tert-butyl (2R,4aR)-10,11-dichloro-8-(2-isopropyl-4-(methylthio)pyridin-3-yl)-2,6-dimethyl-5,7-dioxo-1,2, 4,4a,5,6,7,8-octahydro-3H-pyrazino[1',2':4,5]pyrazino[2,3-c][1,8]naphthyridine-3-carboxylate 16l (300 mg) with a yield of 87.34%.

MS m/z(ESI): 633.1 $[M+1]^+$

The Tenth Step

Tert-butyl (2R,4aR)-11-chloro-10-(2-fluoro-6-hydroxyphenyl)-8-(2-isopropyl-4-(methylthio)pyridin-3-yl)-2,6-dimethyl-5,7-dioxo-1,2,4,4a,5,6,7,8-octahydro-3H-pyrazino[1',2':4, 5]pyrazino[2,3-c][1,8] naphthyridine-3-carboxylate Tert-butyl (2R,4aR)-10,11-dichloro-8-(2-isopropyl-4-(methylthio)pyridin-3-yl)-2,6-dimethyl-5,7-dioxo-1,2,4,4a,5,6,7,8-octahydro-3H-pyrazino[1',2':4,5]pyrazino[2,3-c][1,8]na phthyridine-3-carboxylate 161 (300 mg, 474.68 μmol), potassium (2-fluoro-6-hydroxyphenyl) trifluoroborate (155.22 mg, 712.02 μmol), [1,1'-bis(diphenylphosphine)ferrocene]palladium dichloride (52.84 mg, 71.21 μmol) and potassium acetate (139.16 mg, 1.42 mmol) were added to 13 mL of a mixed solvent (1,4-dioxane:water=10:3), and heated to 100° C. for 5 h of reaction. After the reaction was completed, the reaction solution was cooled to room temperature and filtered. The filtrate was collected, and extracted with ethyl acetate (20 mL) and water (10 mL). The organic phase was washed with saturated brine (10 mL×3), and dried over anhydrous sodium sulfate. The obtained residue was purified by silica gel column chromatography (eluent: system A) to obtain tert-butyl (2R,4aR)-11-chloro-10-(2-fluoro-6-hydroxyphenyl)-8-(2-isopropyl-4-(methylthio)pyridin-3-yl)-2,6-dimethyl-5,7-dioxo-1,2,4,4a,5,6,7,8-octahydro-3H-pyrazino[1',2':4, 5]pyrazino[2,3-c][1,8] naphthyridine-3-carboxylate 16m (150 mg) with a yield of 43.67%.

MS m/z(ESI): 709.1 $[M+1]^+$

The Eleventh Step (2R,4aR)-11-chloro-10-(2-fluoro-6-hydroxyphenyl)-8-(2-isopropyl-4-(methylthio)pyridin-3-yl)-2,6-dimethyl-2,3,4,4a,6,8-hexahydro-1H-pyrazino[1',2':4,5] pyrazino[2,3-c][1,8]naphthyridine-5,7-dione Tert-butyl (2R,4aR)-11-chloro-10-(2-fluoro-6-hydroxyphenyl)-8-(2-isopropyl-4-(methylthio)pyridin-3-yl)-2,6-dimethyl-5,7-dioxo-1,2,4,4a,5,6,7,8-octahydro-3H-pyrazino [1',2':4, 5]pyrazino[2,3-c][1,8]naphthyridine-3-carboxylate 16m (150 mg, 207.75 μmol) was added to dichloromethane (5 mL), cooled to 0° C., and dropwise added with dioxane hydrochloride solution (4 M, 2 mL) for 2 h of reaction at room temperature. After the reaction was completed, the reaction solution was poured into ice water, and extracted with dichloromethane (50 mL). The aqueous phase was adjusted to weakly alkaline with saturated aqueous sodium carbonate solution, and extracted with 10 mL of ethyl acetate and water (10 mL). The organic phase was washed with saturated brine (10 mL×3), and dried over anhydrous sodium sulfate. The obtained residue was purified by silica gel column chromatography (eluent: system A) to obtain (2R, 4aR)-11-chloro-10-(2-fluoro-6-hydroxyphenyl)-8-(2-isopropyl-4-(methylthio)pyridin-3-yl)-2,6-dimethyl-2,3,4,4a,6, 8-hexahydro-1H-pyrazino[1',2':4,5]pyrazino[2,3-c][1,8] naphthyridine-5,7-dione 16n (80 mg) with a yield of 64.19%.

MS m/z(ESI): 609.1 $[M+1]^+$ The twelfth step (2R,4aR)-3-acryloyl-11-chloro-10-(2-fluoro-6-hydroxyphenyl)-8-(2-isopropyl-4-(methylthio)pyri din-3-yl)-2,6-dimethyl-2,3,4, 4a,6,8-hexahydro-1H-pyrazino[1',2':4,5]pyrazino[2,3-c][1, 8]naphth yridine-5,7-dione (2R,4aR)-11-chloro-10-(2-fluoro-6-hydroxyphenyl)-8-(2-isopropyl-4-(methylthio)pyridi n-3-yl)-2,6-dimethyl-2,3, 4,4a,6,8-hexahydro-1H-pyrazino[1',2':4,5]pyrazino[2,3-c] [1,8]naphthyr idine-5,7-dione 16n (80 mg, 131.34 μmol) was added to dichloromethane (5 mL), cooled to 0° C., dropwise added with triethylamine (26.53 mg, 262.68 μmol), and slowly dropwise added with a solution of acryloyl chloride (12.92 mg, 142.71 μmol) in dichloromethane for reaction at 0° C. After the reaction was completed, the reaction solution was extracted with dichloromethane (10 mL) and water (10 mL) at room temperature. The organic phase was washed with saturated brine (10 mL×3), dried over anhydrous sodium sulfate, and concentrated under reduced pressure. The obtained residue was separated and purified to obtain a product (2R,4aR)-3-acryloyl-11-chloro-10-(2-fluoro-6-hydroxyphenyl)-8-(2-isopropyl-4-(methylthio)pyri din-3-yl)-2,6-dimethyl-2,3,4,4a,6,8-hexahydro-1H-pyrazino[1',2':4,5]pyrazino[2,3-c][1,8]naphth yridine-5,7-dione 16 (25 mg) with a yield of 27.08%.

MS m/z(ESI): 663.1 $[M+1]^+$

1H NMR (400 MHz, $CDCl_3$) δ 8.61 (d, J=5.3 Hz, 1H), 8.29 (s, 1H), 7.74 (s, 1H), 7.24 (d, J=2.0 Hz, 1H), 7.11 (d, J=5.4 Hz, 1H), 7.08-6.99 (m, 1H), 6.73-6.70 (m, 1H), 6.69 (t, J=1.3 Hz, 1H), 6.36 (dd, J=16.9, 2.0 Hz, 1H), 5.81 (dd, J=10.6, 1.9 Hz, 1H), 5.07 (s, 1H), 4.77 (d, J=14.0 Hz, 1H), 3.82 (dd, J=14.1, 4.4 Hz, 1H), 3.64 (d, J=4.0 Hz, 1H), 3.49 (s, 3H), 3.22 (d, J=12.2 Hz, 1H), 3.00 (dd, J=12.0, 3.6 Hz, 1H), 2.53-2.46 (m, 1H), 2.45 (s, 3H), 1.68 (s, 3H), 1.20 (d, J=6.7 Hz, 3H), 0.95 (d, J=6.7 Hz, 3H).

Method 2

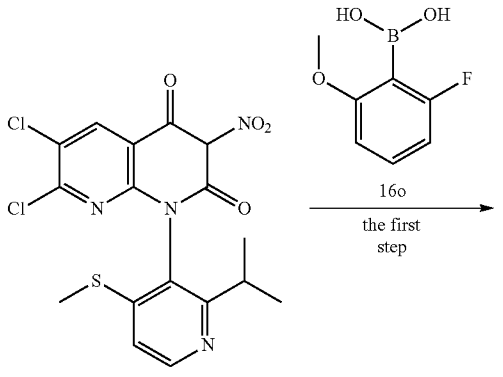

16o

16f

-continued
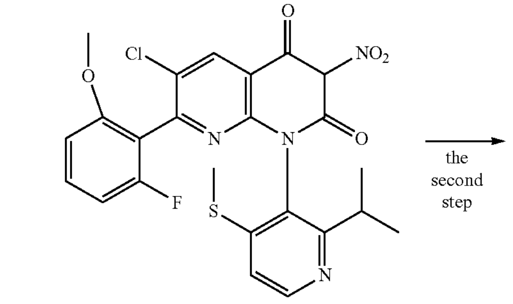
16p
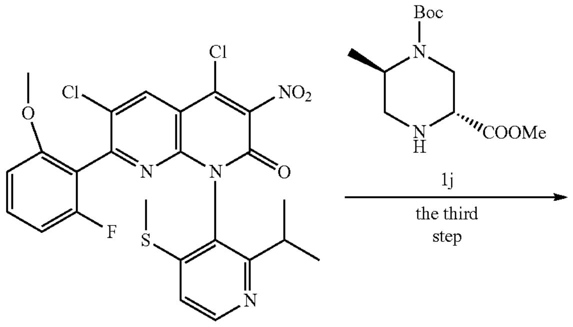
16q
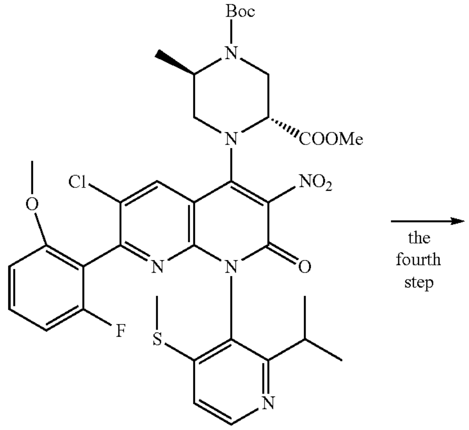
16r
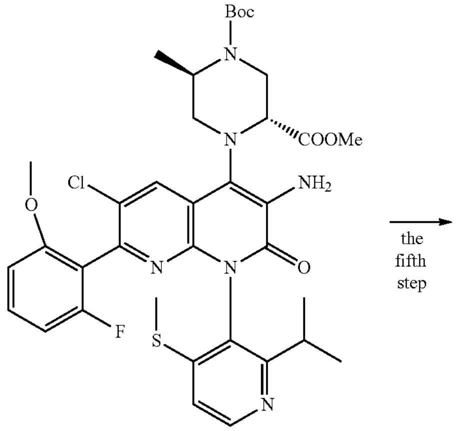
16s
-continued
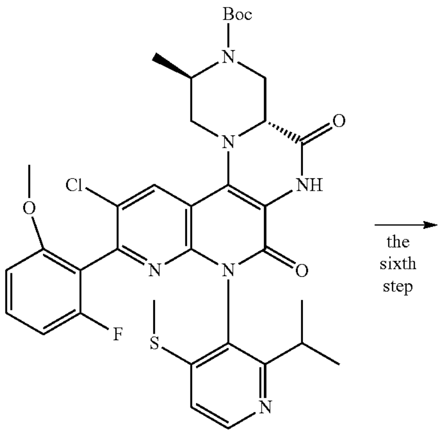
16t
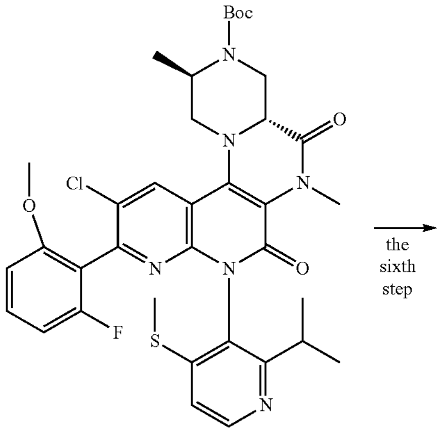
16u
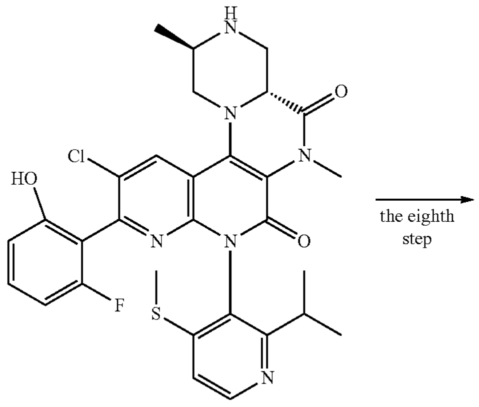
16n -continued

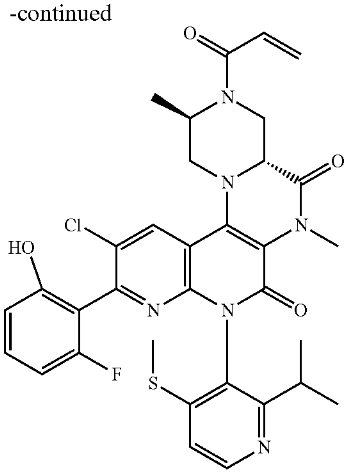

16

The First Step

6-Chloro-7-(2-fluoro-6-methoxyphenyl)-1-(2-isopropyl-4-(methylthio)pyridin-3-yl)-3-nitro-1,8-naphthyridine-2,4(1H,3H)-dione 6,7-Dichloro-1-(2-isopropyl-4-(methylthio)pyridin-3-yl)-3-nitro-1,8-naphthyridine-2,4(1H,3H)-dione 16f (500 mg, 1.13 mmol) was added to a mixed solvent of dioxane (20 mL) and water (5 mL), added with (2-fluoro-6-methoxyphenyl)boronic acid 16o (386 mg, 2.26 mmol), sodium carbonate (220 mg, 2.26 mmol) and tetrakistriphenylphosphine palladium (12.7 mg, 0.01 mmol), and heated to 100° C. for reaction overnight under argon protection. After the reaction was completed, the reaction solution was filtered, and the filtrate was extracted with ethyl acetate (20 mL) and water (20 mL), dried over anhydrous sodium sulfate, and concentrated under reduced pressure. The obtained residue was purified by silica gel column chromatography (eluent: system A) to obtain a product 6-chloro-7-(2-fluoro-6-methoxyphenyl)-1-(2-isopropyl-4-(methylthio) pyridin-3-yl)-3-nitro-1,8-naphthyridine-2,4(1H,3H)-dione 16p (530 mg, 1 mmol) with a yield of 72.24%.

MS m/z(ESI): 531.1 [M+1]$^+$

The Second Step 4,6-Dichloro-7-(2-fluoro-6-methoxyphenyl)-1-(2-isopropyl-4-(methylthio)pyridin-3-yl)-3-nitro-1,8-naphthyridin-2(1H)-one 6-Chloro-7-(2-fluoro-6-methoxyphenyl)-1-(2-isopropyl-4-(methylthio)pyridin-3-yl)-3-nitro-1,8-naphthyridine-2,4(1H,3H)-dione 16p (530 mg, 1 mmol) was added to phosphoryl chloride (10 mL), and heated to 110° C. for 3 h of reaction. The reaction solution was poured into ice water, adjusted to alkaline with saturated sodium carbonate solution, extracted with dichloromethane (50 mL), dried over anhydrous sodium sulfate, filtered, and concentrated under reduced pressure. The obtained residue was purified by silica gel column chromatography (eluent: system A) to obtain a product 4,6-dichloro-7-(2-fluoro-6-methoxyphenyl)-1-(2-isopropyl-4-(methylthio)pyridin-3-yl)-3-nitro-1,8-naphthyridin-2(1H)-one 16q (439.2 mg, 800 µmol) with a yield of 80%.

MS m/z(ESI): 549.1[M+1]$^+$

The Third Step 1-(Tert-butyl)3-methyl(3R,6R)-4-(6-chloro-7-(2-fluoro-6-methoxyphenyl)-1-(2-isopropyl-4-(methylthio)pyridin-3-yl)-3-nitro-2-oxo-1,2-dihydro-1,8-naphthyridin-4-yl)-6-methylpiperazine-1,3-dicarboxylate 4,6-Dichloro-7-(2-fluoro-6-methoxyphenyl)-1-(2-isopropyl-4-(methylthio)pyridin-3-yl)-3-nitro-1,8-naphthyridin-2(1H)-one 16q (267 mg, 487.8 µmol) and 1-(tert-butyl)-3-methyl(3R,6R)-6-methylpiperazine-1,3-dicarboxylate 1j (196.8 mg, 731.7 µmol) were added into acetonitrile (20 mL) for reflux overnight under argon protection. After the reaction was completed, the reaction solution was extracted with ethyl acetate (20 mL) and water (20 mL). The organic phase was washed with saturated brine (20 mL×3), dried over anhydrous sodium sulfate, filtered, and concentrated under reduced pressure. The obtained residue was purified by silica gel column chromatography (eluent: system A) to obtain a product 1-(tert-butyl)3-methyl(3R,6R)-4-(6-chloro-7-(2-fluoro-6-methoxyphenyl)-1-(2-isopropyl-4-(methylthio) pyridin-3-yl)-3-nitro-2-oxo-1,2-dihydro-1,8-naphthyridin-4-yl)-6-methylpiperazine-1,3-dicarboxylate 16r (300 mg, 390.24 µmol) with a yield of 80%.

MS m/z(ESI): 771.1[M+1]$^+$

The Fourth Step 1-(Tert-butyl) 3-methyl (3R,6R)-4-(3-amino-6-chloro-7-(2-fluoro-6-methoxyphenyl)-1-(2-isopropyl-4-(methylthio)pyridin-3-yl)-2-oxo-1,2-dihydro-1,8-naphthyridin-4-yl)-6-methylpiperazine-1,3-dicarboxylate 1-(Tert-butyl) 3-methyl (3R,6R)-4-(6-chloro-7-(2-fluoro-6-methoxyphenyl)-1-(2-isopropyl-4-(methylthio)pyridin-3-yl)-3-nitro-2-oxo-1,2-dihydro-1,8-naphthyridin-4-yl)-6-methyl piperazine-1,3-dicarboxylate 16r (300 mg, 390.24 µmol) was added to a mixed solvent of N,N-dimethylformamide (10 mL) and acetonitrile (10 mL), cooled to 0° C., and added with diisopropylethylamine (176 mg, 1.75 mmol) and trichlorosilane (188.92 mg, 1.38 mmol) for 2 h of reaction at room temperature. After the reaction was completed, the reaction solution was extracted with ethyl acetate (20 mL) and water (20 mL). The organic phase was washed with saturated brine (20 mL×3), dried over anhydrous sodium sulfate, filtered, and concentrated under reduced pressure. The obtained residue was purified by silica gel column chromatography (eluent: system A) to obtain a product 1-(tert-butyl) 3-methyl (3R,6R)-4-(3-amino-6-chloro-7-(2-fluoro-6-methoxyphenyl)-1-(2-isopropyl-4-(methylthio)pyridin-3-yl)-2-oxo-1,2-dihydro-1,8-naphthyridin-4-yl)-6-methylpiperazine-1,3-dicarboxylate 16s (230 mg, 320 µmol) with a yield of 82.04%.

MS m/z(ESI): 741.1 [M+1]$^+$

The Fifth Step

Tert-butyl (2R,4aR)-11-chloro-10-(2-fluoro-6-methoxyphenyl)-8-(2-isopropyl-4-(methylthio)pyridin-3-yl)-2-methyl-5,7-dioxo-1,2,4,4a,5,6,7,8-octahydro-3H-pyrazino[1',2':4,5]pyrazino[2,3-c][1,8]naphthyridine-3-carboxylate 1-(Tert-butyl) 3-methyl (3R,6R)-4-(3-amino-6-chloro-7-(2-fluoro-6-methoxyphenyl)-1-(2-isopropyl-4-(methylthio)

pyridin-3-yl)-2-oxo-1,2-dihydro-1,8-naphthyridin-4-yl)-6-methylpip erazine-1,3-dicarboxylate 16s (230 mg, 320 μmol) was added to N,N-dimethylformamide (10 mL), and added with potassium carbonate (88.32 mg, 640 μmol) for 3 h of reaction at room temperature. After the reaction was completed, the reaction solution was extracted with ethyl acetate (20 mL) and water (20 mL). The organic phase was washed with saturated brine (20 mL×3), dried over anhydrous sodium sulfate, filtered, and concentrated under reduced pressure. The obtained residue was purified by silica gel column chromatography (eluent: system A) to obtain a product tert-butyl (2R,4aR)-11-chloro-10-(2-fluoro-6-methoxyphenyl)-8-(2-isopropyl-4-(methylthio)pyridin-3-yl)-2-methyl-5,7-dioxo-1,2,4,4a,5,6,7,8-octahydro-3H-pyrazino[1',2':4,5]p yrazino[2,3-c][1,8]naphthyridine-3-carboxylate 16t (182 mg, 256.48 μmol) with a yield of 80.04%.

MS m/z(ESI): 709.1[M+1]$^+$

The Sixth Step

Tert-butyl (2R,4aR)-11-chloro-10-(2-fluoro-6-methoxyphenyl)-8-(2-isopropyl-4-(methylthio)pyridin-3-yl)-2,6-dimethyl-5,7-dioxo-1,2,4,4a,5,6,7,8-octahydro-3H-pyrazino[1',2':4, 5]pyrazino[2,3-c][1, 8]naphthyridine-3-carboxylate Tert-butyl (2R,4aR)-11-chloro-10-(2-fluoro-6-methoxyphenyl)-8-(2-isopropyl-4-(methylthio)pyridin-3-yl)-2-methyl-5,7-dioxo-1,2,4,4a,5,6,7,8-octahydro-3H-pyrazino[1',2':4,5]p yrazino[2,3-c][1,8]naphthyridine-3-carboxylate 16t (182 mg, 256.48 μmol) and potassium carbonate (70.89 mg, 512.9 μmol) were added to acetone (5 mL), dropwise added with iodomethane (72.46 mg, 512.96 μmol), and heated to reflux for 2 h. After the reaction was completed, the reaction solution was extracted with ethyl acetate (20 mL) and water (20 mL). The organic phase was washed with saturated brine (20 mL×3), dried over anhydrous sodium sulfate, filtered, and concentrated under reduced pressure. The obtained residue was purified by silica gel column chromatography (eluent: system B) to obtain a product tert-butyl (2R,4aR)-11-chloro-10-(2-fluoro-6-methoxyphenyl)-8-(2-isopropyl-4-(methylthio)pyridin-3-yl)-2,6-dimethyl-5,7-dioxo-1,2,4,4a,5,6,7,8-octahydro-3H-pyrazino[1',2':4,5]pyrazino[2,3-c][1,8]nap hthyridine-3-carboxylate 16u (150 mg, 207.75 μmol) with a yield of 81%.

MS m/z(ESI): 723.1 [M+1]$^+$

The Seventh Step

(2R,4aR)-11-chloro-10-(2-fluoro-6-hydroxyphenyl)-8-(2-isopropyl-4-(methylthio)pyridin-3-yl)-2,6-dimethyl-2,3,4,4a,6,8-hexahydro-1H-pyrazino[1',2':4,5]pyrazino[2,3-c][1,8]naphthyridine-5,7-dione Tert-butyl (2R,4aR)-11-chloro-10-(2-fluoro-6-methoxyphenyl)-8-(2-isopropyl-4-(methylthio)pyridin-3-yl)-2,6-dimethyl-5,7-dioxo-1,2,4,4a,5,6,7,8-octahydro-3H-pyrazino[1',2':4, 5]pyrazino[2,3-c][1,8]naphthyridine-3-carboxylate 16u (150 mg, 207.75 μmol) was added to dichloromethane (5 mL), cooled to 0° C., and dropwise added with boron tribromide (1 M, 13.34 mL) for reaction overnight at room temperature. After the reaction was completed, the reaction solution was poured into ice water (50 mL), and extracted with dichloromethane (50 mL). The aqueous phase was adjusted to weakly alkaline with saturated aqueous sodium carbonate solution, and extracted with ethyl acetate (10 mL) and water (10 mL). The organic phases were combined, washed with saturated brine (10 mL×3), and dried over anhydrous sodium sulfate to obtain a crude product (2R,4aR)-11-chloro-10-(2-fluoro-6-hydroxyphenyl)-8-(2-isopropyl-4-(methylthio)pyridin-3-yl)-2,6-dimethyl-2,3,4,4a,6,8-hexahydro-1H-pyrazino[1',2':4,5]pyrazino[2,3-c][1,8]naphthyridine-5,7-dione 16n (80 mg, 131.34 μmol) with a yield of 64.19%.

MS m/z(ESI): 609.1[M+1]$^+$

The Eighth Step

(2R,4aR)-3-acryloyl-11-chloro-10-(2-fluoro-6-hydroxyphenyl)-8-(2-isopropyl-4-(methylthio)pyri din-3-yl)-2,6-dimethyl-2,3,4,4a,6,8-hexahydro-1H-pyrazino[1',2':4,5]pyrazino[2,3-c][1,8]naphth yridine-5,7-dione (2R,4aR)-11-chloro-10-(2-fluoro-6-hydroxyphenyl)-8-(2-isopropyl-4-(methylthio)pyridi n-3-yl)-2,6-dimethyl-2,3,4,4a,6,8-hexahydro-1H-pyrazino[1',2':4,5]pyrazino[2,3-c][1,8]naphthyr idine-5,7-dione 16n (80 mg, 131.34 μmol) was added to dichloromethane (5 mL), cooled to 0° C., dropwise added with triethylamine (26.53 mg, 262.68 μmol), and slowly dropwise added with a solution of acryloyl chloride (12.92 mg, 142.71 μmol) in dichloromethane for reaction at 0° C. After the reaction was completed, the reaction solution was extracted with dichloromethane (10 mL) and water (10 mL) at room temperature. The organic phase was washed with saturated brine (10 mL×3), dried over anhydrous sodium sulfate, and concentrated under reduced pressure. The obtained residue was separated and purified by preparative liquid chromatography (separation column: AKZONOBEL Kromasil; 250×21.2 mm I.D.; 5 μm; mobile phase A: 0.05% TFA+$H_2O$, mobile phase B: acetonitrile; flow rate: 20 mL/min) to obtain a product (2R,4aR)-3-acryloyl-11-chloro-10-(2-fluoro-6-hydroxyphenyl)-8-(2-isopropyl-4-(methylthio)pyri din-3-yl)-2,6-dimethyl-2,3,4,4a,6,8-hexahydro-1H-pyrazino[1',2':4,5]pyrazino[2,3-c][1,8]naphth yridine-5,7-dione 16 (25 mg, 37.76 μmol) with a yield of 27.08%.

MS m/z(ESI): 663.1 [M+1]$^+$ $^1$H NMR (400 MHz, $CDCl_3$) δ 8.61 (d, J=5.3 Hz, 1H), 8.29 (s, 1H), 7.74 (s, 1H), 7.24 (d, J=2.0 Hz, 1H), 7.11 (d, J=5.4 Hz, 1H), 7.08-6.99 (m, 1H), 6.73-6.70 (m, 1H), 6.69 (t, J=1.3 Hz, 1H), 6.36 (dd, J=16.9, 2.0 Hz, 1H), 5.81 (dd, J=10.6, 1.9 Hz, 1H), 5.07 (s, 1H), 4.77 (d, J=14.0 Hz, 1H), 3.82 (dd, J=14.1, 4.4 Hz, 1H), 3.64 (d, J=4.0 Hz, 1H), 3.49 (s, 3H), 3.22 (d, J=12.2 Hz, 1H), 3.00 (dd, J=12.0, 3.6 Hz, 1H), 2.53-2.46 (m, 1H), 2.45 (s, 3H), 1.68 (s, 3H), 1.20 (d, J=6.7 Hz, 3H), 0.95 (d, J=6.7 Hz, 3H).

Example 6—Compound 17 and Compound 18

17

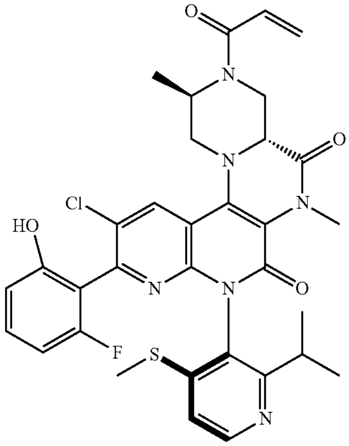

18

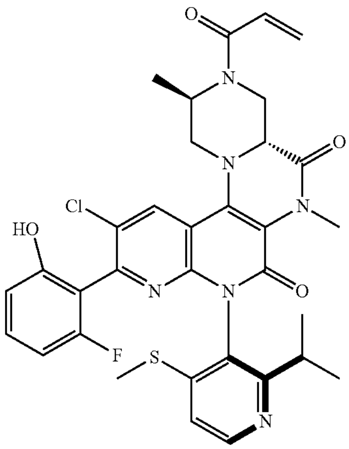

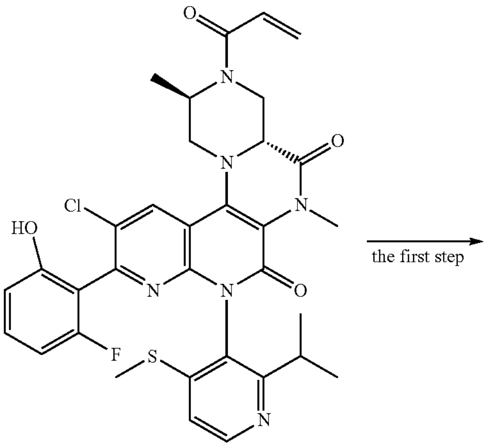

16

-continued

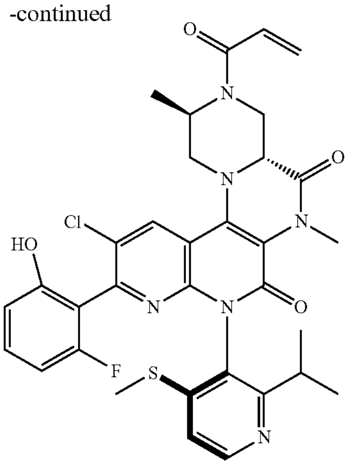

17

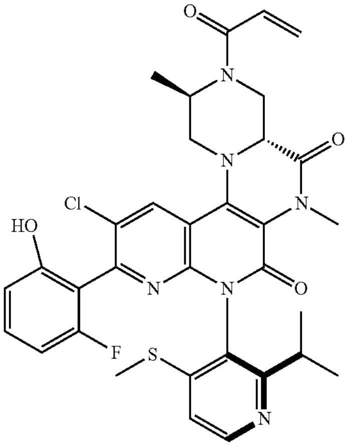

18

(2R,4aR)-3-acryloyl-11-chloro-10-(2-fluoro-6-hydroxy-phenyl)-8-(2-isopropyl-4-(methy lthio)pyridin-3-yl)-2,6-di-methyl-2,3,4,4a,6,8-hexahydro-1H-pyrazino[1',2':4,5] pyrazino[2,3-c][1, 8]naphthyridine-5,7-dione 16 (45 mg) was chirally resolved by preparative SFC (column type: ChiralPak AD, 250×30 mm I.D., 10 μm, 250×30 mm I.D., 10 μm; mobile phase: A for $CO_2$ and B for ethanol; column pressure: 100 bar; flow rate: 80 mL/min; detection wavelength: 220 nm; column temperature: 38° C.). Then purification was performed to obtain a compound 17 with a single configuration (with a shorter retention time) and a compound 18 with a single configuration (with a longer retention time).

Compound 17 with a single configuration (with a shorter retention time):

MS m/z(ESI): 663.2 $[M+1]^+$ 20 mg; retention time: 1.109 min; chiral purity: 100% ee.

Compound 18 with a single configuration (with a longer retention time):

MS m/z(ESI): 663.3 $[M+1]^+$ 10 mg; retention time: 2.525 min; chiral purity: 99.28% ee.

Biological Evaluation

Test Example 1. Determination of Covalent Binding Ability of Compounds of the Present Disclosure to KRAS G12C Protein The following method was used to determine the covalent binding ability of the compounds of the present disclosure to recombinant human KRAS G12C protein under in vitro conditions.

The experimental procedure is briefly described as follows: The recombinant human KRAS G12C protein (aa1-169) was prepared with a reaction buffer (20 mM HEPES, 150 mM NaCl, 1 mM $MgCl_2$, 1 mM DTT) at a concentration of 4 μM for later use. The test compound was prepared with DMSO into a 10 mM stock solution, which was then diluted with the reaction buffer for later use. First, 1.5 μL of the test compound diluted with the reaction buffer was added to each well (a final concentration of the reaction system was 3 M), then added with 23.5 μL of the reaction buffer, mixed well, then added with 25 μL of 4 μM recombinant human KRAS G12C protein for 5 min of incubation at room temperature, and added with 5 μL of acetic acid to stop the reaction. The samples were transferred to injection vials. The ratios of covalent binding between the test compounds and KRAS G12C protein were detected by Agilent 1290/6530 instrument, and the samples were analyzed in a liquid chromatography column (XBridge Protein BEH C4, 300 Å, 3.5 μm, 2.1 mm×50 mm). In the detection process, mobile phase A was 0.1% formic acid aqueous solution, mobile phase B was acetonitrile, the mobile phase elution program was as follows: mobile phase A was kept at 95% at 0-0.5 min, changed to 30% at 2.5 min for 0.5 min, and changed to 95% at 3.1 min for 1.9 min; and flow rate was 0.5 mL/min. Finally, the data was analyzed by MassHunter Workstation Software Bioconfirm Version B.08.00 to obtain the covalent binding rate between the test compound at a concentration of 3 μM and KRAS G12C protein under 5 min of incubation. See Table 1.

TABLE 1

Covalent binding rate of compounds of the present disclosure to KRAS G12C protein

| Compound number | Covalent binding rate (%) 3 μM, 5 min |
|---|---|
| 7 | 42.5 |
| 10 | 45.5 |
| 16 | 38.5 |
| 17 | 63.4 |

Conclusion: The compounds of the present disclosure have a good covalent binding rate with KRAS G12C protein.

Test Example 2. Inhibitory Activity of Compounds of the Present Disclosure on NCI-H358 Cell Proliferation The following method was used to determine the effect of the compounds of the present disclosure on the proliferation of NCI-H358 cells. NCI-H358 cells (containing KRAS G12C mutation) were purchased from the Cell Resource Center, Shanghai Institutes for Biology Sciences, Chinese Academy of Sciences, and cultured in RPMI 1640 medium containing 10% fetal bovine serum, 100 U penicillin, 100 μg/mL streptomycin and 1 mM sodium pyruvate. Cell viability was determined by CellTiter-Glo® Luminescent Cell Viability Assay Kit (Promega, Cat. No. G7573).

The experiment was conducted according to the steps in the kit instruction, which is briefly described as follows: The test compound was first prepared with DMSO into a 10 mM stock solution, which was then diluted with medium into a test sample with a final concentration of the compound ranging from 1000 nM to 0.015 nM Cells in the logarithmic growth phase were inoculated into a 96-well cell culture plate at a density of 800 cells per well, cultured overnight at 37° C. in a 5% $CO_2$ incubator, and then added with the test compound for 120 h of culture. After the culture was completed, 50 μL of CellTiter-Glo detection solution was added to each well, shaken for 5 min and left to stand for 10 min. Subsequently, the luminescence value of the sample in each well was read by a microplate in a luminescence mode. The percentage of inhibition rate of the compounds at each concentration was calculated by comparing with the value of the control group (0.3% DMSO). Then a nonlinear regression analysis on the log concentration-inhibition rate of the compounds was performed by the software GraphPad Prism 5 to obtain the $IC_{50}$ value of the compound inhibiting NCI-H358 cell proliferation. See Table 2. Table 2 $IC_{50}$ data of compounds of the present disclosure inhibiting NCI-H358 cell proliferation Compound number $IC_{50}$(nM)

TABLE 2

$IC_{50}$ data of compounds of the present disclosure inhibiting NCI-H358 cell proliferation

| Compound number | $IC_{50}$ (nM) |
|---|---|
| 7 | 67.2 |
| 10 | 73.4 |
| 16 | 39.9 |
| 17 | 21.1 |
| 18 | 98.5 |

Conclusion: The compounds of the present disclosure have a good inhibitory effect on the proliferation of NCI-H358 (human non-small cell lung cancer) cells.

Test Example 3. Inhibitory Activity of Compounds of the Present Disclosure on p-ERK1/2 in NCI-H358 Cells The following method was used to determine the inhibitory activity of the compounds of the present disclosure on p-ERK1/2 in NCI-H358 cells. In this method, Advanced phospho-ERK1/2 (Thr202/tyr204) kit (Cat. No. 64AER-PEH) from Cisbio company was used, and the detailed experimental operation can be referred to the kit instruction. NCI-H358 cells (containing KRAS G12C mutation) were purchased from the Cell Resource Center, Shanghai Institutes for Biology Sciences, Chinese Academy of Sciences.

The experimental procedure is briefly described as follows: NCI-H358 cells were cultured in RPMIH 1640 complete medium containing 10% fetal bovine serum, 100 U penicillin, 100 μg/mL streptomycin and 1 mM sodium pyruvate. NCI-H358 cells were plated in a 96-well plate at 30,000 per well with a complete medium, and cultured overnight at 37° C. in a 5% $CO_2$ incubator. The test compounds were prepared with DMSO into a 10 mM stock solution, which was then diluted with RPMI 1640 basal medium. 90 μL of RPMI 1640 basal medium containing the corresponding concentration of the test compound was added to each well at a final concentration of the test compound in the reaction system ranging from 1000 nM to 0.015 nM for 3 h and 40 min of culture in a cell incubator. Then 10 μL of hEGF (purchased from Roche, Cat. No. 11376454001) prepared with RPMI 1640 basal medium was added at a final concentration of 5 nM for 20 min of culture in the incubator. The cell supernatant was discarded, the cells were washed with ice-bathed PBS, and then 45 μL of 1× cell phospho/total protein analysis buffer (a component in Advanced phospho-ERK1/2 kit) was added to each well for lysis. The 96-well plate was placed on ice for half an hour of lysis, and then the lysate was detected according to the instruction of the Advanced phospho-ERK1/2 (Thr202/tyr204) kit. Finally, the fluorescence intensity of each well at emission wavelengths of 620 nM and 665 nM was measured on a microplate reader in TF-FRET mode at an excitation wavelength of 304 nM, and the ratio of the fluorescence intensity of each well at 665/620 was calculated. The percentage of inhibition rate of the test compounds at each concentration was calculated by comparing with the fluorescence intensity of the control group (0.1% DMSO). Then a nonlinear regression analysis on the log concentration-inhibition rate of the test compounds was performed by the software GraphPad Prism 5 to obtain the $IC_{50}$ value of the compounds. See Table 3.

TABLE 3

$IC_{50}$ data of compounds of the present disclosure inhibiting p-ERK1/2 in NCI-H358 cells

| Compound number | $IC_{50}$ (nM) |
|---|---|
| 16 | 93.0 |
| 17 | 83.4 |

Conclusion: The compounds of the present disclosure have a good proliferation inhibitory effect on p-ERK1/2 in NCI-H358 cells.

Test Example 4. Inhibitory Activity of Compounds of the Present Disclosure on hERG Potassium Ion Channel 1. Cell Culture 1.1 The cells used in this experiment were CHO cell line (provided by Sophion Bioscience, Denmark) transfected with hERG cDNA and stably expressing hERG channels, with a cell generation of 17. The cells were cultured in a medium containing the following components (all obtained from Invitrogen): Ham's F12 medium, 10% (v/v) inactivated fetal bovine serum, 100 μg/mL hygromycin B, and 100 μg/mL geneticin.

1.2 CHO hERG cells were cultured in a petri dish containing the above culture medium in an incubator containing 5% $CO_2$ at 37° C. 24 to 48 h before the electrophysiological experiment, CHO hERG cells were transferred to a round glass slide placed in a petri dish, and cultured in the same medium and conditions as above. The density of CHO hERG cells on each round glass slide met the requirement that the majority of cells were independent and individual.

2. Experimental Solution

The following solutions (recommended by Sophion) were used for electrophysiological recordings.

Components of Intracellular and Extracellular Fluids

| Reagent | Extracellular fluid (mM) (EC 0.0.0 NaCl-Ringer's solution) | Intracellular fluid (mM) (IC 0.0.0 KCl-Ringer's solution) |
|---|---|---|
| $CaCl_2$ | 2 | 5.374 |
| $MgCl_2$ | 1 | 1.75 |
| KCl | 4 | 120 |
| NaCl | 145 | — |
| Glucose | 10 | — |
| HEPES | 10 | 10 |
| EGTA | — | 5 |
| Na-ATP | — | 4 |
| pH | 7.4 (adjusted by NaOH) | 7.25 (adjusted by KOH) |
| Osmotic pressure | Osmotic pressure of about 305 mOsm | Osmotic pressure of about 295 mOsm |

3. Electrophysiological Recording Process 3.1 Electrophysiological Recording System A fully automated QPatch system (Sophion, Denmark) was used for whole-cell current recordings. Cells were clamped at a voltage of −80 mV. Cell clamp voltage was depolarized to +20 mV to activate hERG potassium channels, and then clamped to −50 mV after 2.5 s to abolish inactivation and produce an outward tail current. The peak value of the tail current was used as the hERG current value.

3.2 QPatch Experimental Steps

After reaching a membrane-permeable whole-cell configuration state during the initial phase, the cells were recorded for at least 120 s to reach stabilization. Then during the whole process, the above voltage pattern was applied to the cells every 15 s. In the above parameter threshold recording, only stable cells were allowed to participate in drug treatment. An extracellular solution containing 0.1% DMSO (solvent) was applied to the cells to establish a baseline, and the current was allowed to stabilize for 3 min. The cells were remained in the test environment after a compound solution was added until the effect of the compound reached a steady state or 4 min as a limit. In the test experiments with different concentration gradients of the compound, the compound was added to the clamped cells from low to high concentration. After the test on the compound was completed, the cells were washed with the extracellular solution until the current returned to a steady state.

4. Compound Preparation 4.1 The 10 mM stock solution of the compound was gradiently diluted with an extracellular fluid to a final concentration with μM as a unit.

4.2 The highest test concentration was 30 μM, followed by 5 concentrations of 10, 3, 1, 0.3 and 0.1 μM.

4.3 Except for the final concentration of DMSO in the compound of 30 μM was 0.3%, the final concentration of DMSO in the compound solutions of other concentrations was 0.1%. All the compound solutions were routinely ultrasonicated and shaken for 5 to 10 min to ensure complete dissolution of the compound.

5. Data Analysis

The test data were analyzed by analysis software Qpatch provided by Sophion, Excel, Graphpad Prism, and the like.

6. Experimental Results

Table 4 shows the inhibition results of hERG current by the compounds of the present disclosure.

TABLE 4

| Inhibition results of hERG current by compounds of the present disclosure | |
|---|---|
| Compound number | hERG $IC_{50}$ (μM) |
| 17 | >30 |

Conclusion: The inhibition of heart hERG potassium channel by drugs is the main reason why drugs lead to QT prolongation syndrome. It can be seen from the experimental results that the compound 17 of the present disclosure has no obvious inhibitory effect on the heart hERG potassium ion channel, and can avoid cardiotoxic side effects at high doses.

Test Example 5. ICR Mouse Pharmacokinetic Research on Compounds of the Present Disclosure 1. Experimental Purpose ICR mice were used as test animals. The drug concentrations in plasma at different time points of the compounds in Comparative Example 1 and Example 17 of the present disclosure intragastrically administered to the mice were determined by LC/MS/MS method, to study the pharmacokinetic characteristics of the compounds of the present disclosure in mice.

2. Experimental Method 2.1 Experimental Drugs and Animals

Compounds of Comparative Example 1 and Example 17

ICR mice, male, weighing 29.2-34.9 g, were purchased from Beijing Vital River Experimental Animal Technology Co., Ltd.

2.2 Drug Preparation

Preparation for intragastric administration: An appropriate amount of the compound to be tested was weighed, added with an appropriate amount of DMSO: PEG 200=5%: 95% (v/v), shaken by vortex, and prepared into a solution with a final concentration of 0.5 mg/mL.

2.3 Administration

ICR mice, the test compound intragastric administration group (nine mice in a single group).

Intragastric administration group: After fasting overnight, the mice were intragastrically administered at a dose of 5 mg/kg and a volume of 10 mL/kg, and fed 4 h after the administration.

3. Operation

Intragastric administration group: About 100 μL of blood was collected through the orbital vein before administration and at 0.25 h, 0.5 h, 1 h, 2 h, 4 h, 8 h, 12 h and 24 h after administration.

The whole blood sample was put in an EDTA-K2 anticoagulant tube. The plasma was separated by centrifugation at 1500 g for 10 min. The collected upper layer plasma was stored at −40 to −20° C. before analysis.

The content of the compound to be tested in mouse plasma was determined by LC-MS/MS after the compound was intragastrically administered.

4. Results of Pharmacokinetic Parameters

The pharmacokinetic parameters of the compounds of the present disclosure are shown in Table 5.

TABLE 5

| Pharmacokinetic parameter results | | | | |
|---|---|---|---|---|
| | Pharmacokinetic experiment | | | |
| Compound number | Method of administration Dosage | Blood concentration Cmax (ng/mL) | Area under curve $AUC_{0-\infty}$ (ng · h/mL) | Half-life $T_{1/2}$ (h) |
| Comparative Example 1 | Intragastric administration 5 mg/kg | 928 | 4180 | 1.95 |
| 17 | Intragastric administration 5 mg/kg | 1400 | 6380 | 2.36 |

Conclusion: Compared with Comparative Example 1, the pharmacokinetic absorption of compound 17 of the present disclosure is good, and its plasma concentration, area under the curve and half-life are significantly better than those of Comparative Example 1, showing better pharmacokinetic characteristics.

Note: Comparative Example 1 is compound Z27-2 of WO2021083167A1, which was prepared according to Example 27 of WO2021083167A1, and the specific structure is as follows:

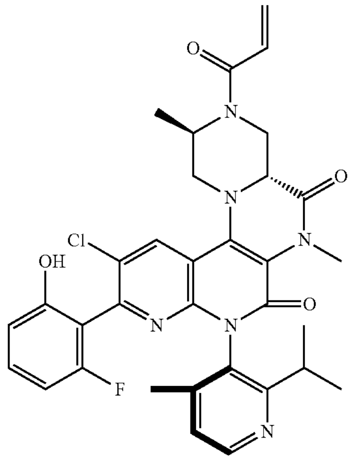

Test Example 6. Pharmacodynamics Test on Compounds of the Present Disclosure in NCI-H358 Cell BALB/c Nude Mouse Subcutaneous Zenograft Model 1. Experimental Purpose This test is used to evaluate the anti-tumor effect and safety of the compound 17 of the present disclosure in the animal model of BALB/c nude mouse subcutaneously transplanted with NCI-H358 (human non-small cell lung cancer) cell line after oral intragastric administration for 14 days, once a day.

2. Preparation of Test Compound 2.1 Preparation for Blank Administration:

An appropriate volume of a preparation containing DMA (dimethylacetamide): 30% solutol HS 15: saline=10:10:80 (v/v/v) was prepared as a test solution for the blank group administration.

2.2 Preparation of Compound 17 for Oral Administration

An appropriate amount of compound 17 was weighed into a 10 mL centrifuge tube, added with an appropriate amount of DMA, shaken by vortex for complete dissolution of the solid matter, then added with an appropriate volume of 30% solutol HS 15, shaken by vortex, mixed well, and added with normal saline to make the ratio of DMA:30% solutol HS 15:saline 10:10:80 (v/v/v), for a preparation at a concentration of 1 mg/mL for administration.

3. Experimental Animals

12 BALB/c nude mice, female, aging 6-7 weeks (the age of mice at the time of tumor cell inoculation), were purchased from Jiangsu GemPharmatech Co., Ltd., with license No. SCXK (Su) 2019-0009, and an animal certificate No. 202113149.

4. Cell Culture

NCI-H358 cells were cultured in RPMI 1640 medium containing 10% fetal bovine serum, 1% sodium pyruvate and 1% glutamine. NCI-H358 cells in the logarithmic growth phase were collected, and the cells were resuspended in PBS at a suitable concentration for subcutaneous tumor inoculation in nude mice.

5. Animal Inoculation and Grouping

About $3.7\times10^6$ NCI-H358 cells were subcutaneously inoculated on the right side of the back of female BALB/c nude mice. When the average volume of the tumor reached about 100-150 $mm^3$, the mice were randomly divided into 2 groups according to the size of the tumor, 6 mice in each group.

6. Animal Administration and Observation

After tumor inoculation, a subcutaneous xenograft tumor model was established. Each treatment group and the vehicle control group were orally intragastrically administered for 14 days. The animals were weighed daily, and the tumor volume was measured twice a week.

Formulas for calculating the tumor volume (TV), relative tumor proliferation rate (T/C), relative tumor growth inhibition rate (TGI) and tumor inhibition rate (IR) are as follows:

(1) TV (tumor volume)=$\frac{1}{2}\times a\times b^2$, where a and b represent the length and width of the tumor, respectively;

(2) T/C (relative tumor proliferation rate, %)=$T_{RTV}/C_{RTV}\times$ 100%, where $T_{RTV}$ is the RTV of the treatment group, and $C_{RTV}$ is the RTV of the control group;

(3) TGI % (tumor growth inhibition rate)=(1−T/C)× 100%; where T and C are the relative tumor volumes at a specific time point in the treatment group and the control group, respectively.

(4) IR (%) (tumor weight inhibition rate)=$(1-TW_t/TW_c)\times$ 100%, where $TW_t$ is the tumor weight in the treatment group, and TW is the tumor weight in the control group.

7. Results

Figure 2:
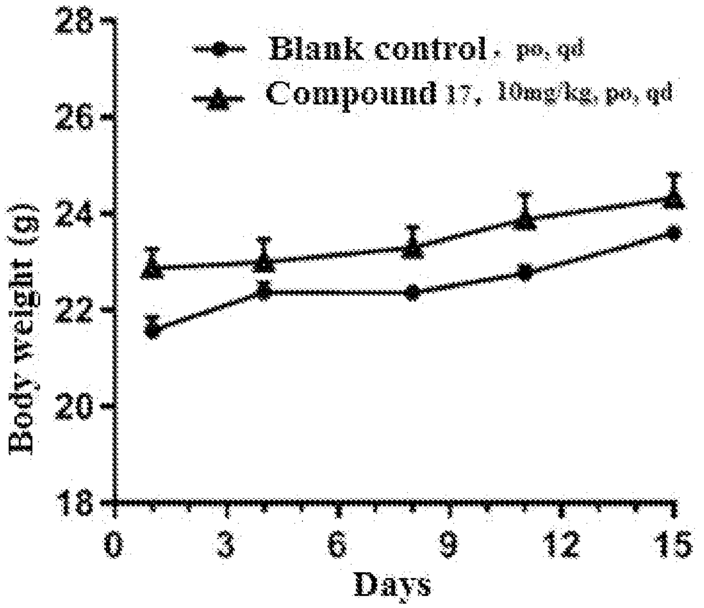
FIG. 2 shows the change in body weight of BALB/c nude mice with NCI-H358 cell xenograft tumor treated with the compound 17 of the present disclosure in Test Example 6.

FIG. 1 shows the change in tumor volume of BALB/c nude mice with NCI-H358 cell xenograft tumor treated with the compound 17 of the present disclosure in Test Example 6;

FIG. 2 shows the change in body weight of BALB/c nude mice with NCI-H358 cell xenograft tumor treated with the compound 17 of the present disclosure in Test Example 6.

TABLE 6

Drug efficacy analysis of compound 17 in each group of NCI-H358 cell subcutaneous xenograft model on Day 15 after administration

| Experimental group | Tumor volume ($mm^3$) (x ± S) | TGI (%) | T/C (%) |
|---|---|---|---|
| Blank control | 286 ± 32 | — | — |
| Compound 17 | 52 ± 15 | 84.4% | 15.6% |

TABLE 6-continued

Drug efficacy analysis of compound 17 in each group of NCI-H358 cell subcutaneous xenograft model on Day 15 after administration

| Experimental group | Tumor volume ($mm^3$) (x ± S) | TGI (%) | T/C (%) |
|---|---|---|---|

Note:
The tumor volume data are expressed as "mean ± standard error";

TABLE 7

Tumor weight of nude mice in each group of NCI-H358 cell subcutaneous xenograft model

| Experimental group | Tumor weight (g) (x ± S) | IR |
|---|---|---|
| Blank control | 0.1707 ± 0.0234 | — |
| Compound 17 | 0.0157 ± 0.0033 | 90.8% |

Note:
The tumor volume data are expressed as "mean ± standard error";

It can be seen from Tables 6-7 and FIGS. 1-2 that at a dose of 10 mg/kg (po, qd), the compound of the present disclosure (taking compound 17 as an example) can exhibit an obvious growth inhibitory effect on the tumor model in mice established based on NCI-H358 cells within 14 days, without significant body weight change, showing good safety and tolerance.

The invention claimed is:

1. A compound represented by general formula (III), or a stereoisomer, tautomer, or pharmaceutically acceptable salt thereof:

(III)

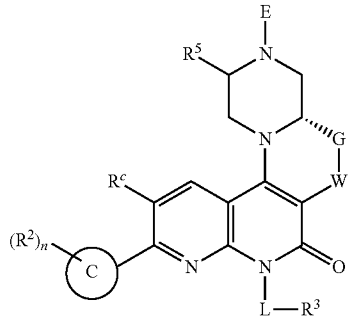

wherein:

E is

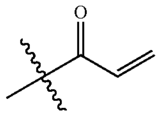

;

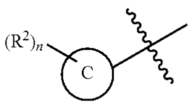

is

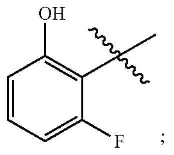 [SMILES: *c1c(O)cccc1F]
;

L is a chemical bond;
G is C═O;
W is $NR^f$;
$R^f$ is a hydrogen atom;
$R^3$ is

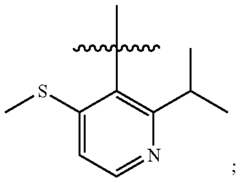 [SMILES: *c1c(SC)ccnc1C(C)C]
;

$R^5$ is $C_1$-$C_4$ alkyl.

2. The compound or the stereoisomer, tautomer, or pharmaceutically acceptable salt thereof according to claim 1, which is a compound represented by general formula (V) or (VI), or a stereoisomer, tautomer, or pharmaceutically acceptable salt thereof:

(V)

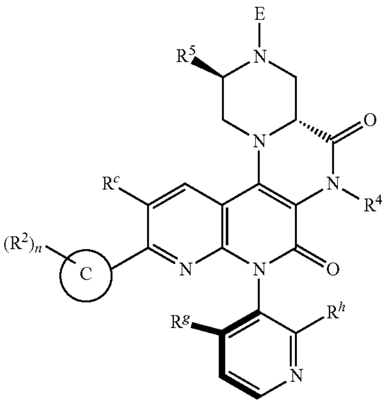

(VI)

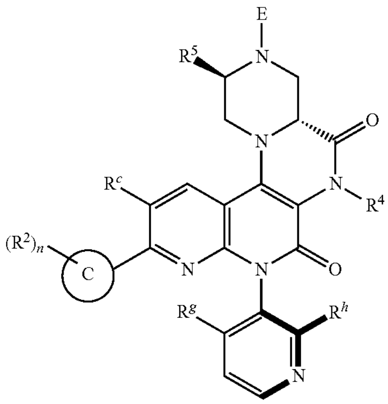

wherein:
$R^g$ is —S—$CH_3$;
$R^h$ is isopropyl;
$R^4$ is methyl; and
ring C, $R^2$, $R^5$, $R^c$, E and n are as defined in claim 1.

3. The compound or the stereoisomer, tautomer, or pharmaceutically acceptable salt thereof according to claim 1, wherein the compound is selected from the group consisting of:

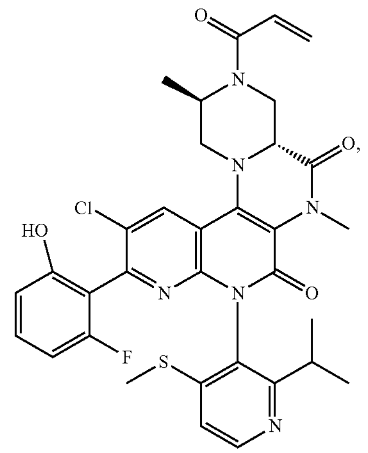

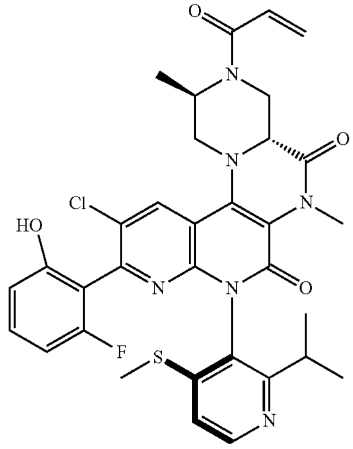

and

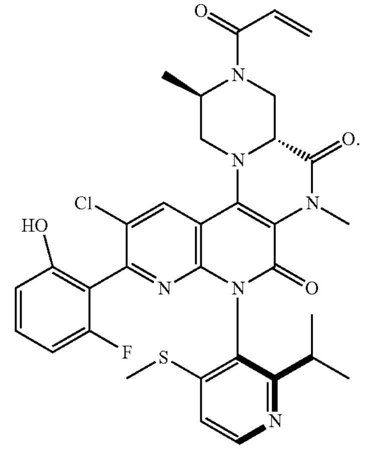

4. A pharmaceutical composition, comprising an effective dose of the compound or the stereoisomer, tautomer, or pharmaceutically acceptable salt thereof according to claim 1, and a pharmaceutically acceptable carrier, excipient or a combination thereof.

5. A method for treating a disease mediated by KRAS mutation, comprising administering the compound or the stereoisomer, tautomer, or pharmaceutically acceptable salt thereof according to claim 1 to a subject in need thereof.

6. The method according to claim 5, wherein the KRAS mutation is KRAS G12C mutation.

7. The method according to claim 5, wherein the disease mediated by KRAS mutation is cancer, and the cancer is selected from the group consisting of pancreatic cancer, colorectal cancer, lung cancer, multiple myeloma, uterine cancer, cholangiocarcinoma, gastric cancer, bladder cancer, diffuse large B-cell lymphoma, rhabdomyosarcoma, squamous cell carcinoma, cervical cancer, and testicular germ cell carcinoma.

8. The method according to claim 5, wherein the disease mediated by KRAS mutation is selected from the group consisting of pancreatic cancer, colorectal cancer and lung cancer.

9. The method according to claim 8, wherein the lung cancer is non-small cell lung cancer.

* * * * *